US010188706B2

(12) United States Patent
Higazi et al.

(10) Patent No.: US 10,188,706 B2
(45) Date of Patent: Jan. 29, 2019

(54) PLASMINOGEN ACTIVATOR MUTANTS AS ANTI-FIBRINOLYTIC AGENTS

(71) Applicant: HADASIT MEDICAL RESEARCH SERVICES & DEVELOPMENT LIMITED, Jerusalem (IL)

(72) Inventors: Abd Higazi, D.N. Shimshon (IL); Nuha Hijazi, D.N. Shimshon (IL)

(73) Assignee: HADASIT MEDICAL RESEARCH SERVICES & DEVELOPMENT LIMITED, Jerusalem (IL)

(*) Notice: Subject to any disclaimer, the term of this patent is extended or adjusted under 35 U.S.C. 154(b) by 214 days.

(21) Appl. No.: 14/412,873

(22) PCT Filed: Jul. 2, 2013

(86) PCT No.: PCT/IL2013/050559
§ 371 (c)(1),
(2) Date: Jan. 5, 2015

(87) PCT Pub. No.: WO2014/006613
PCT Pub. Date: Jan. 9, 2014

(65) Prior Publication Data
US 2015/0190482 A1 Jul. 9, 2015

Related U.S. Application Data

(60) Provisional application No. 61/668,172, filed on Jul. 5, 2012.

(51) Int. Cl.
| | | |
|---|---|---|
| *A61K 38/48* | (2006.01) | |
| *A61K 38/36* | (2006.01) | |
| *A61K 45/06* | (2006.01) | |
| *C12N 9/72* | (2006.01) | |

(52) U.S. Cl.
CPC ............ *A61K 38/482* (2013.01); *A61K 38/36* (2013.01); *A61K 45/06* (2013.01); *C12N 9/6459* (2013.01); *C12Y 304/21068* (2013.01)

(58) Field of Classification Search
None
See application file for complete search history.

(56) References Cited

U.S. PATENT DOCUMENTS

| | | | |
|---|---|---|---|
| 5,612,029 A | 3/1997 | Bennett et al. | |
| 6,033,664 A | 3/2000 | Verheijen | |
| 2010/0284998 A1 | 11/2010 | Smith et al. | |
| 2011/0008313 A1 | 1/2011 | Higazi et al. | |

FOREIGN PATENT DOCUMENTS

| | | |
|---|---|---|
| WO | 9324635 A1 | 12/1993 |
| WO | 2012017310 A2 | 2/2012 |

OTHER PUBLICATIONS

Paoni, N.F., et al. 1993 Thrombosis and Haemostasis 70(2): 307-312.*
Levine, M.N., et al. 2001 CHEST 119: 108S-121S.*
Ker K. et al., "Avoidable mortality from giving tranexamic acid to bleeding trauma patients: and estimation based on who mortaliy data, a systematic literature review and data from the Crash-2 trail" BMC Emerg Med., 12:3 (2012).
Stewart R et al., "Identification of the Mechanism Responsible for the Increased Fibrin Specificity of TNK-Tissue Plasminogen Activator Relative to Tissue Plasminogen Activator" J Biol Chem. 275:10112-10120 (2000).
Rabbani et al., "Structural Requirements for the Growth Factor Activity of the Aminoterminal Domain of Urokinase" J Biol Chem., 267(20):14151-6 (1992).
Bdeir K. et al., "The kringle stabilizes urokinase binding to the urokinase receptor" Blood. 102(10):3600-8 (2003).
Stump et al., "Purification and Characterization of a Novel Low Molecular Weight Form of Single-Chain Urokinase-type Plasminogen Activator" J Biol Chem. 261(36):17120-17126 (1986).
Higazi et al.,"Enhancement of the Enzymatic Activity of single-chain Urokinase Plasminogen Activator solube Urokinase Receptor" J Biol Chem. 270(29):17375-80 (1995).
Hoylaerts M et al., "Kinetics of the Activation of Plasminogen by Human Tissue Plasminogen Activator" J Biol Chem. 257:2912-2919 (1982).
Collen D. et al, "Activation of Plasminogen by Pro-urokinase" J Biol Chem., 261:1259-1266 (1986).
Lijnen HR et al., "Activation of Plasminogen by Pro-urokinase" J Biol Chem. 261(3):1253-8 (1986).
Collen D. et al., "The Fibrinolytic system in man" Crit Rev Oncol Hematol. 4(3):249-301 (1986).
Violand. et al., "The effect of a-,w-Amino Acids on Human Plasminogen Structure and Activation" J Biol Chem. 253:5395-5401 (1978).
Deloukas et al "Homo sapiens chromosome 10 genomic contig, GRCh37.p13 Primary Assembly" Gene acc. NT_030059.13 (accessed May 18, 2015).
Lander et al "Homo sapiens chromosome 8 genomic contig, GRCh37.p13 Primary Assembly" DNA acc. NT_167187.1 (accessed Jul. 6, 2015).
Alzheimer "Presenile and Senile Dementia" OMIM No. 104300 (accessed May 18, 2015).
Hyperfibrinolysis "Thrombophilia, Familial, Due to Decreased Release of Tissue Plasminogen Activator; THPH9" OMIM No. 612348 (accessed Jul. 7, 2015).
Diamandis et al Bleeding disorder, platelet-type, 5 BDPLT5 "Quebec Platelet Disorder: QPD" OMIM No. 601709.
Deutsch et al . "Plasminogen: Purification from Human Plasman by Affinity Chromatography" Science , 170(3962):1095-6 (1970).
Higazi et al., Iysis of Plasma Clots by Urokinase-Soluble Urokinase Receptor Complexes Blood , 92(6):2075-83 (1998).
Chen et al. "An Experimental Model of Closed Head Injury in Mice: Pathophysiology, Histopathology, and Cognitive Deficits" J. Neurotrauma, 13:557-568 (1996).

(Continued)

*Primary Examiner* — Marsha Tsay
(74) *Attorney, Agent, or Firm* — Browdy and Neimark, PLLC

(57) ABSTRACT

The invention relates to an anti fibrinolytic composition comprising at least one tPA mutant that carries at least one point mutation substituting Ser$^{481}$ to Ala on tPA, said mutant inhibits the fibrinolytic activity of at least one of tPA and uPA and therefore may be used for treating disorders associated with fibrinolytic processes, specifically, coagulopathies, thrombocytopenia and bleeding. The invention further provides methods and uses of the mutants of the invention.

14 Claims, 17 Drawing Sheets

Specification includes a Sequence Listing.

(56) References Cited

OTHER PUBLICATIONS

Nassar et al. "Regulation of Airway Contractility by Plasminogen Activators throught N-Methyl-D-Aspartate Receptor-1", Am J Respir Cell Mol Biol 43: 703-711, (2010).
Kim et el. "Inhibition of endothelial cell proliferation by the recombinant kringle domain of tissue-type plasminogen activator" 301 (4 ) 740-746 (May 16, 2003).
Weitz. "A novel approach to thrombin inhibition." . vol. 109 suppl 1 P. s17-s22 (Jul. 15, 2001).
Keyt et al "A faster-acting and more potent form of tissue plasminogen activator" Proc. Natl. Acad. Sci. 91:3670-3674 (Apr. 1994).
Cesarman-Maus et al "Molecular mechanisms of fibrinolysis" , bjh. 129 : 307-321 (2005).
Vaughan et al "Recombinant Plasminogen Activator Inhibitor-1 Reverses the Bleeding Tendency Associated with the Combined Administration of Tissue-type Plasminogen Activator and Aspirin in Rabbits" J. Clin. Invest. The American Society of Clinical Investigation 84 :586-591 (1989).
Cugno et al "Antibodies to tissue-type plasminogen activator (tPA) in patient with antiphospholipid syndrome: evidence of interaction between the antibodies and the catalytic domain of tPA in 2 patients" Blood2121-2126 (2004).
Bennett "A faster-acting and more potent form of tissue plasminogen activator" Proc. Natl. Acid Sci. 91 : 3670-3674 (1994).
Tengborn "Fibrinolytic Inhibitors in the Management of Bleeding Disorders" World Federation of Hemophilia. 42 : 1-14 (Nov. 2012).
Armstead et al "tPA-S481A Prevents Neurotoxicity of Endogenous tPA in Traumatic Brain Injury" Journal of Neurotrauma, 29: 1794-1802 (Jun. 10, 2012).

Armstead et al tPA-S A Prevents Impairment of Cerebrovascular Autoregulation by Endogenous tPA after Traumatic Brain Injury by Upregulating p38 MAPK and Inhibiting ET-1, Journal of Neurotrauma 30: 1898-1907 (Nov. 15, 2013).
Graham et al "Real-Time Measurement of Lysis of Mural Platelet Deposits by Fibrinolytic Agents under Arterial Flow" Annals of Biomedical Engineering, 26 : 712-724 (1998).
Hemphill "Treatin Warfarin-Related Intracerebral Hemorrhage Is Fresh Frozen Plasma Enough?" Journal of the American Heart Association Stroke 37: 6-8 (2006).
Kunitada et al "Inhibition of clot lysis and decreased binding of tissue-type plasminogen activator as a consequence of clot retraction" Blood 72 : 1420-1427 (1992).
Canio J. Refino et al., A variant of t-PA (T103N, KHRR 296-299 AAAA) that, by bolus, has increased potency and decreased systemic activatio of plasminogenThrombosis and Haemostasis 70(2):313-319 (1993).
Bruce A. Keyt et al., A faster-acting and more potent form of tissue plasminogen activator, Proc. Natl. Acad. Sci. USA 91: 3670-74 (1994).
Hijazi N et al. Endogenous plasminogen activators mediate progressive intracerebral hemorrhage after traumatic brain injury in mice. Blood, 125:2558-2567 (2015).
Pleines I et al. Megakaryocyte-specific RhoA deficiency causes macrothrombocytopenia and defective platelet activation in hemostasis and thrombosis. Blood, 119:1054-1063 (2012).
Arif Hakan Demirel et al., Effects of primary suture and fib sealant on hemostasis and liver regeneration in an experimental liver injury. World J Gastroenterol, 14(1):81-84 (2008).
Roos et al, "Antifibrinolytic therapy for aneurysmal subarachnoid haemorrhage (Review)," The Cochrane Library, issue 2, pp. 1-19 (2003).

\* cited by examiner

PLASMINOGEN ACTIVATOR MUTANTS AS ANTI-FIBRINOLYTIC AGENTS

FIELD OF THE INVENTION

The invention relates to the treatment of conditions with an increased bleeding tendency. More specifically, the invention relates to plasminogen activator mutants and anti fibrinolytic compositions thereof that inhibit the fibrinolytic activity of tPA and uPA for use in treating fibrinolysis related-disorders.

BACKGROUND OF THE INVENTION

Various publications are referenced herein either by author, and others by patent application numbers/patent numbers. The disclosures of these publications, patents and patent applications are hereby incorporated by reference in their entireties.

Injuries are a major cause of death throughout the world. Traffic accidents cause more than a million deaths annually, are the ninth leading cause of death globally and are expected to become the third leading cause of death and disability by 2020. Moreover, about 1.6 million people die as a result of intentional acts of interpersonal, collective or self-directed violence every year. More than 90% of trauma deaths occur in relatively poor countries. An additional factor contributing to hospital deaths is hemorrhage, considered to be responsible for about a third of in-hospital trauma deaths and constituting a contributory factor to death from multi-organ failure.

The haemostatic system helps to maintain the circulation after severe vascular injury, whether traumatic or surgical in origin. Major surgery and trauma trigger similar haemostatic responses and in both situations severe blood loss presents an extreme challenge to the coagulation system. Part of the undesired responses to surgery and trauma is stimulation of clot breakdown (fibrinolysis), which may, in some cases, become deleterious (hyper-fibrinolysis).

Antifibrinolytic agents reduce blood loss in patients with both normal and exaggerated fibrinolytic responses to surgery, without apparently increasing the risk of postoperative complications.

Tranexamic acid is a synthetic derivative of the amino acid lysine that inhibits fibrinolysis by blocking the lysine binding sites on plasminogen. A systematic review of randomised trials of tranexamic acid in patients undergoing elective surgery identified 53 studies including 3836 participants. Tranexamic acid reduced the need for blood transfusion by a third (Ker K. et al., BMC Emerg Med., 2012, 12:3).

Early administration of a short course of tranexamic acid reduced death, vascular occlusive events and the frequency of blood transfusions in trauma patients with significant hemorrhage or at risk for such an event (Ker K. ibid.).

The fibrinolytic cascade in mammals is composed by two principal components, the pro-enzyme plasminogen and two plasminogen activators tissue-type plasminogen activator (tPA) and urokinase plasminogen activator (uPA). Endogenous fibrinolysis begins by the binding of plasminogen to fibrin, the principal component of blood clots, flowed by its activation by tPA or uPA to the proteolytic active enzyme plasmin. The newly-generated plasmin cleaves fibrin clots into soluble fibrin degradation products (SFDP) that are usually taken up by the liver.

tPA is a trypsin-like serine protease that consists of five domains: a fibronectin finger-like domain (F), an epidermal growth factor domain (EGF), two kringle domains (K1 and K2), and a protease domain (P). In addition to the binding to its substrate plasminogen, tPA binds also to fibrin. Binding of tPA to fibrin is predominantly mediated by its finger domain and with some participation of K1 that also mediates its rapid clearance from the circulation (Stewart R et al., J Biol Chem. (2000), 275:10112-10120.)

uPA is expressed as a single-chain molecule (scuPA) composed of an N-terminal fragment (ATF; amino acids 1-135) and a protease domain (amino acids 136-411), also known as low molecular weight uPA (LMW-uPA). The amino-terminal fragment (ATF) is itself composed of 2 independent domains, the amino-terminal growth factor-like domain (GFD; amino acids 1-43), which is known to bind to the uPA receptor, and a single kringle (K; amino acids 47-135) (Rabbani S A et al., J Biol Chem. (1992), 267(20): 14151-6; Bdeir K. et al., Blood. (2003), 102(10):3600-8). scuPA expresses plasminogen activator activity when converted to a 2-chain molecule (tcuPA) by plasmin (Stump D C et al., J Biol Chem. (1986), 261(36):17120-6) or as a single-chain molecule when bound to its receptor (Higazi A et al., J Biol Chem. (1995), 270(29):17375-80). Although in the process of plasminogen activation, tPA and uPA cleave the same single peptide bond between the amino acids Arg560 and Val561 in plasminogen, the mechanism of there fibrinolytic activities is totally different.

Fibrinolysis by tPA begins by the co-binding of tPA and plasminogen to fibrin, leading to a very high local concentrations of both agents on the clot surface and subsequent increase of the activation efficiency plasminogen by tPA by several orders of magnitude over that occurring in the absence of fibrin (Hoylaerts M et al., J Biol Chem. (1982), 257:2912-2919).

Although the presence of fibrin increases also the activation of plasminogen by uPA, uPA and in contrast to tPA, does not bind to fibrin (Collen D. et al, J Biol Chem. (1986), 261:1259-1266.). It has been shown that the binding of plasminogen to fibrin induces conformational changes in plasminogen that increases its affinity to uPA (Lijnen H R et al., J Biol Chem. (1986), 261(3):1253-8; Collen D. et al., Crit Rev Oncol Hematol. (1986), 4(3):249-301; Collen D. et al., J Biol Chem. (1978), 253:5395-5401).

Inhibitors of plasminogen activators can be used in any post-trauma situation, whether it affects the head, chest abdomen or other parts of the body. They could also be used in post partum bleeding, or during any surgery that may induce bleeding. An additional use could be in hemorrhagic stroke, subarachnoid hemorrhage or other conditions with an increased bleeding tendency, such as hemophilia or disseminated intravascular coagulation (DIC) patients and as biological glue.

SUMMARY OF THE INVENTION

According to a first aspect, the present invention relates to an anti fibrinolytic composition comprising at least one tPA (tissue plasminogen activator) mutant that carries a point mutation in position 481 of the Wild type molecule as denoted by SEQ ID NO. 7, substituting $Ser^{481}$ to Ala. More specifically, the mutant used for the composition of the invention inhibits the fibrinolytic activity of at least one of tPA and uPA (urokinase plasminogen activator). In certain embodiments, the composition of the invention may comprise the tPA mutant provided by the invention that carries a point mutation in position 481 of the Wild type molecule as denoted by SEQ ID NO. 7, substituting $Ser^{481}$ to Ala and at least one further mutation that may be any one of: (a) point mutations in positions 299-302 of the Wild type molecule as denoted by SEQ ID NO. 7, substituting KHRR$^{299\text{-}302}$ to AAAA; (b) point mutations in positions 120 and 106106 of the Wild type molecule as denoted by SEQ ID NO. 7, substituting N$^{120}$ to Q and T$^{106106}$ to N; and (c) deletion of at least one of the finger and K1 domains, as denoted by SEQ ID NO. 4.

According to one of its aspects, the invention provides a composition as described by the invention, for use in a method for the treatment, amelioration, inhibition or prophylaxis of a disease, disorder, or condition associated with fibrinolysis.

In yet another aspect, the invention provides an isolated tPA mutated molecule, or any fragment or functional derivative thereof. More specifically, the tPA mutant provided by the invention carries a point mutation in position 481 of the Wild type molecule as denoted by SEQ ID NO. 7, substituting Ser$^{481}$ to Ala and at least one further mutation that may be any one of: (a) point mutations in positions 299-302 of the Wild type molecule as denoted by SEQ ID NO. 7, substituting KHRR$^{299\text{-}302}$ to AAAA; (b) point mutations in positions 120 and 106106 of the Wild type molecule as denoted by SEQ ID NO. 7, substituting N$^{120}$ to Q and T$^{106106}$ to N; and (c) deletion of at least one of the finger and K1 domains, as denoted by SEQ ID NO. 4.

In yet another aspect, the invention relates to a method for the treatment, amelioration, inhibition or prophylaxis of a disease, disorder, or condition associated with fibrinolysis in a subject in need thereof. More specifically, the method of the invention comprises the step of administering to said subject, a therapeutically effective amount of at least one tPA mutated molecule described by the invention.

According to a further aspect, the present invention also provides a biological glue comprising at least one of the tPA mutated molecules of the invention and at least one coagulation promoting agent.

The invention further provides the uses of these mutants as anti-fibrinolytic agents, as well as kits for treating fibrinolysis associated disorders.

These and other aspects of the invention will become apparent by the hand of the following figures.

Data demonstrating that tPA-S$^{481}$A binds to plasminogen only in presence of fibrin. tPA-S$^{481}$A was incubated with plasminogen (100 nM each) and fibrin in the absence (Lane 2) or presence (Lane 3) of 1 μM uPA and in the absence of fibrin (Lane 5) compared to a positive control (80 nM human tPA-S$^{481}$A) (Lane 4). Complexes were immunoprecipitated with anti-plasminogen and detected with anti-tPA antibodies, as reported. The results demonstrate that no complexes were formed in the absence of fibrin (Lane 5). tPA-S$^{481}$A binded to plasminogen and formed a stable complex (Lane 2) only in the presence of fibrin. Binding of tPA-S$^{481}$A was inhibited by uPA (Lane 3).

FIGS. 2A-2D: Inhibition of plasminogen activation by tPA$^{S481A}$ is dependent on plasminogen conformation FIG. 2A. demonstrates lysis of plasma clots. tPA-S$^{481}$A (50 nM) inhibited lysis of human plasma derived clots by WT-tPA (20 nM) and uPA (50 nM), performed as previously reported.

Figure 2A:
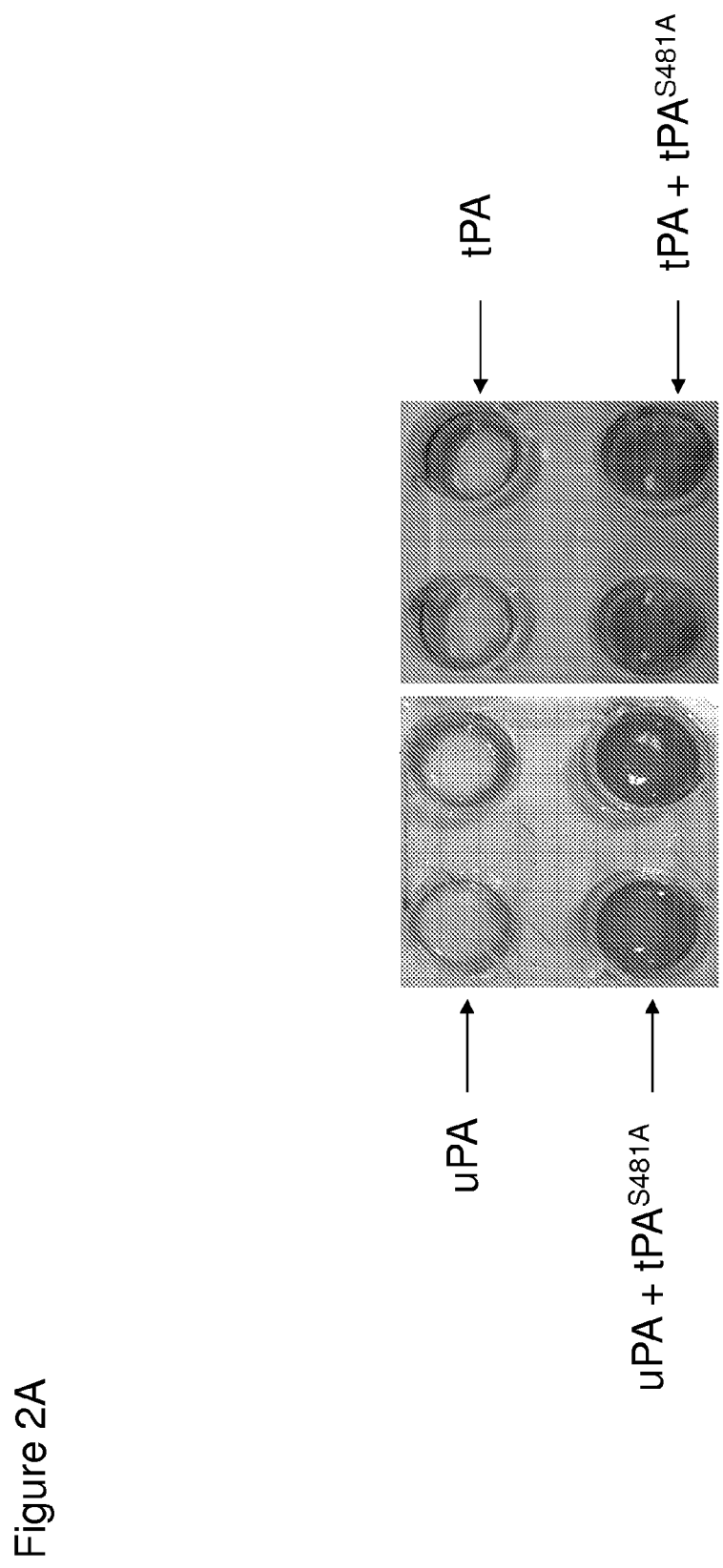
Figure 2B:
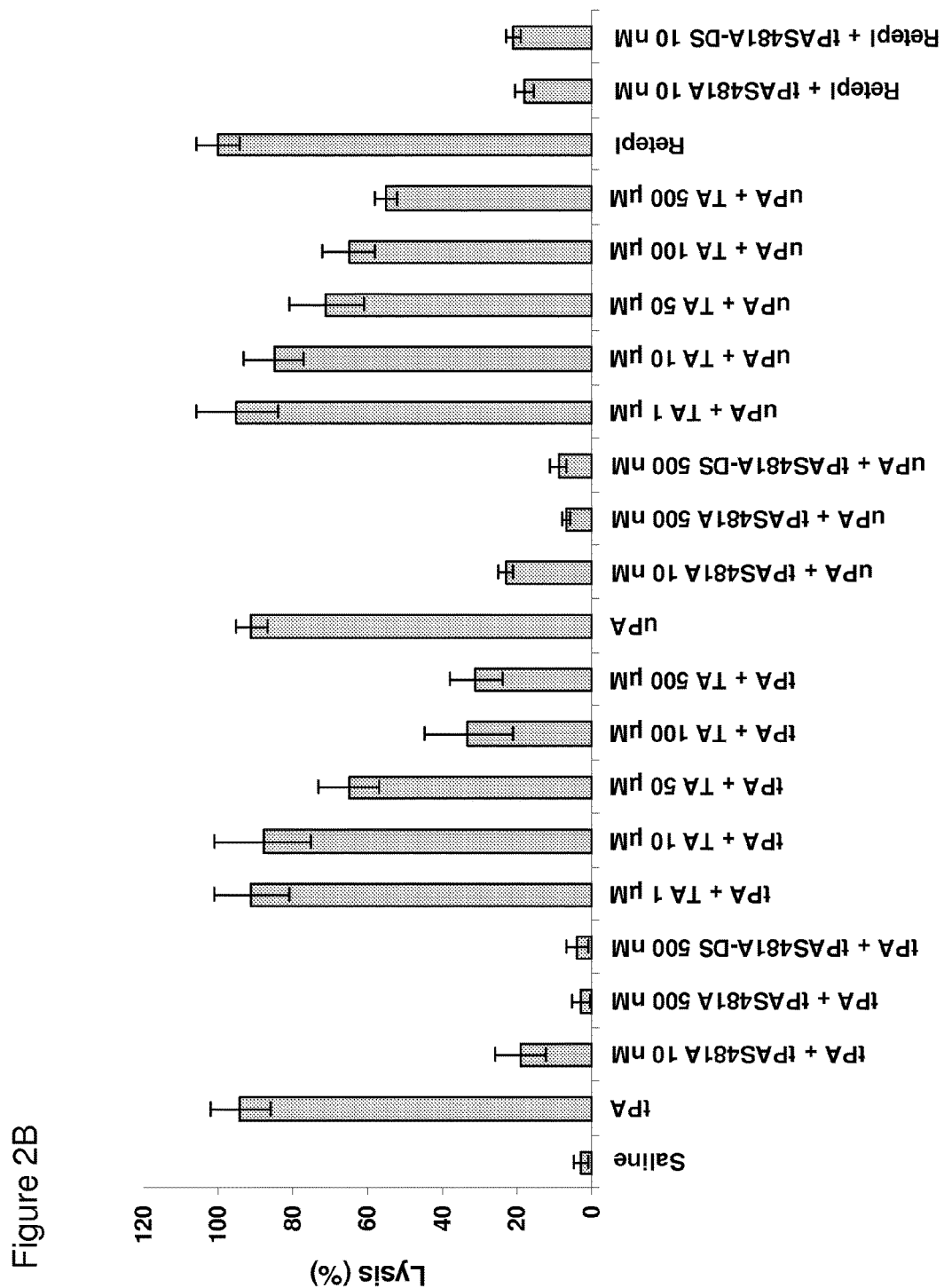

FIG. 2B. demonstrates that the two tPA mutants, tPA-S$^{481}$A and tPA-S$^{481}$A-DS inhibited tPA and uPA mediated lysis of clots derived from human plasma performed as in FIG. 2A. In another set of experiments reteplase (20 nM) was added instead of WT tPA±tPA-S$^{481}$A or tPA-S$^{481}$A-DS (10 nM).

Figure 2C:
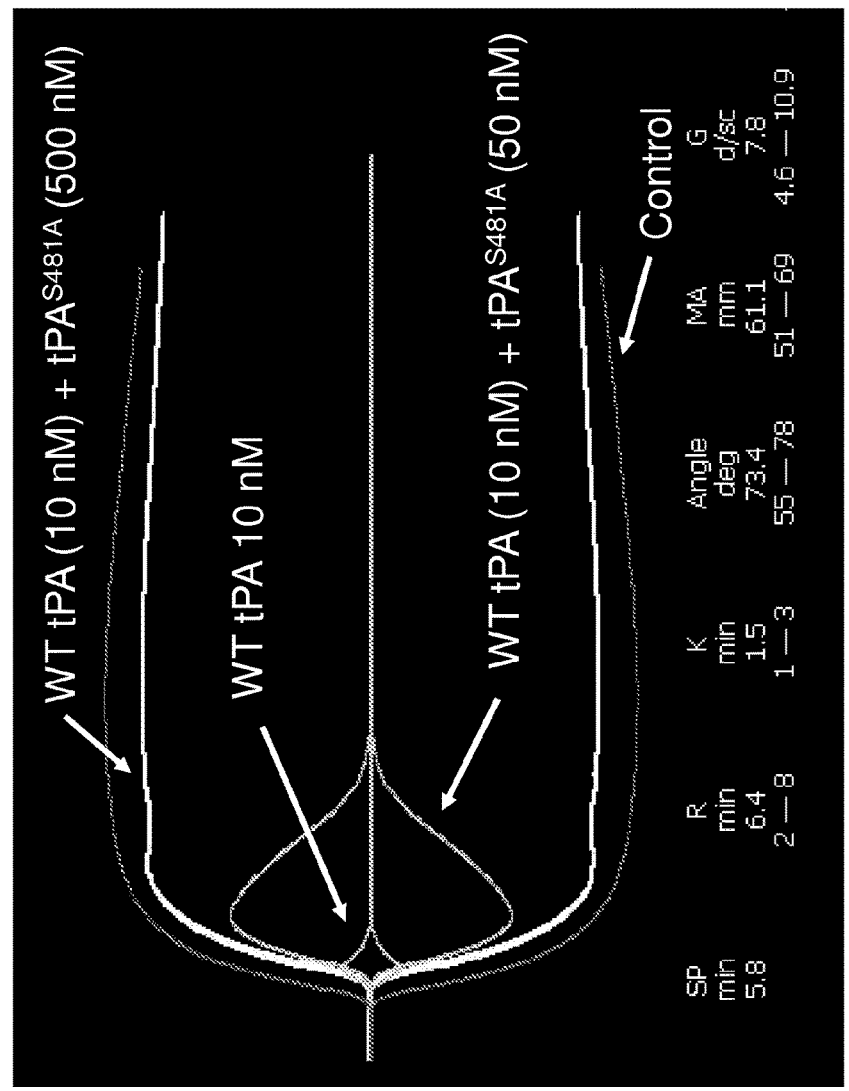

FIG. 2C. demonstrates clot lysis monitored by thromboelastography (TEG. tPA-S$^{481}$A inhibited lysis of clots derived from fresh whole human blood monitored by TEG. The experiments in panels B and C were performed, as indicated, without additives (Control), in the presence of WT tPA or uPA (10 nM each)±50 or 500 nM tPA-S$^{481}$A or tPA-S$^{481}$A-DS (50 nM).

Figure 2D:
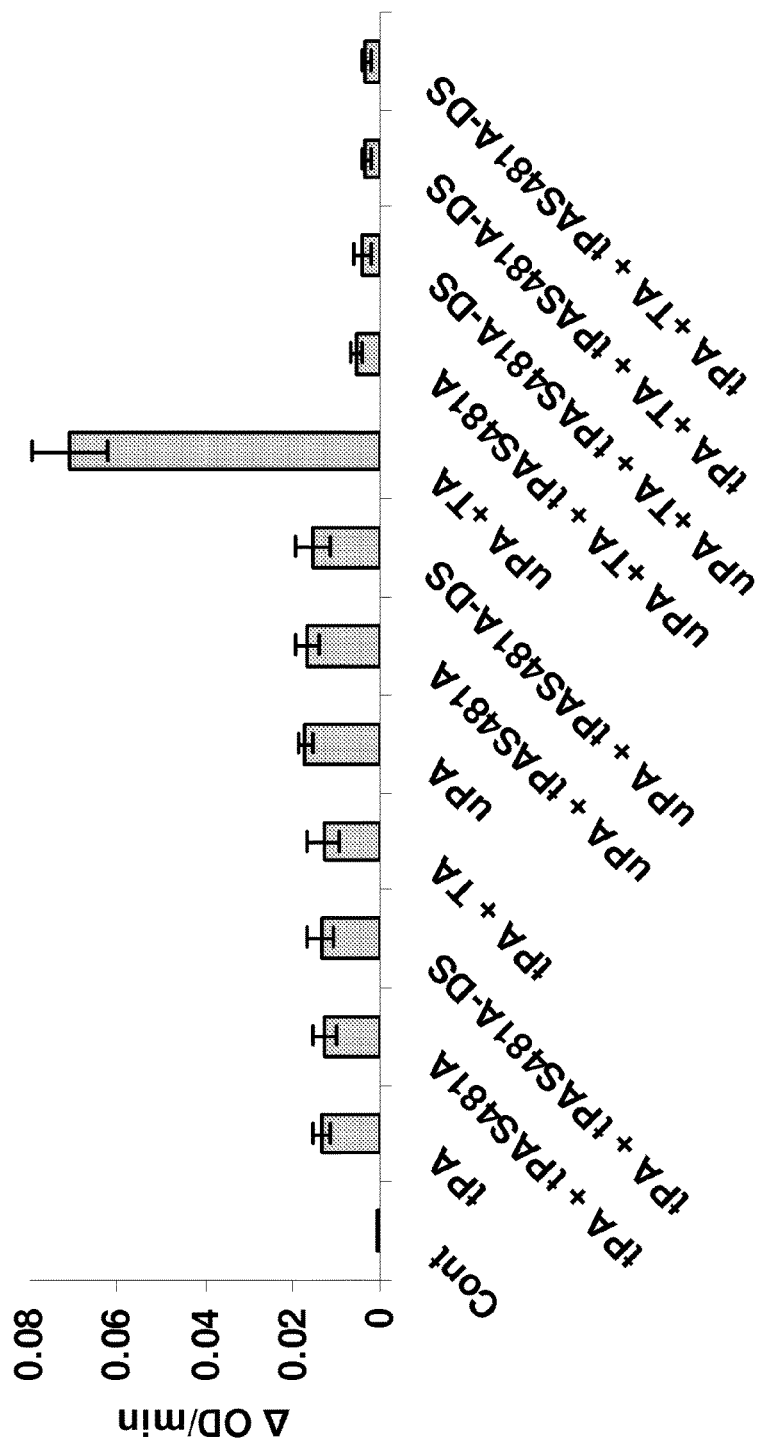

FIG. 2D. shows the effect of tPA-S$^{481}$A on plasminogen activator activity of tPA and uPA in the absence of fibrin. Plasminogen (500 nM) was incubated without (control) or with WT-tPA (50 nM) or uPA (20 nM) in the absence or presence of tPA-S$^{481}$A or tPA-S$^{481}$A-DS (100 nM), or tranexamic acid (TA) (200 nM) and a plasmin chromogenic substrate (100 μM). The OD at 405 nm was measured continuously over the next 20 minutes. In another set of experiments, TA was added together with tPA-S$^{481}$A (100 nM). The data are expressed as the change in OD per minute. The results demonstrate that tPA-S$^{481}$A had no effect on plasminogen activation by tPA or uPA in the absence of fibrin and that TA mimics the effect of fibrin only in the case of uPA.

FIGS. 3A-3F: CHI in mice induces time dependent expansion of intracerebral hemorrhage Intracerebral hemorrhage induced by CHI was evaluated by MRI and by measuring extravasation of hemoglobin (Hgb).

Figure 3A:
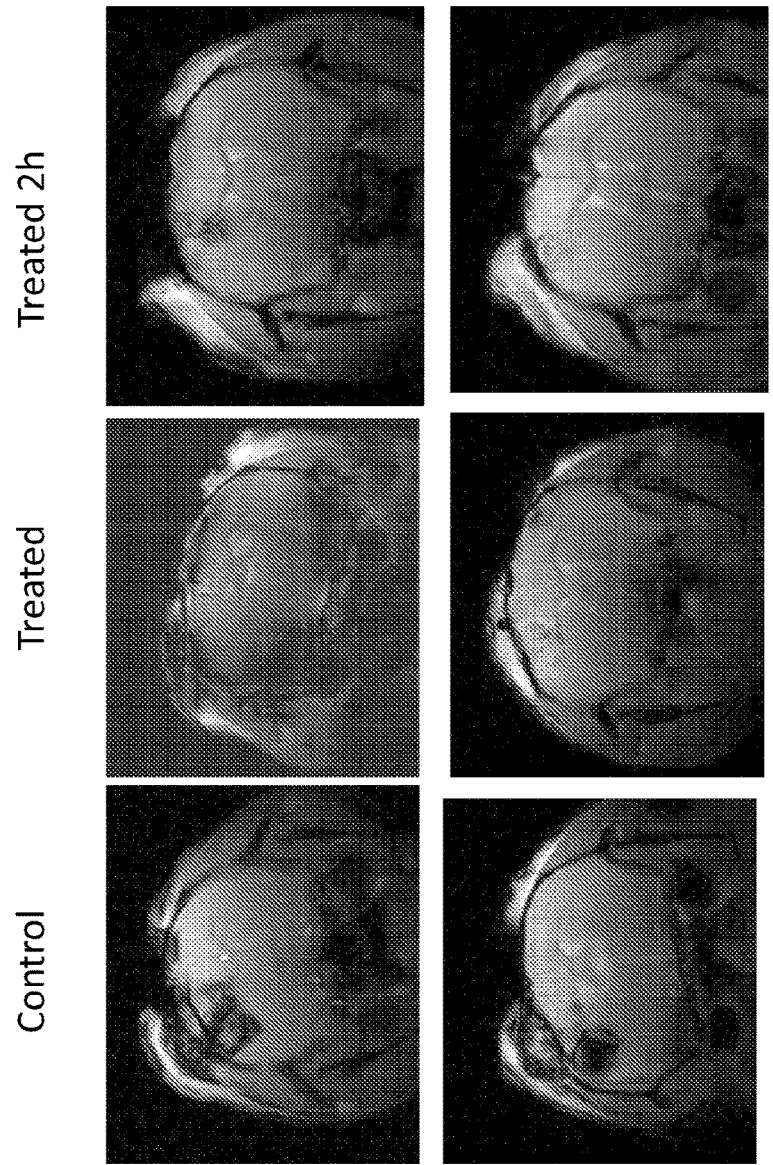

FIG. 3A. shows the hemorrhagic area 24 hrs post CHI in untreated WT mice (Control), mice were given tPA-S$^{481}$A or tPA-S$^{481}$A-DS (1 mg/kg each) immediately after CHI (Treated) or 2 hrs later (Treated 2 hrs). Two representative mice from each group (n=6) are shown in the top and bottom panels.

Figure 3B:
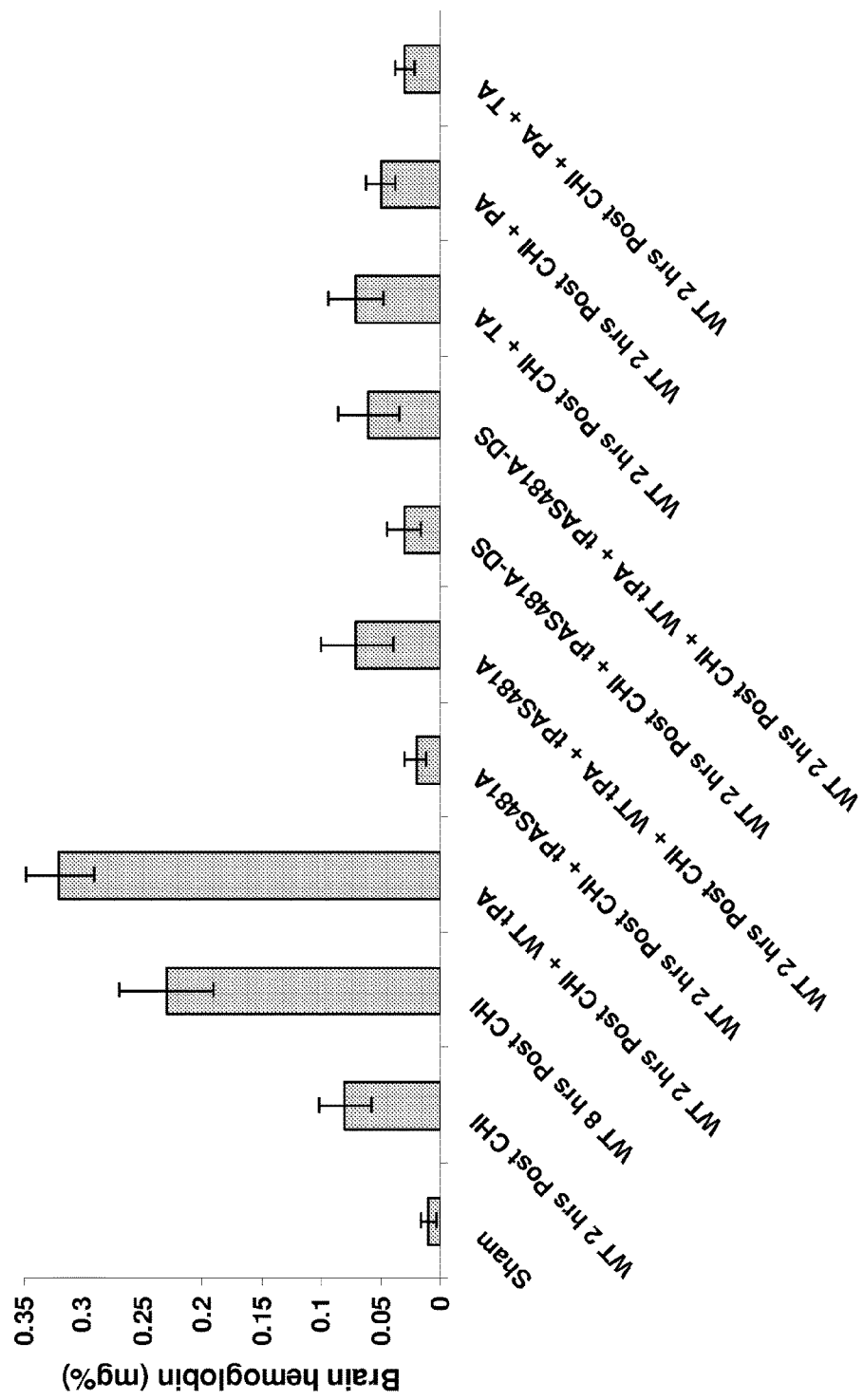

FIG. 3B. shows extravasation of Hgb as quantified by spectrophotometry at 2 or 8 hrs post CHI in WT and tPA$^{-/-}$ mice given saline, and WT or tPA-S$^{481}$A immediately post-injury. The results demonstrate that extravasation of Hgb was time dependent, more severe at 8 hrs, exacerbated by WT tPA and inhibited by tPA-S$^{481}$A (1 mg/kg each).

Figure 3C:
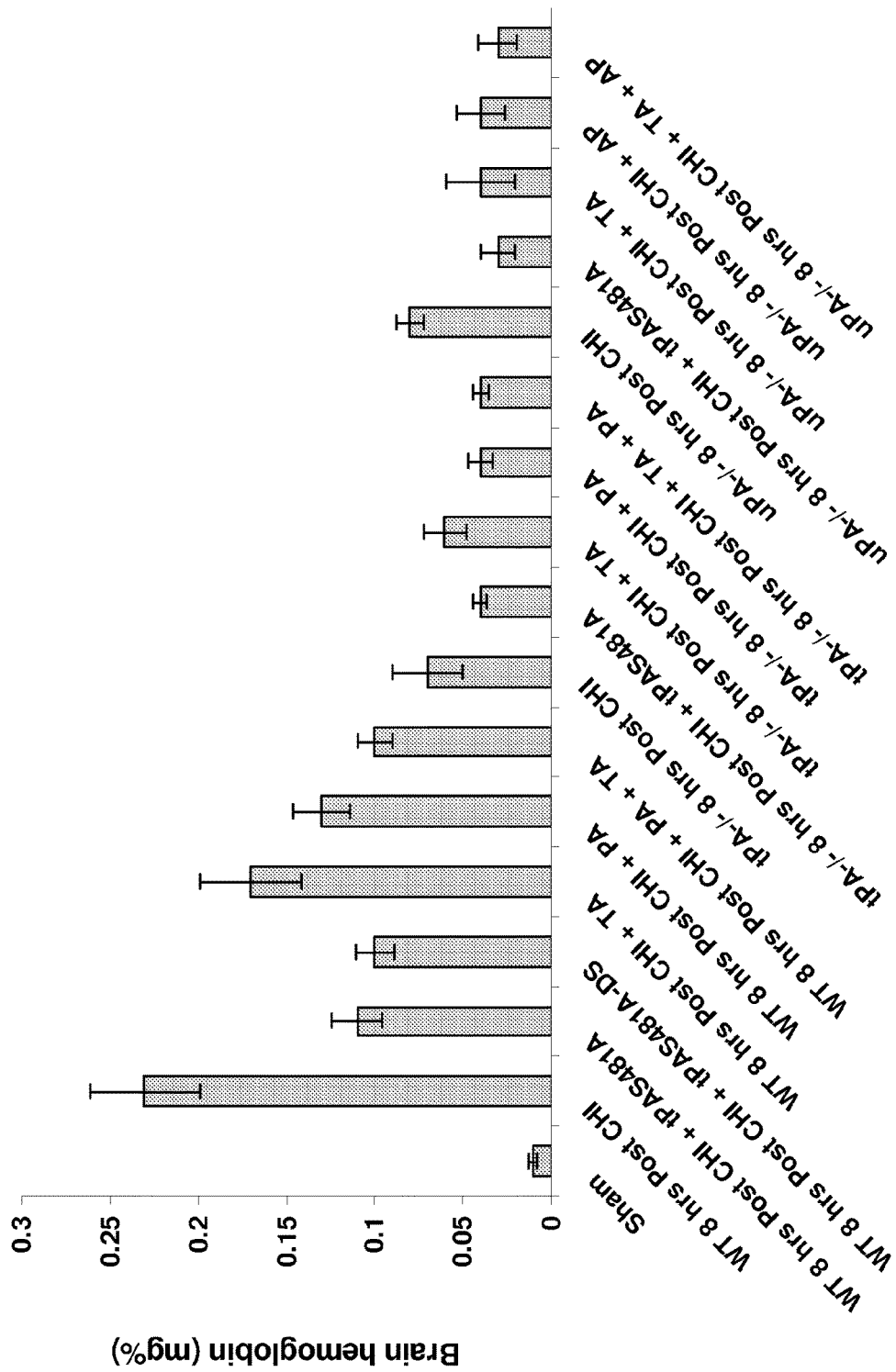

FIG. 3C. shows extravasation of Hgb at 2 or 8 hrs post CHI in WT and tPA$^{-/-}$ and uPA$^{-/-}$ mice. The experiments were performed as in FIG. 3B.

Figure 3D:
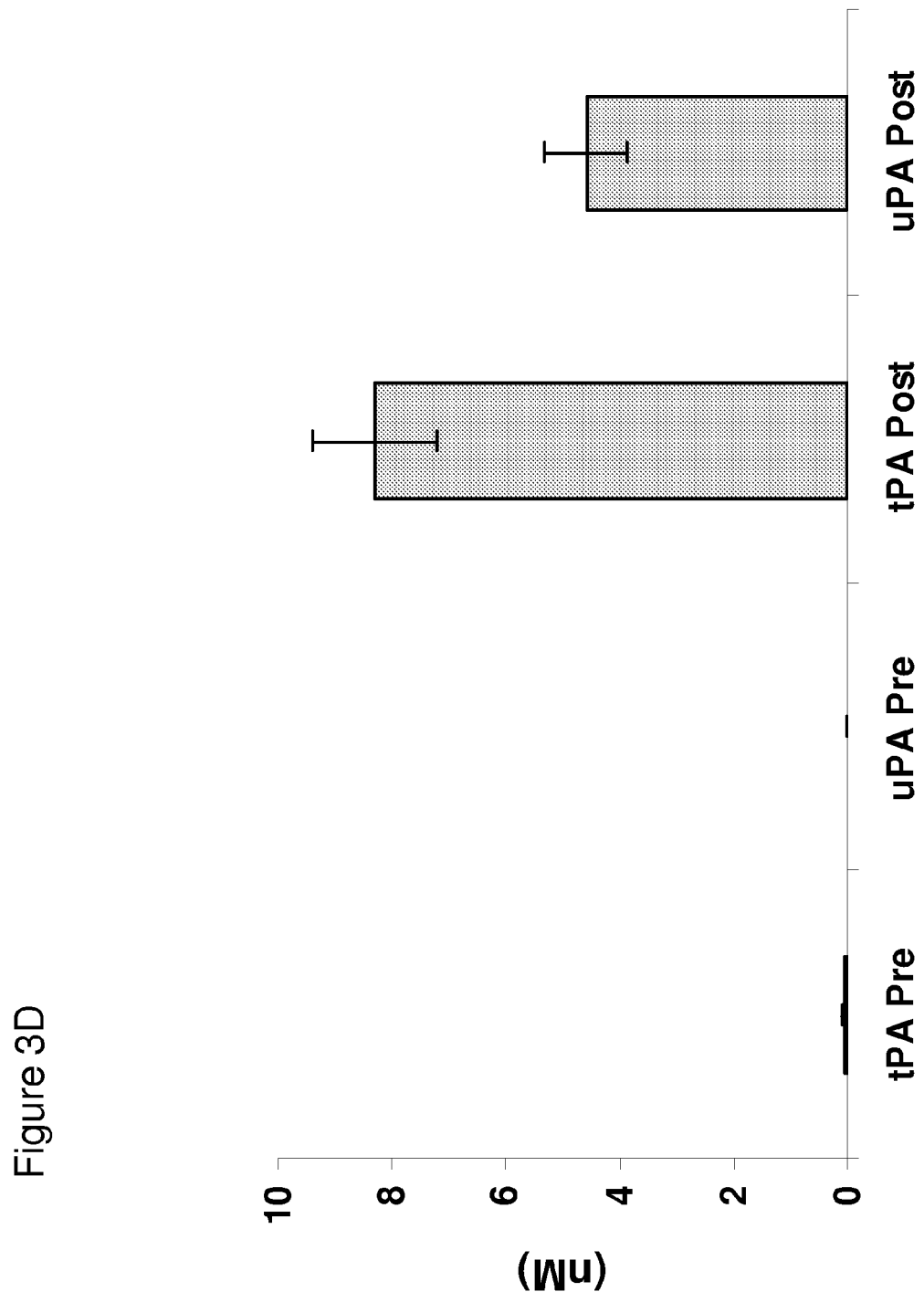

FIG. 3D. shows concentrations of tPA and uPA in the CSF of WT mice as determined by ELISA before (Pre) or 2 hours after (Post) CHI.

Figure 3E:
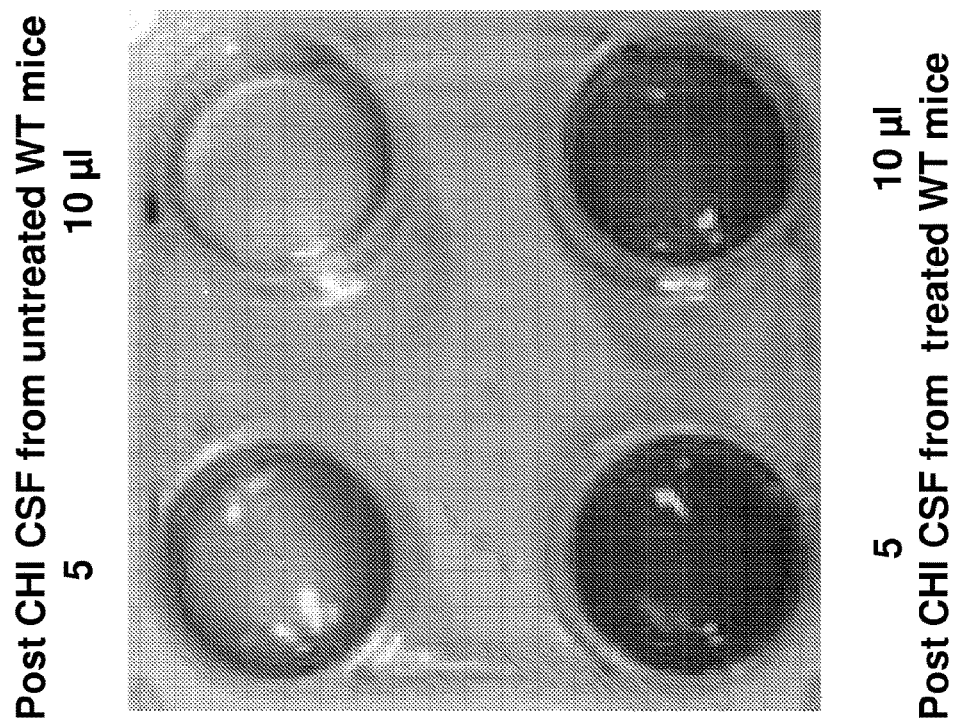

FIG. 3E. shows the fibrinolytic activity of the CSF post CHI. The upper lane shows CSF (5 or 10 μl) obtained 2 hours after CHI from untreated mice was placed on top of plasma derived clots as in FIG. 2A. The lower lane—CSF obtained 2 hours after CHI from mice treated with tPA-S$^{481}$A (1 mg/kg).

Figure 3F:
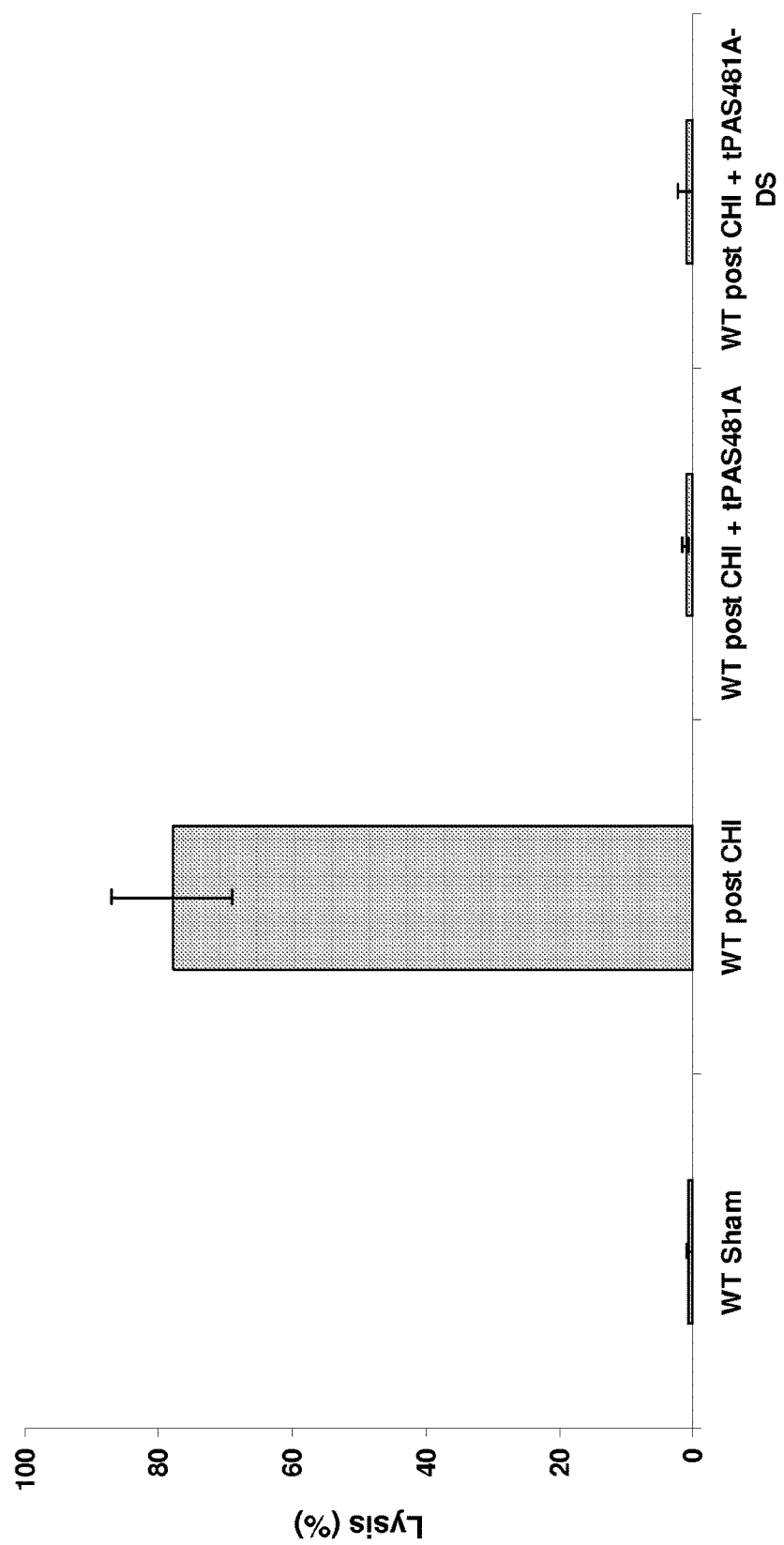

FIG. 3F. shows the fibrinolytic activity of CSF taken after CHI from untreated or mice given tPA-S$^{481}$A (1 mg/kg), quantified as in FIG. 2B.

Figure 4A:
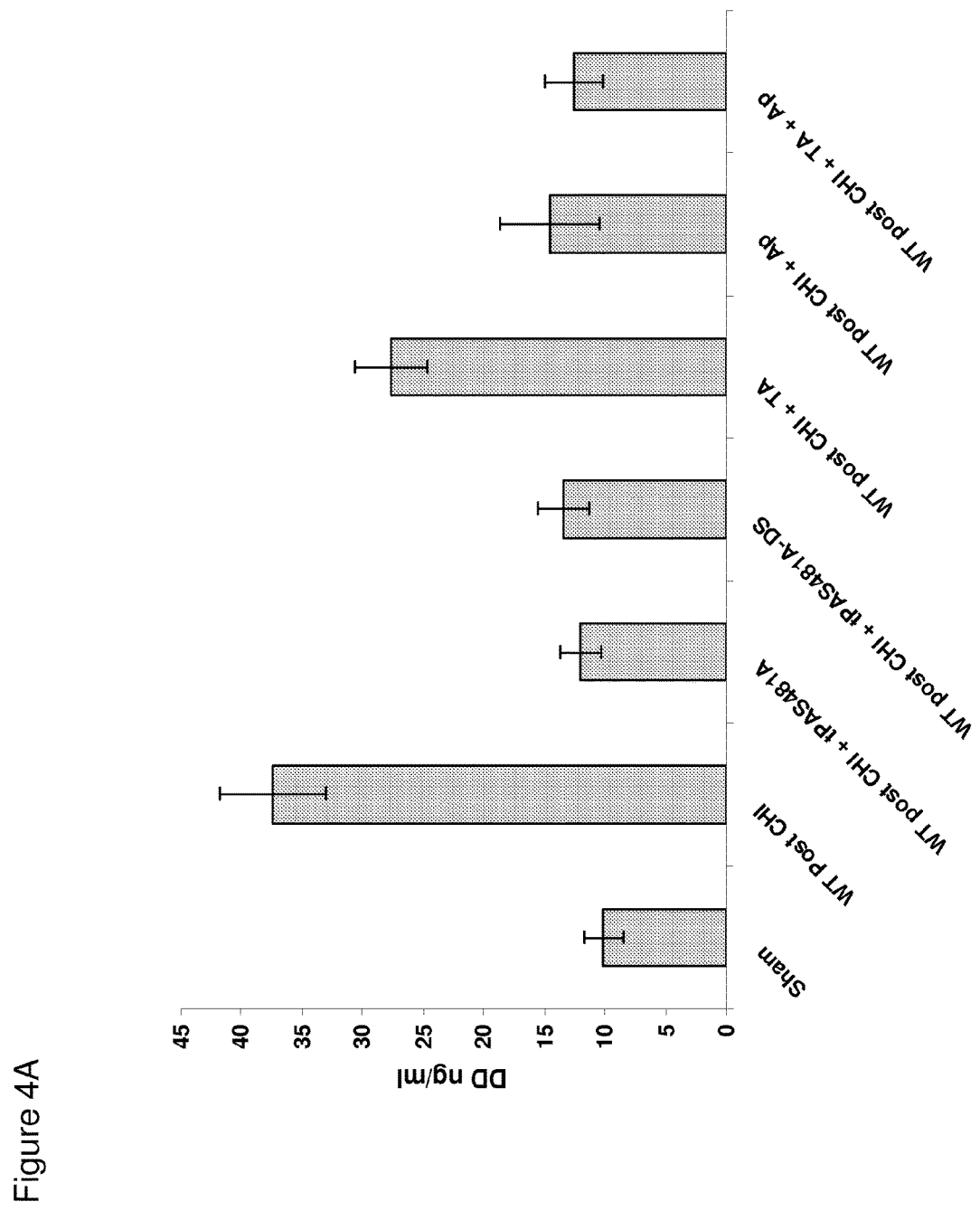
Figure 4B:
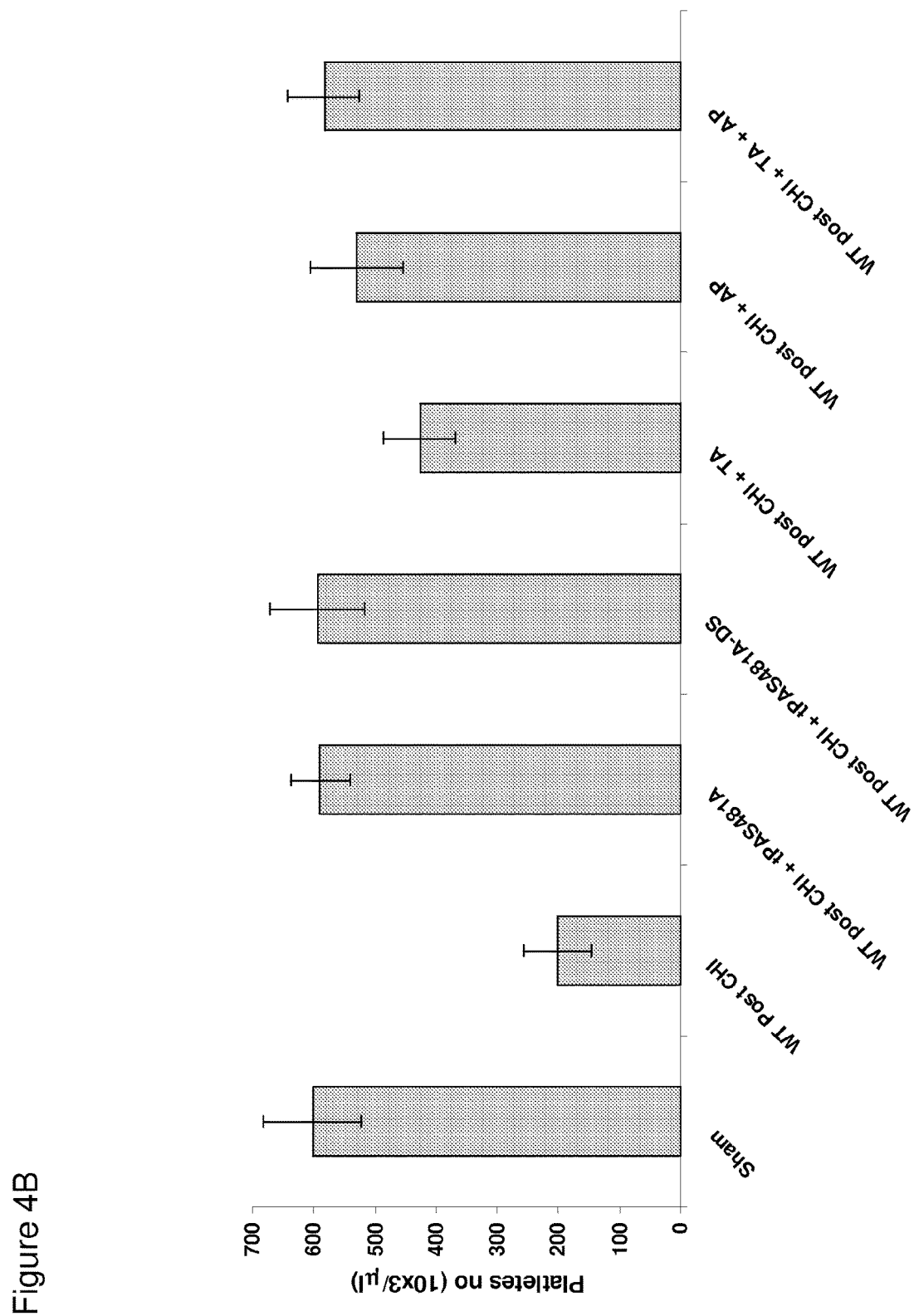

FIGS. 4A-4B: Effect of tPA-S$^{481}$A on coagulopathy:

Saline or saline containing tPA-S$^{481}$A (1 mg/kg), tranexamic acid (TA) (150 mg/kg), aprotonin (1 mg/kg) or TA+tPA-S$^{481}$A were administered intravenously (IV) immediately after CHI. Plasma levels of d-Dimers (DDs) and platelet counts were measured 2 hours later.

FIG. 4A. shows that tPA-S$^{481}$A inhibited the formation of d-Dimers

Figure 5:
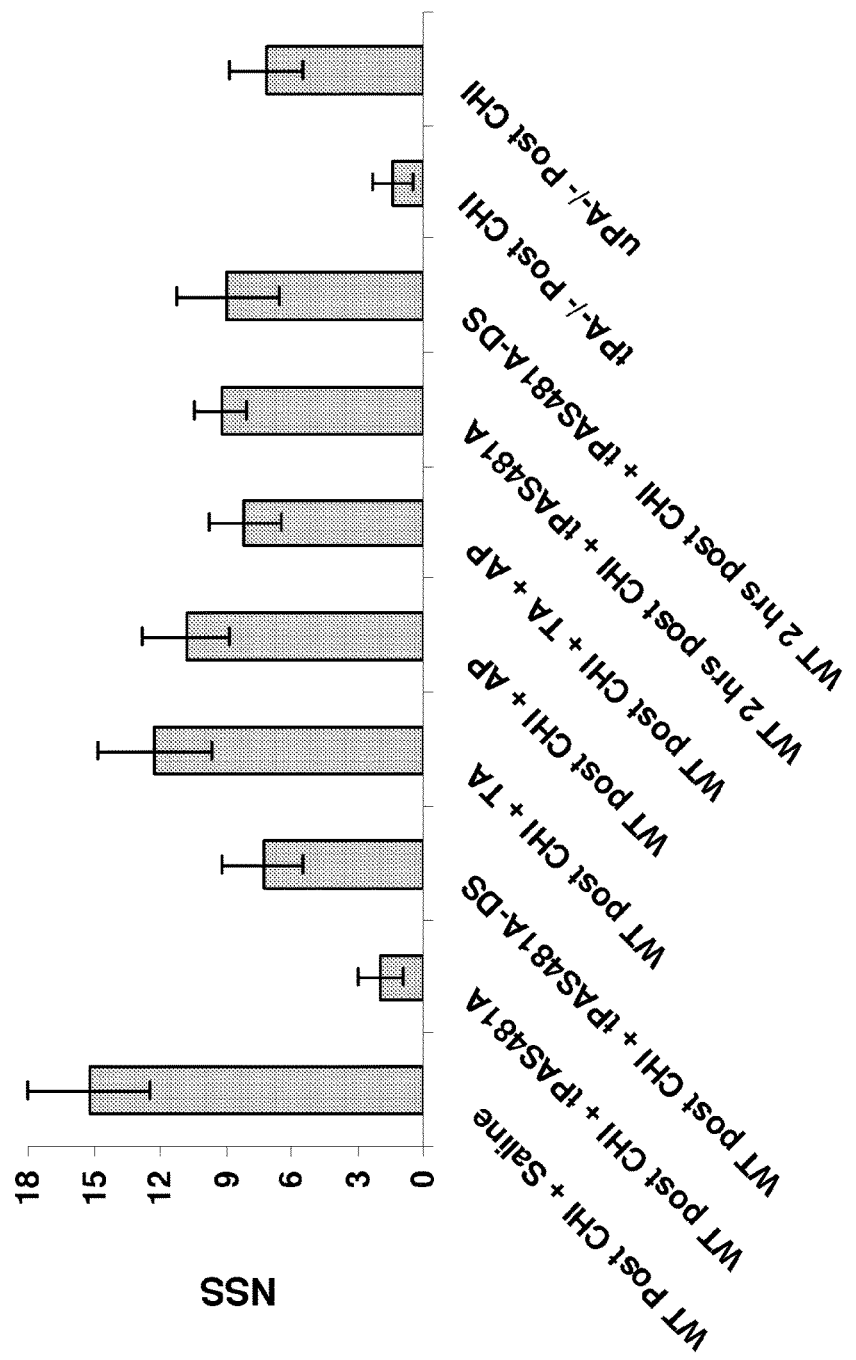

FIG. 4B. shows that tPA-S$^{481}$A inhibited the development of thrombocytopenia FIG. 5: Effect of tPA-$S^{481}$A on post CHI neurological recovery.

Saline or saline containing tPA-$S^{481}$A or tPA-$S^{481}$A-DS (1 mg/kg each), TA (150 mg/kg), aprotonin (AP) (1 mg/kg) or TA+tPA-$S^{481}$A was administered IV immediately after CHI. The neurological severity score (NSS) was determined 24 hours later.

Figure 6A:
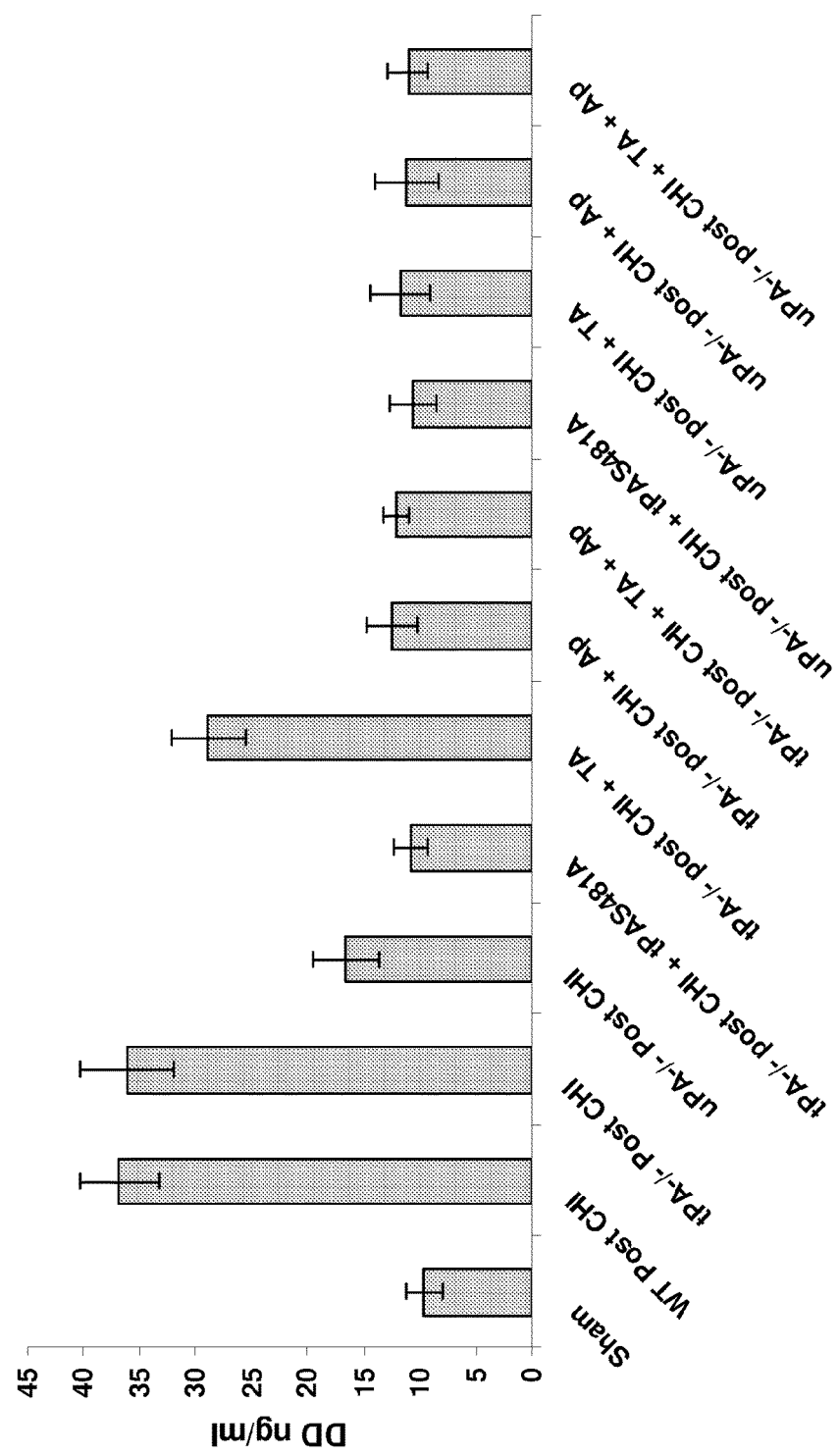
Figure 6B:
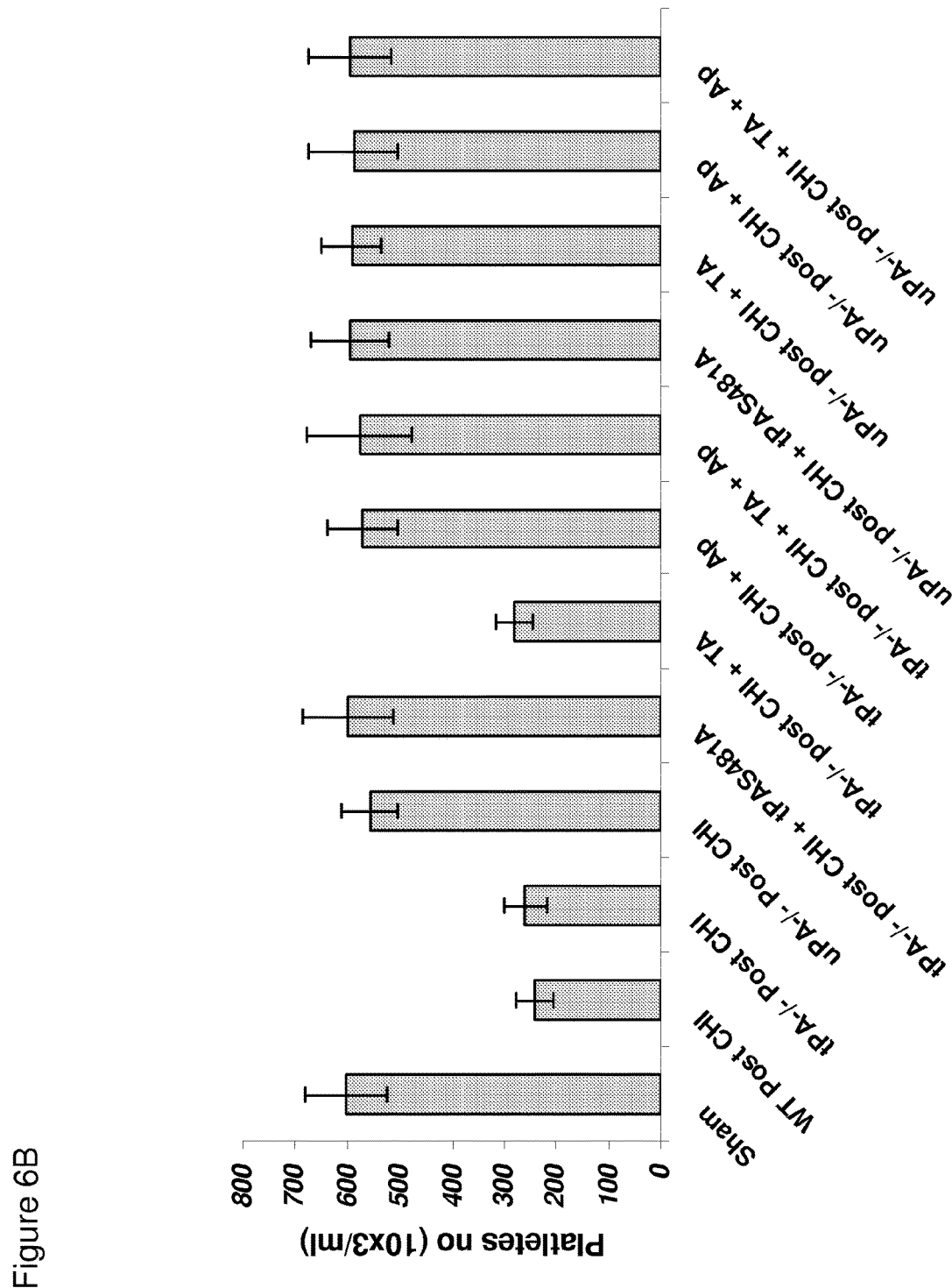
Figure 6C:
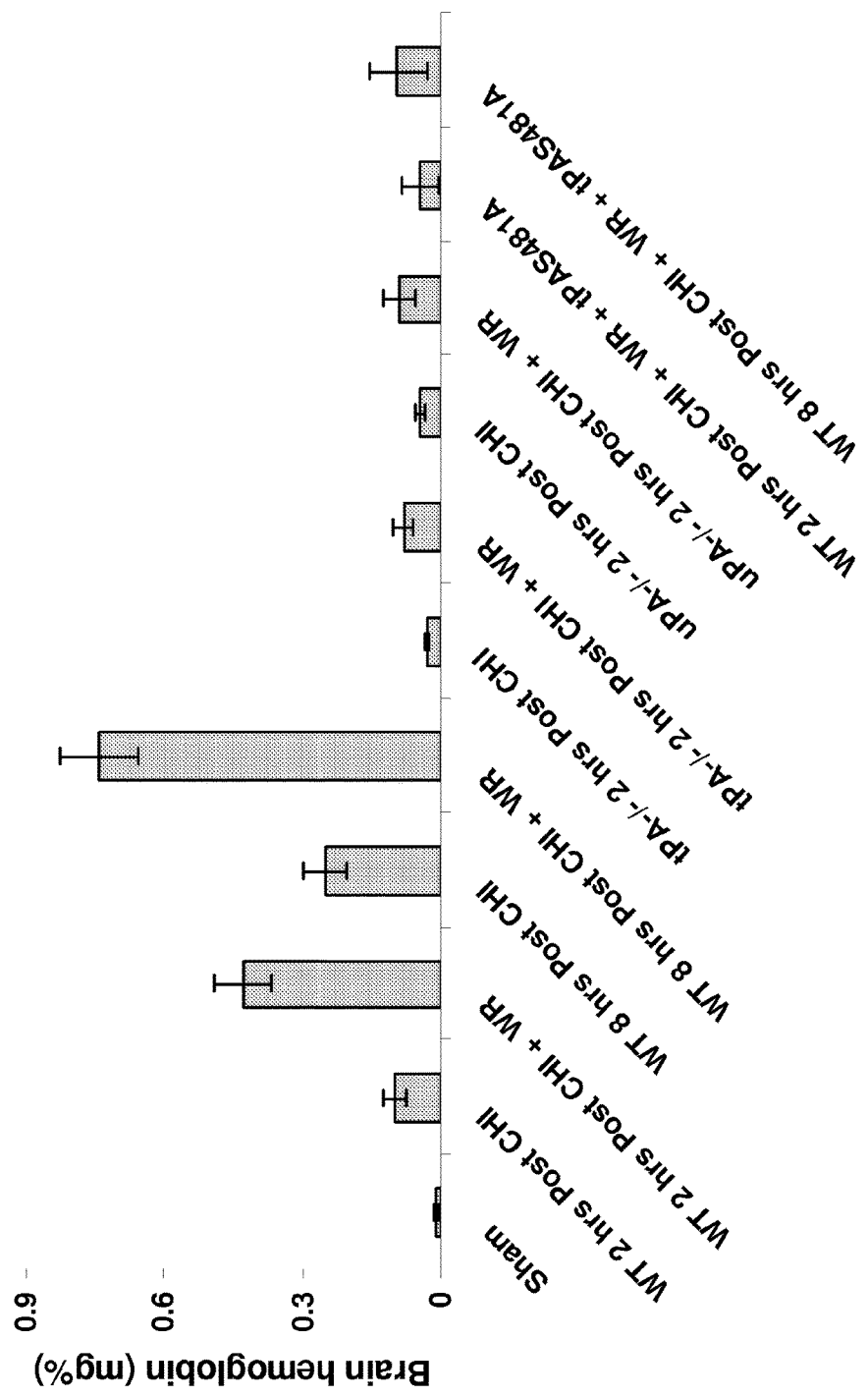

FIGS. 6A-6C: Role of endogenous tPA, uPA and tPA-$S^{481}$A on the development of intracerebral hemorrhage, d-Dimers and platelet counts post CHI.

CHI was induced in WT, $tPA^{-/-}$ and $uPA^{-/-}$ mice. The mice were treated IV with tPA-$S^{481}$A (1 mg/kg), TA (10 mg/kg) or AP (1 mg/kg) immediately after the CHI. Plasma levels of d-Dimers (DDs) were determined as in FIG. 4 and platelet counts were measured 2 hours later.

FIG. 6A shows the effect of the above treatments on DD levels

FIG. 6B. shows the effect of above treatments on platelet counts

FIG. 6C shows the inhibitory effect of tPA-$S^{481}$A on ICH expansion in mice treated with Coumadin (warfarin). CHI was induced in WT, tPA-/- or uPA-/- mice treated with Coumadin (WR) and INR of 2.5 at the time of trauma. tPA-$S^{481}$A (1 mg/kg) was given immediately after the TBI and brain hemoglobin was determined at 2 or 8 hrs, as indicated, after the injury. The results demonstrate that injection of tPA-$S^{481}$A to WT mice anticoagulated with warfarin almost totally inhibited the post-traumatic intracerebral hemorrhage. Furthermore, the data further support the concept that uPA and tPA contribute almost equally to post traumatic bleeding.

DETAILED DESCRIPTION OF THE INVENTION

It is to be understood that the invention is not limited in its application to the details set forth in the following description or illustrated in the drawings. The invention is capable of other embodiments or of being practiced out in various ways. Also, it is to be understood that the phraseology and terminology employed herein is for the purpose of description and should not be regarded as limiting.

When tissue is first wounded, blood comes in contact with collagen, triggering blood platelets to begin secreting inflammatory factors. Platelets also express glycoproteins on their cell membranes that allow them to stick to one another and to aggregate, forming a mass.

Fibrin and fibronectin cross-link together and form a plug that traps proteins and particles and prevents further blood loss. This fibrin-fibronectin plug is also the main structural support for the wound until collagen is deposited. Migratory cells use this plug as a matrix to crawl across, and platelets adhere to it and secrete factors. The clot is eventually lysed in a process called fibrinolysis and replaced with granulation tissue and then later with collagen.

Fibrinolysis is a process that prevents blood clots from growing and becoming problematic. This process has two types: primary fibrinolysis and secondary fibrinolysis. The primary type is a normal body process, whereas secondary fibrinolysis is the breakdown of clots due to a medicine, a medical disorder, or some other cause. In fibrinolysis, a fibrin clot, the product of coagulation, is broken down. Its main enzyme, plasmin, cuts the fibrin mesh at various places, leading to the production of circulating fragments, i.e. soluble fibrin degradation products (SFDP), that are cleared by other proteases or by the kidney and liver.

Plasmin is produced in an inactive form (proenzyme), plasminogen, in the liver. The tissue plasminogen activator (tPA) and urokinase plasminogen activator (uPA) are multi functional serine proteases (Nassar T et al, JBC 2002, 277:40499-40504; Nassar T et al, Blood 2004, 106:897-902) that, among others, cleave a single peptide bond between the amino acid residues $Arg^{560}$-$Val^{561}$ in the pro-enzyme plasminogen thereby producing a potent proteolytic enzyme-plasmin. Efficient activation of plasminogen depends on its binding to fibrin, which in turn dramatically stimulates tPA and uPA activation of plasminogen.

Endogenous Fibrinolysis.

Although endogenous fibrinolysis by uPA and tPA are each stimulated dramatically by fibrin, the mechanisms by which their activities are enhanced differ. In the case of tPA, fibrinolysis is initiated by binding and co-localization of tPA and the pro-enzyme plasminogen on the surface of fibrin, which increases the local concentrations of the two reactants. On the fibrin clot surface, tPA cleaves the $Arg^{560}$-$Val^{561}$ bond in plasminogen to generate plasmin, which then cleaves fibrin into diverse degradation products (SFDP), activates/inactivates and promotes the clearance of activated coagulation factors and activates platelets activation by cleaving certain glycoproteins off the surface of platelets. uPA also cleaves plasminogen to plasmin on the fibrin surface but without binding to fibrin. Plasminogen binds to N-terminal lysine residues on fibrin through its lysine binding sites (LBS) found the kringles 1-3. Plasminogen undergoes a conformational change once it binds to fibrin through its LBS, which makes it a better substrate for uPA. It is will documented that the change in plasminogen conformation induced by fibrin has no effect on its activation by tPA.

Lysine analogs such as tranexamic acid (TA) and Epsilon-amino caproic acid (EACA) have been used extensively as anti-fibrinolytics to prevent bleeding based on the assumption that tPA is the principal plasminogen activator in the circulation. However, uPA compensates for genetic deletion of tPA and contributes to fibrinolysis in the circulation. Tranexamic acid and Epsilon-amino caproic acid (EACA) bind to the LBS of plasminogen and thereby inhibit its binding to fibrin and its activation by tPA. On the other hand, binding of lysine analogs to plasminogen mimics the effect of fibrin and enhances its activation by uPA. Based on these principles, it would be expected that lysine analogs might enhance generation of plasmin in a fibrin-independent mode. Plasmin not formed on fibrin has greater opportunities to act on coagulation factors and platelets. Furthermore, plasmin generated in presence of lysine analogs is protected from inactivation by its physiological in inhibitor α2-antiplasmin, which would also enhance a fact that would increase potential undesired effects.

Our data show for the first time that binding of plasminogen to fibrin or to lysine analogs, enhances its interaction with tPA-$S^{481}$A and thereby facilitate its inhibition of tPA- and uPA-mediated fibrinolysis. Thus, in theory in theory $tPA^{481}$A would be expected to be a more potent inhibitor tranexamic acid and Epsilon-amino caproic acid because it acts directly on the lytic step irrespective of mechanism.

Further, affinity of plasminogen to fibrin allows it to be incorporated into the clot during clot formation, thus enabling on-site activation of tPA and uPA fibrinolysis when needed. In vivo, tPA is slowly released into the blood by the damaged endothelium of blood vessels, such that, after the bleeding has stopped, plasminogen entrapped within the clot is slowly activated by tPA and uPA leading to breaking down of the fibrin mesh and production of SFDP.

As the fibrinolysis process is fundamental to vitality of the whole organism, it is subjected to tight regulation and feed-back control. Plasmin may further stimulate plasmin production as being in itself the catalizator of production of both, tPA and uPA, more active forms. Plasmin, among others, is responsible for cleavage of the single polypeptide chain form of tPA at the $Arg^{275}$-$Ile^{276}$ residues and thereby production of the disulfide-linked two-chain form of tPA. In the same way, plasmin is also responsible for cleavage and activation of the prouPA known also as single chine uPA (scuPA) to the fully active two chain uPA (tPA). Furthermore, plasmin cleaves the two chain uPA known also as high molecular weight (HMW) uPA at the $Lys^{158}$-$Ile^{159}$ residues to the low molecular weight (LMW) proteolytically active uPA lacking binding to the uPA receptor.

In contrast, tPA and uPA are inhibited by the endogenous plasminogen activator inhibitors 1 and 2 (PAI-1 and PAI-2). PAI-1 is also produced by the blood vessels endothelium and by other tissue types, such as adipose tissue. PAI-2 is present only at detectable quantities in blood during pregnancy, as it is produced by the placenta, which may explain the increased rate of thrombosis during pregnancy.

Inhibition or reduction of fibrinolytic activity is particularly important during surgery and trauma in order to control excessive bleeding (i.e. hemorrhages). It is moreover imperative for patients with inherited (i.e. congenital) coagulopathies, such as von Willebrand disease (VWD), hemophilia A and B, in order to counterbalance the decrease procoagulant state. To reciprocate these needs, a number of synthetic fibrinolytic inhibitors (also antifybrinolytics) have been developed, of which today the only available products are the epsilon-aminocaproic acid (EACA) and the more potent tranexamic acid (TA or AMCA). Use of both these products, however, is associated with considerable gastrointestinal adverse events. In addition, the naturally occurring antifibrinolytic agent aprotinin was withdrawn from market after identification of major adverse effects, especially in the kidney.

Thus, the present invention answers a pressing need for new antifybrinolytic products, especially since use of natural blood products, such as fresh or frozen plasma, is significantly jeopardized by risks of infections or anaphylactic reactions.

The present invention is based on unexpected and important findings that certain catalytically inactive tPA variants produced by a specific point mutation or mutations are capable bind directly to plasminogen in presence of fibrin or lysine analogs and by that to inhibit tPA- and uPA mediated plasminogen activation and the subsequent fibrinolysis in vitro and in vivo. Specifically, the inventors found that catalytically inactive tPA variant produced by substitution of the $Ser^{481}$ residue to Ala at the catalytic site of tPA ($tPA^{Ser481Ala}$; SEQ ID NO:1) competes with the Wild type (WT) tPA and uPA in terms of affinity to plasminogen in presence of fibrin and thereby interferes with the tPA- and uPA mediated fibrinolysis. Moreover, the inventors further showed (FIG. 2B) that $tPA^{Ser481Ala}$ inhibit the fibrinolysis induced by "reteplase", a tPA mutant having a decreased binding to fibrin, compared to WT tPA; indicating that $tPA^{Ser481Ala}$ inhibits fibrinolysis by preventing the binding of the plasminogen activators to plasmin present on the fibrin surface. More ever, the data presented in FIG. 2D show that $tPA^{Ser481Ala}$ inhibit plasminogen activation by tPA and uPA in absence of fibrin but in the presence of TA, supporting further our finding that $tPA^{Ser481Ala}$ exerts its inhibitory effect by binding to plasminogen modified by fibrin or lysine analogs. More surprisingly, the said tPA variant was found to compete with uPA and thereby uPA-mediated fibrinolysis in a specific dose-dependent manner that was highly dependent on the presence of fibrin (see Example 1). These experimental data have led the inventors to the notion that the $tPA^{Ser481Ala}$ variant and possibly certain other tPA mutants may be used for targeting tPA and uPA fibrinolysis.

This notion have proved to be correct in a series of experiments showing that another tPA variant comprising both the $Ser^{481}$-Ala mutation and additional point mutations in the tPA kringle domain, $KHRR^{299-302}$ to AAAA at the tPA molecule of SEQ ID NO. 7. It should be noted that such mutation is designated as DS. In certain embodiments, this mutant may comprise the amino acid sequence as also denoted by SEQ ID NO:2, and thereby lacking catalytic activity as well as capability of binding to the N-methyl-D-aspartate receptor (NMDA-R), has the same inhibitory effect on tPA and uPA fibrinolysis which is strictly dependent on the presence of fibrin (Example 1). It should be further noted that the invention further encompasses a double mutated tPA that carry both, the $^{S481A}$ and the $KHRR^{299-302}$ to AAAA mutation having the amino acid sequence as denoted by SEQ ID NO. 13. It should be noted that this mutant further comprises two additional amino acid residues at the N' terminus of the molecule. These two residues, Arg and Ser (RS), were introduces only for cloning purpose. It should be noted that the 299-302 mutation used herein also refers to a mutation known in the art as KHRR to AAAA of positions 296-299 of tPA.

Moreover, when comparing the anti-fibrinolytic effect of these variants to the synthetic fibrinolysis inhibitor TA, the inventors found that said variants are more potent fibrinolytic inhibitors than TA and that unlike TA, they are targeting both tPA and uPA fibrinolysis (Example 1). Taken together, these data have led to consolidation of an inventive concept, by which certain tPA mutants may have potential therapeutic utility of in inhibition of fibrinolysis and several other physiological processes related to tPA and uPA activity.

Further experiments in vivo in the mouse model of traumatic brain injury (TBI) demonstrated potential clinical utility of the above inventive concept (Example 2). The inventors found that administration of tPA variants immediately after, or 2 hours after head trauma leads to attenuation and significant reduction of bleeding (intracranial hemorrhage, ICH) consistent with significant reduction of fibrinolytic activity in the cerebrospinal fluid (CSF). More surprisingly, treatment with tPA variants was found to reverse secondary symptoms of TBI, such as thrombocytopenia and neurological symptoms, with no apparent side effects.

Thus, according to a first aspect the present invention relates to an anti fibrinolytic composition comprising at least one tPA (tissue plasminogen activator) mutant that carries a point mutation in position 481 of the Wild type molecule as denoted by SEQ ID NO: 7, substituting $Ser^{481}$ to Ala. More specifically, the mutant used for the composition of the invention inhibits the fibrinolytic activity of at least one of tPA and uPA (urokinase plasminogen activator).

In certain embodiments, the composition of the invention may further comprise at least one additional therapeutic agent.

In yet another embodiment, the composition of the invention may further comprises at least one expectable carrier and excipient. According to one of the embodiments, a composition of the invention comprises tPA variant designated $tPA^{Ser481Ala}$ comprising the amino acid sequence denoted by SEQ ID NO. 1, which was shown as an effective and specific inhibitor of tPA- and uPA-mediated plasminogen activation and fibrinolytic activity (Example 1). It should be further appreciated that the mutated tPA molecule of the invention may be also referred to as tPA-$S^{481}$A. It should be also noted that this mutant further comprises two additional amino acid residues at the N' terminus of the molecule. These two residues, Arg and Ser (RS), were introduces only for cloning purpose. Therefore, in certain embodiments, the tPA-$S^{481}$A mutant of the invention may comprise the amino acid sequence as denoted by SEQ ID NO. 12.

The present invention discloses compositions comprising a mutated tPA molecule that inhibits fibrinolytic activity of both, tPA and uPA. It should be appreciated that the term tPA used herein for the tissue plasminogen activator (also known as PLAT; enzyme entry EC 3.4.21.68) relates to a secreted serine protease that converts and activates the proenzyme plasminogen to a potent fibrinolytic enzyme plasmin. tPA is synthesized in vascular endothelial cells as a single polypeptide chain that undergoes proteolytic cleavage by plasmin or trypsin at a centrally located arginine-isoleucine bond, resulting in a 2-chain disulfide-linked form composed of the N-terminally derived heavy chain and the C-terminal light chain. The tPA gene (DNA acc. NT_167187.1 mapped to chr. 8p11.21) contains 14 exons encoding the heavy chain domain including two kringle regions (K1 and K2) and regions homologous to growth factors and the light chain domain comprising the serine protease catalytic site. Alternative splicing of the tPA gene results in multiple transcript variants encoding different isoforms taking part in multiple biological processes, apart from fibrinolysis, such as cell migration and tissue remodeling. Increased tPA activity causes hyperfibrinolysis manifested as excessive bleeding; decreased tPA activity leads to hypofibrinolysis which can result in thrombosis or embolism. tPA linked phenotypes include familial hyperfibrinolysis (due to increased tPA release) and familial thrombophilia (due to decreased tPA release (OMIM num. 612348).

Further, the term uPA used herein for the urinary plasminogen activator (also known as PLAU; EC 3.4.21.73) relates to another enzyme that converts plasminogen to plasmin. uPA may occur as a single-chain form (scuPA) or as a 2-chain derivative (also called HMW uPA) generated by cleavage of the single-chain form by plasmin. HMW uPA can be further processed into LMW uPA which is proteolytically active but does not bind to the uPA receptor. The uPA gene (Gene acc. NT_030059.13 mapped to chr. 10q22.2) produces several alternatively spliced transcript variants encoding different uPA isoforms. uPA is involved in degradation of the extracellular matrix and angiogenesis, and possibly tumor cell migration and proliferation. A specific polymorphism in this gene may be associated with late-onset Alzheimer's disease (OMIM num. 104300 and Quebec-patelet disorder (OMIM num. 601709).

As noted above, the mutant of the invention inhibits fibrinolytic activity of tPA and uPA. The term fibrinolysis used herein in relation to the invention denotes a physiological process wherein blood clots are dissolved. The reaction in fibrinolysis is the activation of the proenzyme plasminogen to plasmin, a serine protease responsible for degradation of fibrin clots and many other biological proteins. Plasminogen binds to fibrin via specific lysine binding sites (LBS) at the kringle domains. tPA, the physiological activator of plasminogen, also binds to fibrin via its finger domain and, to a lesser extent, by the second kringle domain. This co-localization of plasminogen and tPA further facilitates fibrinolysis at the site of the fibrin clot. Fibrinolysis is important for maintenance of homeostasis to enable accessibility of biological factors responsible for repair and regeneration (angiogenesis) of to the damaged blood vessels. Inhibition or reduction of fibrinolysis by fibrinolytic inhibitors is important in surgery and trauma to control blood loss and even more strongly indicated for patients with bleeding disorders The term "inhibition/reduction" as referred to herein, relates to retardation, attenuation, retraining or reduction of a process. More specifically, it is understood that the tPA mutants of the invention inhibit at least one of tPA and uPA fibrinolysis by at least about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In the same way, it is understood that the tPA mutants of the invention inhibit at least one of tPA- and uPA-dependent plasminogen activation by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

It should be noted that the term "mutation" referred to herein relates to induced genetic variations which have shown to alter function of the encoded protein product. Said mutations may be point mutations that are substitutions, deletions or insertions of a single nucleotide in the DNA sequence, or deletion/insertion mutations—changes in a number of nucleotides in the DNA sequence; or duplication mutations—abnormal repetitions of a DNA sequence compared to the Wild type sequence. It is well known in the art that point mutations may be missense mutations or nonsense mutation or frameshift mutations. In specific embodiments of the invention, the mutants of the invention carry at least one point mutation substituting or replacing a specific amino acid residue with another due to a point mutation in the codon encoding the specific amino acid residue.

The tPA enzyme, in addition to its catalytic domain that comprises serine protease, also contains the fibronectin-type 3 finger domain, epidermal growth factor-like domain and two kringle domains (K1 and K2). The finger domain finds fibrin and annexin II (a protein involved in diverse cellular processes such as cell matrix interactions, actin cytoskeleton interaction, cell motility, endocytosis and ion channel formation). The K1 and K2 domains bind to fibrin, the K2 is essential for the brain-protective activity of tPA. The catalytic domain, in addition to mediating the proteolytic function of tPA, also binds to vascular smooth muscle cells and mediates binding inhibitors such as (PAI-1 and PAI-2).

Mutations induced at a protein functional domain and consequent biological activity thereof is particularly relevant to the present invention, specifically in relation to the kringle, finger and other domains of the tPA enzyme. Therefore, it should be appreciated that the mutated tPA molecule of the invention may carry any additional point mutation in any domain of the molecule.

In another embodiment, the mutated tPA$^{S481A}$ molecule of the invention may carry in addition, a point mutation in the K domain (at least one of the K1 or K2). The term "kringle domain" (K) as referred herein relates to autonomous protein domains that fold into large loops stabilized by three disulfide linkages. K domains have been found for example in plasminogen, tPA, hepatocyte growth factors, prothrombin, and apolipoprotein(a). K domains are important in protein-protein interactions, most notably with blood coagulation factors.

In one embodiment, the mutated tPA$^{S481A}$ molecule of the invention may carry in addition, a point mutation in the F domain of the molecule. The term "finger domain" (F) as referred herein relates to small structural protein domains characterized by an amino acid motif comprising $Cys_3HisCys_4$, which binds two zinc cations that stabilize a particular finger-like folding of a protein. The finger domain name has now come to encompass a wide variety of differing protein structures, including the fibronectin-type 3 finger domain. Many proteins containing F domains play a key role in the ubiquitination pathway.

The above is particularly relevant to some embodiments of the invention, wherein the tPA Ser$^{481}$ to Ala mutant comprised in the composition of the invention further comprises at least one point mutation located at any position of residues Lys$^{296}$, His$^{297}$ Arg$^{298}$, Arg$^{299}$, Asp$^{120}$, Thr$^{106106}$, and/or a deletion of the tPA finger and K1 domains (also referred herein as double mutants). The invention also provides a tPA mutant completely deleted except for its finger domain, and optionally its K1 domain.

Thus, in more specific and non-limiting embodiments, the tPA$^{Ser481Ala}$ variant comprised within the composition of the invention may further comprise at least one of the following: (a) point mutations in positions 299-302 of the Wild type molecule as denoted by SEQ ID NO. 7, substituting KHRR$^{299-302}$ to AAAA; (b) point mutations in positions 120 and 106 of the Wild type molecule as denoted by SEQ ID NO. 7, substituting N$^{120}$ to Q and T$^{106106}$ to N; and (c) deletion of at least one of the finger and K1 domains, as denoted by SEQ ID NO. 4. Effectiveness of tPA double mutants have been demonstrated in vitro in terms of inhibitory effects on tPA- and uPA-mediated plasminogen activation and fibrinolysis (Example 1), as well as in vivo in terms of inhibition of pathologic fibrinolysis or hyperfibrinolysis and the inhibition of glutamate-mediated neural damage or death associated with neural trauma and especially head trauma (Example 2). It should be noted that the 299-302 mutation used herein also refers to a mutation known in the art as KHRR$^{299-302}$ to AAAA of positions 296-299 of Tpa, and the mutations substituting N$^{120}$ to Q and T$^{106106}$ to N, is also known in the art as mutation substituting N$^{117}$ to Q and T$^{103}$ to N.

The above is particularly relevant to specific embodiment of the invention, wherein the composition comprises tPA double mutant, as tPA Ser$^{481}$ to Ala and point mutations in the tPA protease domain, for example, point mutations replacing KHRR$^{299-302}$ with AAAA. In certain embodiments, this particular mutant is designated tPA$^{Ser481Ala-DS}$. It should be further noted that the mutant of the invention may be also referred to as tPA-S$^{481}$A-DS.

More particular embodiments of such mutant is a mutant comprising the amino acid sequence as denoted by amino acid sequence SEQ ID NO. 2. The inventors conceived that this tPA mutant would be lacking catalytic activity as well as ability to bind to NMDA-R, but not the ability to bind to fibrin. The inventors have been extensively demonstrated efficiency of said mutant in inhibition of tPA and uPA fibrinolysis in vitro (Example 1) as well as beneficial effects thereof in the in vivo model of head trauma (Example 2).

NMDA-Rs govern a range of physiological conditions including neurological disorders caused by neuronal injury, psychiatric disorders and neuropathic pain syndromes. Over-activation of the NMDA-Rs (also known as NMDA-R-mediated excitotoxicity) has been linked to pathological conditions of acute and chronic neurodegeneration.

It should be noted that the tPA$^{Ser481Ala-DS}$ double mutant of the invention devoid of the serine protease activity and therefore, cannot activate NMDA-R. However, since tPA binds NMDA-R through the PAI-1 docking site, the disruption of this site prevents or inhibits interaction of tPA with NMDA-R, this mutant cannot compete with the Wild type tPA and therefore cannot prevent activation of NMDA-R. More specifically, the combination of Ser$^{481}$ and at least one of Lys$^{296}$, His$^{297}$, Arg$^{298}$, Arg$^{299}$, preferably all said mutations, creates a tPA mutant which inhibits or prevents fibrinolysis and does not affect NMDA-R. Such mutants may be favorable in cases where the treated disorder or trauma is not a brain or neural trauma, and no effect of the treatment on the nervous system is desired, or in cases where fibrinolysis is required, even in the nervous system and in particular the brain, but no effect on the NMDA-R is desired. In some specific embodiments, the mutated tPA molecule of the invention carries a point mutation in Ser$^{481}$ to Ala and point mutations in KHRR$^{299-302}$ to AAAA, and comprises the amino acid sequence of SEQ ID NO. 2. It should be also noted that this mutant further comprises two additional amino acid residues at the N' terminus of the molecule. These two residues, Arg and Ser (RS), were introduces only for cloning purpose. Therefore, in certain embodiments, the tPA-S$^{481}$A-DS mutant of the invention may comprise the amino acid sequence as denoted by SEQ ID NO. 13.

As shown by the Examples, although this mutant cannot prevent activation of NMDA, when administered about 2 hr following injury, where the damage is caused by bleeding and not by the NMDA-R, the tPA$^{Ser481Ala-DS}$ mutant have been shown to exhibit beneficial therapeutic effects on head injury, as reflected in lower neurological severity scores (NSS).

As indicated herein, such reduction or decrease in neurological symptoms may be of about 10 to 95%, specifically, about 10%, 15%, 20%, 25%, 30%, 35%, 40%, 45%, 50%, 55%, 60%, 65%, 70%, 75%, 80%, 85%, 90%, 95% and even 99% of the NSS in a subject in need thereof. Furthermore, neural cell death following head trauma may be prevented or inhibited by administering tPA mutants of the invention, especially tPA Ser$^{481}$ to Ala and tPA double mutants, to subjects that had undergone such an injury, or risk such an injury. The decrease in neural cell death following head trauma may be of about 10 to 95%, specifically, about 10%, 15%, 20%, 25%, 30%, 35%, 40%, 45%, 50%, 55%, 60%, 65%, 70%, 75%, 80%, 85%, 90%, 95% and even 99% said subject. Specifically, cell death may be inhibited or prevented in the CA3 hippocampal area.

According to yet another embodiment, the composition of the invention may comprise a combination of different mutants. More specifically, such composition may comprise the tPA$^{Ser481Ala}$ mutant and at least one of the other tPA mutants, specifically, any one of: (a) a mutant carrying a point mutations in positions 299-302 of the Wild type molecule as denoted by SEQ ID NO. 7, substituting KHRR$^{299-302}$ to AAAA. A specific embodiment for such mutant may be provided by SEQ ID NO. 15. (b) a mutant carrying a point mutations in positions 120 and 106106 of the Wild type molecule as denoted by SEQ ID NO. 7, substituting N$^{120}$ to Q and T$^{106106}$ to N. A specific embodiment for such mutant may be provided by SEQ ID NO. 16. (c) a mutant carrying a deletion of at least one of the finger and K1 domains, as denoted by SEQ ID NO. 4; and (d)

uPA/scuPA mutated molecule carrying a point mutation in Ser$^{356}$ to Ala, as denoted by SEQ ID NO. 5.

According to the invention, each mutation, deletion or combination of mutations and/or deletions modifies the activity or effect of the resultant tPA mutant protein. Thus, in the context of the present invention, mutants having significant effect on fibrinolysis but not on NMDA-R activation would be desirable for various purposes. For example, it was found that N$^{120}$ to Q mutation shift the glycosylation site within K1 by 14 amino acids upstream and a T$^{106106}$ to N mutant exhibits an additional glycosylation site on K1. Both mutations result in a significantly longer half-life and increased affinity to fibrin compared to WT tPA. The combination of these mutations and the Ser$^{481}$ to Ala mutation may results in a longer-lasting and more potent fibrinolysis inhibitor. In some specific embodiments, the mutated tPA molecule of the invention carries a point mutation in Ser$^{481}$ to Ala and point mutations in N$^{120}$ to Q and in T$^{106}$ to N, and comprises the amino acid sequence of SEQ ID NO. 3. It should be also noted that this mutant further comprises two additional amino acid residues at the N' terminus of the molecule. These two residues, Arg and Ser (RS), were introduces only for cloning purpose. Therefore, in certain embodiments, the tPA-$S^{481}$A-$N^{120}$Q-$T^{106}$N triple mutant of the invention may comprise the amino acid sequence as denoted by SEQ ID NO. 14.

Further, a mutant lacking the finger and K1 domains, cannot bind to fibrin, but can still bind the NMDA-R and has a longer half life in the circulation, since K1 enhances tPA clearance. Such mutant will not bind fibrin or affect fibrinolysis, but inhibit NMDA-R activation. In some specific embodiments, the mutated tPA molecule of the invention carries a point mutation in $Ser^{481}$ to Ala and deletion of at least one of the finger and K1 domains, and comprises the amino acid sequence of SEQ ID NO. 4.

Furthermore, a finger domain fragment of tPA alone or combined with the K1 domain may inhibit tPA mediated fibrinolysis by competing with the binding of tPA to fibrin and preventing tPA mediated fibrinolysis.

The inventors also contemplate corresponding uPA mutants. For instance, uPA/scuPA (SEQ ID No. 5) mutants with a single mutation of $Ser^{356}$-Ala lack a protease catalytic activity, and therefore prevent/inhibit plasminogen and NMDA-R activation.

According to one of its aspects, the invention provides a composition as described by the invention, for use in a method for the treatment, amelioration, inhibition or prophylaxis of a disease, disorder, or condition associated with fibrinolysis.

Thus, the invention also provides a composition for use in a method of treatment, amelioration, inhibition or prophylaxis of diseases, disorders, or conditions that may include any one of coagulopathy, thrombocytophenia, hemorrhage, noncompressible hemorrhage, trauma induced hemorrhage, gynecological hemorrhage, minor surgery or major surgery bleeding, conjenital coagulopathy, hemophilia, disseminated intravascular coagulation (DIC) and conditions related to angiogenesis.

It should be appreciated that coagulopathy (also clotting or bleeding disorder) as referred herein relates to a condition in which the blood's ability to clot is impaired. More specifically in this context, hypocoagulability is an unusual susceptibility to bleeding, that is, an increased bleeding diathesis, due to an abnormality in coagulation. Coagulopathy may be caused by reduced levels or absence of blood clotting proteins, known as coagulation factors. Specific group within coagulopathies constitute congenital coagulopaties wherein the deficiency of coagulation factors is genetically determined and inherited. Coagulopathy may also occur as a result of dysfunction or reduced levels of platelets. Coagulopathies may severely complicate blood loss from injury, childbirth, surgery, and other conditions in which bleeding can occur.

As the present invention is particularly relevant to congenital coagulopaties, it should be further appreciated that the most common congenital coagulopathies include: hemophilia (hemophilia A or factor VIII deficiency) an X-linked disorder characterized by spontaneous musculoskeletal bleeding; hemophilia B (or Christmas disease or factor IX deficiency) has similar symptoms but is less common and is highly dependent on vitamin K; Von Willebrand's disease (vWD) a hereditary disorder with prolonged bleeding time due to a clotting factor deficiency and impaired platelet function; hypoprothrombinemia is another congenital deficiency of clotting factors that can lead to hemorrhages; other disorders include factor XI deficiency (hemophilia C) and factor VII deficiency (also called Serum Prothrombin Conversion Accelerator (SPCA) deficiency).

Disseminated Intravascular Coagulation (DIC, also known as consumption coagulopathy) is a systemic process caused by pathologic thrombin generation that may ironically result in hemorrhage due to depletion of clotting. DIC etiologies include sepsis, snakebites, burns, amniotic fluid embolism, trauma, acute leukemias and other malignancies.

In certain embodiments, the present invention is particularly relevant for the treatment and amelioration and possibly prevention of thrombocytopenia which is the most common coagulation disorder. Thrombocytophenia is defined as a platelet count below the normal range (between 150,000 to 450,000/μl±2 standard deviation). Most notably, when the platelet count is below 50,000/μl, risks for spontaneous mucocutanous bleedings (gingival bleed, epistaxis, menorrhagia, petechiae, ecchymoses) and life threatening spontaneous intracraneal hemorrhages or gastrointestinal bleeding increase rapidly. Aprt form platelet count, the diagnostic criteria for thrombocytopenia include elevated values in the D-dimer (DD) test and exclusion of artifactual or "pseudothrombocytopenia" evident in in-vitro clumping of platelets in the presence of ethylenediaminetetraacetic acid (EDTA) but when using cirated blood. Etiologies of thrombocytopenia include: immune thrombocytopenic purpura (ITP also idiopathic thrombocytopenic purpura)—an autoimmune condition caused by the presence of antiplatelet antibodies; thrombotic thrombocytopenic purpura or hemolytic uremic syndrome (TTP-HUS) a relatively uncommon life-threatening form of thrombocytopenia caused by inherited or acquired conditions; drug-induced thrombocytopenia is relatively common, specifically the chemotheraphy induced thrombocytopenia and heparin induced thrombocytopenia (HIT); sepsis/infection induced thrombocytopenia, specifically resulting from bacterial or viral infections (e.g. HIV, EBV or CMV); DIC and hypersplenism may cause thrombocytopenia due to sequestration of blood elements; other causes include pregnancy induced thrombocytopenia and bone marrow transplant, blood transfusion or metastatic carcinomas induced thrombocytopenia.

Further, the invention is exceptionally applicable to a large and versatile group of conditions referred herein under general terms as hemorrhages or bleedings. According to the American College of Surgeons' advanced trauma life support (ATLS) classification, hemorrhages include: Class I—loss of up to 15% of blood volume with no change in vital signs; Class II—15-30% loss with symptoms of tachycardia, peripheral vasoconstriction and paleness of the skin; Class III—30-40% loss with significant drop of blood pressure, increase of heart rate and peripheral hypoperfusion (shock); Class IV—>40% loss reaching the limit of the body's compensation wherein aggressive resuscitation is required to prevent death. According to the World Health Organization (WHO), the standardized grading scale to measure the severity of bleeding consists of Grade 0—no bleeding; Grade 1—petechial bleeding; Grade 2—mild blood loss (clinically significant); Grade 3—gross blood loss requiring transfusion (severe); Grade 4—debilitating blood loss including cerebral associated with fatality.

Hemorrhage prone sites include mouth (hematemesis, hemoptysis), nose (epistaxis); anus (hematochezia), urinary tract (hematuria), upper head (intracranial, cerebral and intracerebral hemorrhages) and subarachnoid hemorrhage (SAH) within the subarachnoid space usually resulting from some pathologic non-traumatic process, such as rupture of a berry aneurysm or arteriovenous malformation (AVM); lungs (pulmonary hemorrhage); gynecologic (vaginal bleeding, postpartum hemorrhage, breakthrough bleeding and ovarian bleeding; internal bleedings (into the spleen and liver); and gastrointestinal (upper gastrointestinal bleed).

Hemorrhages may be also caused by either traumatic injury or other medical conditions (e.g. internal bleedings induced by Warfarin/Coumadin) or a combination of both.

Among trauma-induced hemorrhages, specifically relevant noncompressible hemorrhages to the torso (chest, abdomen, pelvis and back), in which compression cannot be applied, unlike extremity wounds that are more amenable to compression to stop bleeding. Especially for noncompressible hemorrhages, control of bleeding and limitation of blood loss is the only way to avoid a massive hemorrhage. The present composition of the invention, when administered intravenously, provides potential treatment for truncal hemorrhages that are particularly resistant to the currently available treatments.

Specifically pertinent to this context is hemorrhagic stroke involving bleeding within the brain including: as deep intracerebral hemorrhage in the thalamus, basal ganglia, or cerebellum; lobar intracerebral hemorrhage predominantly in the cerebrum; SAH caused by cerebral aneurysm; or hypertensive intracerebral hemorrhage due to high blood pressure.

Pertinent to the present context are gynecological hemorrhage that include menorraghia, pregnancy or paritutrition and obstetric bleeding, postpartum hemorrhage. It should be noted that the compositions as well as any of the methods, uses and kits of the invention may be applicable for any of the disorders described herein.

The invention may be also relevant for treating and preventing bleeding resulting from minor surgery, i.e. surgical procedures that do not involve anesthesia or respiratory assistance such as circumcision, dental surgery; as well as for major surgery i.e. any surgery in which a patient must undergo general anesthesia, for example orthopedic surgery, urological surgery.

In the context of hemorrhages, the invention may be administered in conjunction with an additional therapeutic agent. A specific example for such additional agent may be at least one coagulation promoting agent. Such coagulation promoting agent may be selected from thrombin, fibrinogen, platelet activating agent, plasma preparations and platelets reach plasma preparations and vitamin K. In addition, the invention can be administered with styptics that work by contracting tissue to seal injured blood vessels or other locally-acting agents that work by causing vasoconstriction or promoting platelet aggregation.

As surprisingly shown by the present invention, the mutated tPA molecule of the invention, effectively inhibit also the fibrinolytic activity of uPA. The involvement of uPA has been recently demonstrated in modulation of angiogenesis. More specifically, uPA has been implicated in tissue proliferation and cell adhesion, as it regulates proteolytic degradation of the extracellular matrix, liberating growth factors and matrix metalloproteases. Moreover, uPA has been shown as required for both endogenous and vascular endothelia growth factor (VEGF)-augmented angiogenesis. On the other hand, uPA has been shown as involved in the generation of angiostatin from plasminogen. It should be noted that angiostatin is an inhibitor of angiogenesis. The inhibition of the activity of uPA by the mutants of the invention may be therefore useful in modulating angiogenesis. It should be noted that modulation refer to either enhancing or inhibiting angiogenesis. In more specific embodiments, the mutants of the invention may be used in enhancing angiogenesis in a subject in need thereof. As used herein, the terms "enhancing" and "promoting" relate to the augmentation or amplification of an angiogenic process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In other specific embodiments, the mutants of the invention may be used in inhibiting angiogenesis in a subject in need thereof. As used herein, the terms "inhibiting" and "reducing" relate to the elimination, reduction and attenuating an angiogenic process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

Therefore, the present invention further provides according to some embodiments, the use of the composition of the invention in a method for modulating angiogenesis.

Angiogenesis as referred herein related to a physiological process of formation of new blood vessels from pre-existing vessels. This is distinct from vasculogenesis, which is the de novo formation of endothelial cells from mesoderm cell precursors. Angiogenesis is a normal and vital process in growth and development, as well as in wound healing and in the formation of granulation tissue. It is also a fundamental step in the transition of tumors from a benign state to a malignant one, leading to the use of angiogenesis inhibitors in the treatment of cancer. Specifically relevant to this context are conditions related to insufficient angiogenesis, such as coronary artery disease, stroke, chronic wounds and during surgery.

It has been demonstrated that angiogenesis is controlled by a net balance between molecules that have positive and negative regulatory activity. This observation has led to the concept of "angiogenic switch", in which the endothelial activation status is determined by the induction of positive regulators and/or loss of negative regulators. As the present invention affects the balance between bioavailability of plasminogen and uPA, it may further provide means to modulate angiogenesis together with other known factors as vascular endothelial growth factor (VEGF) cytokines and angiopoietins.

In the same way, the invention provides the composition of the invention for use in a method for promoting and enhancing wound healing.

It should be appreciated that wound healing (or cicatrisation) as referred herein relates to an intricate process in which the skin or another organ-tissue repairs itself after injury. In normal skin, the epidermis (outermost layer) and dermis (inner or deeper layer) exist in steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis (not considered a phase by some authors), (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis).

In the inflammatory phase, bacteria and debris are phagocytosed and removed, and factors are released that cause the migration and division of cells involved in the proliferative phase.

The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodeling phase, collagen is remodeled and realigned along tension lines and cells that are no longer needed are removed by apoptosis.

As used herein, the terms "enhancing" and "promoting" relate to the augmentation or amplification of a process or quantity related to wound healing, by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In yet other embodiments, the invention provides various composition as described herein for use as a biological glue.

As used herein, the expression "biological glue" refers to compositions as described above that comprise as an active ingredient at least one tPA mutated molecule, which can be used for a variety of purposes, for example, as sealants, delivery agents and adhesive compounds. More particularly, the composition of the invention may be used as biological glue for controlling bleeding and for the tight sealing of vessels, lungs or skin incisions, but also in case of intracavitary injuries. For instance, the composition of the invention may be used for sealing or reinforcing wounds that have been sutured or stapled, with pressure over an injured area, or to reduce blood loss and post-operative bleeding. When used as biological glue, the composition of the invention is preferably eliminated after the cicatrisation of the wound, by biodegradation, absorption or by simple detachment in the form of scabs.

According to some embodiments, the invention provides the composition of the invention for use in a method for inhibiting the fibrinolytic activity of at least one of tPA and uPA. It should be noted that such inhibitory action of the mutants of the invention may be performed either in vivo or in vitro, as shown in the following Examples.

It should be appreciated that the pharmaceutical composition of the invention may comprise the active compound in free form and be administered directly to the subject to be treated. Alternatively, depending on the size of the active molecule, it may be desirable to conjugate it to a pharmaceutically acceptable carrier prior to administration. Therapeutic formulations may be administered in any conventional dosage formulation. Formulations typically comprise at least one active ingredient, as defined above, together with one or more pharmaceutically and physiologically acceptable carriers in the sense of being compatible with the other ingredients and not injurious to the patient. In some specific embodiments, the pharmaceutical composition of the invention may be suitable for injection. The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome containing formulations.

Formulations include those suitable for topical, oral, rectal, nasal, or parenteral (including subcutaneous, intramuscular, intraperitoneal (IP), intravenous (IV) and intradermal) administration. The nature, availability and sources, and the administration of all such compounds including the effective amounts necessary to produce desirable effects in a subject are well known in the art. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

In some specific embodiments, the pharmaceutical composition of the invention may be applicable for topical administration or transdermal delivery. Such composition and formulations may include transdermal patches, ointments, lotions, creams, gels, drops, suppositories, sprays, liquids and powders. Conventional pharmaceutical carriers, aqueous, powder or oily bases, thickeners and the like may be necessary or desirable.

Transdermal delivery may be accomplished in various ways. By "transdermal" herein is meant the passing through the skin and into a subject's blood stream, whereby to provide a systemic effect. Whilst the term embraces transmucosal, i.e. passing through mucosal tissue so as to embrace sublingual, buccal, vaginal and rectal delivery, typically transdermal delivery is affected through a subject's skin. For this reason, references are generally made herein to skin for simplicity's sake only although it will be appreciated that the transdermal delivery described herein may also be transmucosal.

According to some embodiments, a transdermal delivery system is provided comprising a composition of the invention. Such compositions may be presented in a number of different ways, a typical presentation being one that permits transdermal delivery. For example, the compositions may be contained within an adhesive patch designed to be affixed to the skin of a patient, or formulated into a capsule or sachet susceptible to easy rupture (e.g. by rubbing or squeezing between fingers) for release of a calculated dose of the tPA mutants formulation onto the skin into which it may be rubbed. Other formulations, such as topically applied gels, are known to the skilled person. Typically the compositions of the present invention are presented as adhesive transdermal patches. Such patches comprising composition of the invention constitute a delivery system for transdermal delivery of the composition of the invention contained within them.

Transdermal patches comprising the compositions of this invention contain a quantity of tPA mutants to be delivered and an adhesive to allow contact between the patch and the skin to be maintained in absence of external pressure. Typically the patches comprise a first face that contacts the skin, and a protective backing layer on a second face of the patch opposing the first face, one face of the backing layer being exposed to the environment during use and comprising a material that is impervious to the components present in the patch. Attached to the first face of a transdermal patch is typically a releasable protective layer that protects the patch prior to its use and which may be released from the adhesive disposed at the first face of the patch prior to the patch being affixed to the skin.

By a patch or adhesive patch herein is meant material adapted for adhesion to a subject's skin or mucosal tissue. Typically patches herein have a substantial degree of rigidity and, in use, comprise a backing layer exposed to the environment and a composition of the invention beneath the backing layer. However, the patches of the invention may also be of a non-rigid nature.

An exemplary transdermal delivery system comprises: (a) at least one drug reservoir containing the at least one tPA mutant, or any salt, base, ester or amide, or any combination or mixture thereof and, optionally, a pharmaceutically acceptable inorganic or organic base in an amount effective to enhance the flux of the active ingredient through the body surface without causing damage thereto; (b) a means for maintaining the system in active ingredient transmitting relationship to the body surface and forming a body surface-system interface; and (c) a backing layer that serves as the outer surface of the device during use. In one embodiment, the drug reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active ingredient, inorganic or organic base, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The said transdermal patches that may be used in transdermal delivery of the at least one tPA mutant or any salt, base, ester or amide, or any combination or mixture thereof comprise the backing layer, the active ingredient-containing layer and the release liner.

The release-control membranes to control the transdermal absorption of the active ingredient or the adhesive layers to adhere to the skin can be added, if desired. Furthermore, reservoir-type patches can be adopted. In some embodiments, in the active ingredient-containing layer is a matrix-type adhesive layer containing the active ingredient and an adhesive agent as a base agent. By providing the patches as the matrix-type patches, the patches can be easily designed and the additional layer such as the adhesive layers is not needed so that the cost for manufacturing the patches can be reduced.

The adhesive agents contained in the drug-containing layers of the transdermal patches of the present invention are, according to specific embodiments, non-aqueous adhesive agents, and are inclusive of rubber adhesive agents, acryl polymers and silicone polymers.

The rubber adhesive agents are inclusive of one or not less than two agents selected from styrene-isoprene-styrene block copolymer, styrene-butadiene-styrene block copolymer, styrene-butadiene rubber, polyisobutylene, polybutene, butyl rubber, natural rubber and isoprene rubber and can be used in the present invention.

The acryl polymers include, but is not limited to, polymers or copolymers containing at least one kind of the (meth)acrylate represented by 2-ethylhexyl acrylate, methyl acrylate, butyl acrylate, 2-hydroxyethyl acrylate, 2-ethylhexyl methacrylate and the like as a monomer unit, for example, adhesive polymers such as acrylic acid-octyl acetate copolymer, 2-ethylhexyl acrylate-N-vinyl-2-pyrrolidone-1,6-hexaneglycolyl dimethacrylate copolymer, 2-ethylhexyl acrylate-vinyl acetate copolymer, 2-ethylhexyl acrylate-vinyl acetate-acrylic acid copolymer, 2-ethylhexyl acrylate-2-ethylhexyl methacrylate-dodecyl methacrylate copolymer, methyl methacrylate-2-ethylhexyl acrylate copolymerization resin emulsion, acryl polymer contained in acryl resin-alkanolamine solution can be used and the commercially available DURO-TAK (registered trademark) acrylate adhesive agents series (provided by Henkle Japan Ltd.), GELVA (registered trademark) acrylate adhesive agents series (provided by Monsanto Co.), SK-DYNE MATRIDERM (provided by Soken Chemical and Engineering Co., Ltd) or EUDRAGIT (registered trademark) series (provided by Higuchi Inc.) and can be used in the present invention.

The silicone polymers include derivatives of polysiloxane (for example, silicone polymer such as polydimethylsiloxane and amine-resistant polydimethylsiloxane).

It should be noted that the matrix and film applicable for the transdermal delivery system are described herein in connection with rapid oral delivery are also relevant for the transdermal delivery.

In yet another aspect, the invention provides an isolated tPA mutated molecule, or any fragment or functional derivative thereof. More specifically, the tPA mutant provided by the invention carries a point mutation in position 481 of the Wild type molecule as denoted by SEQ ID NO. 7, substituting $Ser^{481}$ to Ala and at least one further mutation that may be any one of: (a) point mutations in positions 299-302 of the Wild type molecule as denoted by SEQ ID NO. 7, substituting $KHRR^{299-302}$ to AAAA; (b) point mutations in positions 120 and 106 of the Wild type molecule as denoted by SEQ ID NO. 7, substituting $N^{120}$ to Q and $T^{106}$ to N; and (c) deletion of at least one of the finger and K1 domains, as denoted by SEQ ID NO. 4.

In other embodiments, the invention relates to an isolated tPA mutated molecule that carries point mutations in $Ser^{481}$ to Ala and in $KHRR^{299-302}$ to AAAA. In more specific embodiments, such mutant is designated $tPA^{Ser481Ala-DS}$, more specifically, such mutant may comprise the amino acid sequence as denoted by SEQ ID NO. 2. In yet another embodiment, the mutant of the invention may further comprise N terminal RS residues. Such mutant may comprise the amino acid sequence as denoted by SEQ ID NO. 13.

In further embodiments, the invention relates to a mutated tPA that carries a point mutation in $Ser^{481}$ to Ala and point mutations in positions 120 and 106 of the Wild type molecule as denoted by SEQ ID NO. 7, substituting $N^{120}$ to Q and $T^{106}$ to N. In more specific embodiments, such mutant may comprise the amino acid sequence of SEQ ID NO. 3. In yet another embodiment, the mutant of the invention may further comprise N terminal RS residues. Such mutant may comprise the amino acid sequence as denoted by SEQ ID NO. 14.

In further embodiments, the invention relates to a mutated tPA molecule that carries a point mutation in $Ser^{481}$ to Ala and deletion of at least one of the finger and K1 domains. More specifically, such mutant may comprise the amino acid sequence of SEQ ID NO. 5.

In the whole description, it should be appreciated that the terms "mutated tPA", "tPA mutant", "mtPA" or "tPA mutated molecule" are used herein interchangeably and refer to any mutated native tPA and recombinant mutated tPA, as well as modified forms of tPA that are devoid of the enzymatic activities of native tPA. For example, the $Ser^{481}$-Ala tPA mutant of the invention are essentially devoid of protease or serine protease catalytic activity. Thus, the mutated tPA molecule of the invention has an impaired, decreased or reduced activity. A preferred mutated tPA molecule lacks any catalytic activity. According to one embodiment of the present invention at least about 10-100%, more specifically, about 10%, 15%, 20%, 25%, 30%, 35%, 40%, 45%, 50%, 55%, 60%, 65%, 70%, 75%, 80%, 85%, 90%, 95%, 99% and even 100% of the tPA activity is abolished by the mutations performed by the invention, as compared to the WT (wild type) tPA activity. It should be noted that the enzymatic activity of tPA can be measured by assessing the ability of the molecule to convert plasminogen to plasmin.

The invention provides the different tPA mutants as described herein above, as well as any variants and fragments or peptides thereof.

By "fragments or peptides" it is meant a fraction of said mutated tPA molecule. A "fragment" of a molecule, such as any of the amino acid sequences of the present invention, is meant to refer to any functional amino acid subset of the mutated tPA molecule. This may also include "variants" or "derivatives" thereof. A "peptide" is meant to refer to a particular amino acid subset having functional activity. By "functional" is meant having the same biological function, for example, having the ability of competing with the WT tPA and inhibiting the activation of plasminogen, or having the ability of competing with the Wild type tPA and uPA or the ability of inhibiting fibrinolysis by both enzymes. A "variant" of such molecule is meant to refer a naturally occurring molecule substantially similar to either the entire molecule or a fragment thereof. The term "derivatives" as used herein mean a molecule comprising the amino acid sequence of the mutated tPA molecule, with any insertions, deletions, substitutions and modifications that do not interfere with at least one of the ability of said molecule to inhibit the fibrinolysis mediated by tPA and uPA. A derivative should maintain a minimal homology to said amino acid sequence, e.g. even less than 30%, preferably, 90% to 40% homology, 80% to 50% or 70% to 60%. It should be appreciated that the terms "insertions" and "deletions" are meant any addition or reduction, respectively, of amino acid residues to the mutated tPA peptide used by the invention, between 1 to 50 amino acid residues, preferably, between 1 to 20 amino acid residues and most preferably, between 1 to 10 amino acid residues. More particularly, insertions or deletions, respectively, may include addition or reduction of 1, 2, 3, 4, 5, 6, 7, 8, 9 or 10 amino acid residues to the mutated tPA molecule of the invention.

It should be noted that the mutants of the invention are provided isolated and purified. The term "isolated", "purified" or "substantially purified", when applied to a peptide, protein or nucleic acid, such as any one of the mutant tPA molecules of the invention, denotes that the peptide, protein or nucleic acid is essentially free of other cellular components with which it is associated in the natural state. It is preferably in a homogeneous state, although it can be in either a dry or aqueous solution. Purity and homogeneity are typically determined using analytical chemistry techniques such as high performance liquid chromatography or polyacrylamide gel electrophoresis. A protein, peptide or nucleic acid which is the predominant species present in a preparation is substantially purified.

With respect to amino acid sequences, for example, the amino acid sequence of the any one of the tPA mutants of the invention, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

It should be noted that the term "Amino acid(s)" as used herein refer to all naturally occurring L-amino acids, e.g. and including D-amino acids. The amino acids are identified by either the well known single-letter or three-letter designations.

The term "derivative" is used to define amino acid sequence variants, and covalent modifications of a polypeptide made use of in the present invention. e.g. of a specified sequence. The functional derivatives of a any one of the tPA mutants of the invention, such as, for example, the tPA$^{Ser481Ala}$ tPA or tPA$^{Ser481-Ala-DS}$ (also referred to as tPA-S$^{481}$A-DS) mutant and its optionally further comprising other mutants as described herein, preferably have at least about 65%, more preferably at least about 75%, even more preferably at least about 85%, most preferably at least about 95% overall sequence homology, identity or similarity with the amino acid sequence of the tPA mutants polypeptides as structurally defined above.

"Homology" with respect to a native any one of the tPA mutants polypeptides of the invention and their functional derivatives is defined herein as the percentage of amino acid residues in the candidate sequence that are identical or similar with the residues of a corresponding native polypeptide, after aligning the sequences and introducing gaps, if necessary, to achieve the maximum percent homology, and not considering any conservative substitutions as part of the sequence identity. Neither N-nor C-terminal extensions nor insertions or deletions shall be construed as reducing identity or homology. Methods and computer programs for the alignment are well known. It should be appreciated that by the terms "insertions" or "deletions", as used herein it is meant any addition or deletion, respectively, of amino acid residues to any one of the tPA mutants of the invention, of between 1 to 50 amino acid residues, between 20 to 1 amino acid residues and specifically, between 1 to 10 amino acid residues. More particularly, insertions or deletions may be of any one of 1, 2, 3, 4, 5, 6, 7, 8, 9, or 10 amino acids. It should be recognized that insertions or deletions may be additions or reduction of amino acid residues from the N-terminal, the C-terminal end of the molecule or within the molecule or any combinations thereof.

The terms "identical", "substantial identity", "substantial homology" or percent "identity", in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region or over the entire molecule.

In yet another aspect, the invention relates to a method for the treatment, amelioration, inhibition or prophylaxis of a disease, disorder, or condition associated with fibrinolysis in a subject in need thereof. More specifically, the method of the invention comprises the step of administering to said subject, a therapeutically effective amount of at least one tPA mutated molecule or any composition comprising the same. In more specific embodiments, the tPA mutant carries a point mutation in position 481 of the Wild type molecule as denoted by SEQ ID NO. 7, substituting Ser$^{481}$ to Ala.

The invention still further provides a method for the treatment, amelioration, inhibition or prophylaxis of a disease, disorder, or condition associated with fibrinolysis in a subject in need thereof. More specifically, such method may comprise the of administering to said subject, a therapeutically effective amount of at least one tPA mutated molecule, wherein said tPA mutant carries a point mutation in Ser$^{481}$ to Ala and comprises the amino acid sequence of SEQ ID NO. 1. Further embodiments relate to the tPA-S$^{481}$A mutant having additional RS residues, as denoted by SEQ ID NO. 12.

In specific embodiments, the method of the invention is directed to the treatment, amelioration, inhibition or prophylaxis of a disease, disorder, or condition that may be any one of coagulopathy, thrombocytopenia, hemorrhage injuries, non-compressing bleeding, non-compressible hemorrhage, coagulation-related disorders, postpartum bleeding, postpartum hemorrhage, hemorrhagic stroke, subarachnoid hemorrhage hemophilia, and disseminated intravascular coagulation (DIC), trauma induced hemorrhage, gynecological hemorrhage, minor surgery or major surgery bleeding, conjenital coagulopathy, hemophilia, and conditions related to angiogenesis.

In yet another embodiment, the method of the invention involves the use of a tPA Ser481Ala mutated molecule that further comprises a further mutation/s that may be at least one of: (a) point mutations in positions 299-302 of the Wild type molecule as denoted by SEQ ID NO. 7, substituting KHRR$^{299\text{-}302}$ to AAAA; (b) point mutations in positions 120 and 106 of the Wild type molecule as denoted by SEQ ID NO. 7, substituting N$^{120}$ to Q and T$^{106}$ to N; and (c) deletion of at least one of the finger and K1 domains, as denoted by SEQ ID NO. 4.

In other embodiments, the method of the invention may use a tPA mutant that carries point mutations in Ser481Ala and in KHRR$^{299\text{-}302}$ to AAAA and is designated tPA Ser481Ala-DS. More specifically, such mutant may comprise the amino acid sequence as denoted by SEQ ID NO. 2. Further embodiments relate to the tPA-S$^{481}$A-DS mutant having additional RS residues, as denoted by SEQ ID NO. 13.

In other embodiments, in addition to administering the tPA$^{Ser481Ala}$ mutant, the method of the invention may further comprises the step of administering a therapeutically effective amount of at least one of: (a) a tPA mutant carrying point mutations in positions 299-302 of the Wild type molecule as denoted by SEQ ID NO. 7, substituting KHRR$^{299\text{-}302}$ to AAAA; (b) a tPA mutant carrying point mutations in positions 120 and 106 of the Wild type molecule as denoted by SEQ ID NO. 7, substituting N$^{120}$ to Q and T$^{106}$ to N; (c) a tPA mutant carrying deletion of at least one of the finger and K1 domains, as denoted by SEQ ID NO. 4; (d) uPA/scuPA mutated molecule carrying a point mutation in Ser$^{356}$ to Ala, as denoted by SEQ ID NO. 5; and (e) any combinations of (a) to (d) and any composition comprising the same.

As used herein, the term "treatment" refers to an improvement of at least one undesired manifestation of the disorder, condition or disease wherein inhibition of pathologic fibrinolysis or hyper-fibrinolysis is beneficial. As demonstrated, the invention may be beneficial for inhibition of fibrinolysis associated with head trauma, wherein in addition to inhibition of intracranial bleeding, neuronal cell death may be inhibited or prevented due to inhibition of NMDA-R-mediated excitotoxicity. The invention may also be conceived as a prophylactic treatment before the disorder, condition or disease occurs.

The term "amelioration" as referred to herein, relates to the inhibition or reduction of at least one of pathological fibrinolysis, or hyper-fibrinolysis, and the inhibition of neural damage, specifically neural damage associated with trauma.

The term "prophylaxis" refers to prevention or reduction the risk of occurrence of the biological or medical event that is sought to be prevented in a tissue, a system, animal or human by a researcher, veterinarian, medical doctor or other clinician.

As used herein, the term "subject in need thereof" relates to a mammalian subject, such as human, bovine, equine, murine, feline, canine or other, suffering from at least one of pathologic fibrinolysis, or hyper-fibrinolysis, and neural trauma as described, the treatment of which with any of the therapeutic tPA mutants of the invention, combinations and compositions thereof according to the invention, would ameliorate or decrease the severity of the disorder, both in intensity of the symptoms, rate of progression of the disorder, and time frame of the disorder.

The term "decrease" or "reduce", as referred to herein, relates to a decrease in value, amount, or rate. A decrease or a reduction as referred to herein, relate to the a reduction or lessening of a quantity or process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The methods and compositions of the invention further involve the use of a therapeutically effective amount of the mutants described herein. As used herein, the term "therapeutically effective amount" means an amount of a compound or composition which is administered to a subject in need thereof, necessary to effect a beneficial change in the severity of a disease or disorder, or prevent such disease, in said subject. This amount should also be within specific pharmacological ranges, to avoid toxic effects by overdosing. For example, in the present invention, a therapeutically effective amount of at least one of the tPA mutants of the invention, for the treatment of hyper-fibrinolysis would be the amount of these proteins administered to a subject which would induce a beneficial change in the subject, alleviating, ameliorating, or preventing the recurrence of said hyper-fibrinolysis, without causing detrimental side effects, or causing only mild side-effects. It is understood that the therapeutically effective amount is not an absolute term and depends on subjective circumstances, such as the subject's age, health, weight, and various other statistics, as described in the and specifically determined by the attendant physician or other person skilled in the art after an evaluation of the subject's conditions and requirements.

It should be noted that the mutants of the invention as well as any compositions thereof as described herein may be presented in unit dose forms containing a predetermined amount of each active ingredient per dose. Such a unit may be adapted to provide 0.01-100 mg/Kg of body weight of the tPA mutants of the invention. Specifically, either 0.1-10 mg/Kg, 5-15 mg/Kg, 10-30 mg/Kg, 25-50 mg/Kg 40-80 mg/Kg or 60-100 mg/Kg. More specifically, said effective dosage is about 0.01 to about 100 mg/Kg of the tPA mutants, about 0.1 to about 90 mg/Kg, about 0.3 to about 8 mg/Kg, about 0.4 to about 70 mg/Kg, about 0.5 to about 60 mg/Kg, about 0.7 to about 50 mg/Kg, about 0.8 to about 40 mg/Kg, about 0.9 to about 30 mg/Kg, about 1 to about 20 mg/Kg, specifically, about 1 to about 10 mg/Kg. Such doses can be provided in a single dose or as a number of discrete doses. In case a single dose may be administered, a dosage unit form may comprise an amount of about 0.01 mg to about 1000 mg, that may be administered one a day, a week or a month. The ultimate dose will of course depend on the condition being treated, the route of administration and the age, weight and condition of the patient and will be at the doctor's discretion.

It should be further noted that for the method of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the tPA mutants used by the invention or any composition of the invention in bodily fluids or tissues. Following successful treatment, it may be desirable to have the patient undergo maintenance therapy to prevent the recurrence of the disease state, wherein the combined composition of the invention is administered in maintenance doses.

It should be appreciated that the mutated molecule/s of the invention may be effective when administered to an injured subject after 10', 20', 30', 45', 50', 60', 90', 150', 180', 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 2 days, 3 days 4 days, 5 days, 6 days and even 7 days or more after the occurrence of the injury.

In one of its aspects, the method of the invention is applicable for inducing and promoting wound healing in a subject in need thereof. In more specific embodiments, the method comprises the step of applying to the wound a therapeutically effective amount of at least one tPA mutated molecule, or an anti fibrinolytic composition comprising the same, wherein said tPA mutant carries a point mutation in position 481 of the Wild type molecule as denoted by SEQ ID NO. 7, substituting $Ser^{481}$ to Ala.

Still further, the invention provides a method for modulating angiogenesis in a subject in need thereof. The method of the invention comprises the step of applying to the wound a therapeutically effective amount of at least one tPA mutated molecule, or a composition comprising the same. In more specific embodiments, a mutant useful in such methods may be a tPA mutant that carries a point mutation in position 481 of the Wild type molecule as denoted by SEQ ID NO. 7, substituting $Ser^{481}$ to Ala.

The invention further provides a method for inhibiting the fibrinolytic activity of at least one of tPA and uPA in a subject in need thereof. More specifically, such method comprises the step of administering to said subject a therapeutically effective amount of at least one tPA mutated molecule, or a composition comprising the same. It should be noted that in certain embodiments, such tPA mutant carries a point mutation in position 481 of the Wild type molecule as denoted by SEQ ID NO. 7, substituting $Ser^{481}$ to Ala.

In some specific embodiments, the above mentioned methods may involve tPA mutant that is designated tPA Ser481Ala and comprises the amino acid sequence as denoted by SEQ ID NO. 1 or 12.

In some other embodiments, the above mentioned methods of the invention may also involve administration of the $tPA^{Ser481Ala}$ where such tPA mutated molecule may further comprises at least one of: (a) point mutations in positions 299-302 of the Wild type molecule as denoted by SEQ ID NO. 7, substituting $KHRR^{299-302}$ to AAAA; (b) point mutations in positions 120 and 106 of the Wild type molecule as denoted by SEQ ID NO. 7, substituting $N^{120}$ to Q and $T^{106}$ to N; and (c) deletion of at least one of the finger and K1 domains, as denoted by SEQ ID NO. 4.

In more specific embodiments, the above mentioned methods provided by the invention may involve the administration of a tPA mutant that carries point mutations in Ser481Ala and in $KHRR^{299-302}$ to AAAA and is designated $tPA^{Ser481Ala-DS}$. In more specific embodiments, such mutant comprises the amino acid sequence as denoted by SEQ ID NO. 2 or 13.

In further embodiments, the above mentioned methods may further comprise the step of administering a therapeutically effective amount of at least one of: (a) a tPA mutant carrying point mutations in positions 299-302 of the Wild type molecule as denoted by SEQ ID NO. 7, substituting $KHRR^{299-302}$ to AAAA; (b) a tPA mutant carrying point mutations in positions 120 and 106 of the Wild type molecule as denoted by SEQ ID NO. 7, substituting $N^{120}$ to Q and $T^{106}$ to N; (c) a tPA mutant carrying deletion of at least one of the finger and K1 domains, as denoted by SEQ ID NO. 4; (d) uPA/scuPA mutated molecule carrying a point mutation in $Ser^{356}$ to Ala, as denoted by SEQ ID NO. 5; and (e) any combinations of (a) to (d) and any composition comprising the same.

Another aspect of the invention relates to the use of a therapeutically effective amount of at least one tPA mutant that carries a point mutation in position 481 of the Wild type molecule as denoted by SEQ ID NO. 7, substituting $Ser^{481}$ to Ala, in the preparation of a composition for the treatment of a disease, disorder, or condition associated with fibrinolysis.

It should be noted that any embodiments described herein above for the method of treatment, are also applicable for the use aspect of the invention.

According to a further aspect, the present invention also provides a biological glue comprising at least one tPA mutated molecule and at least one coagulation promoting agent. In more specific embodiments, the tPA mutant carries a point mutation in position 481 of the Wild type molecule as denoted by SEQ ID NO. 7, substituting $Ser^{481}$ to Ala. In further specific embodiments of the invention, each of said tPA mutated molecules and each of said at least one coagulation promoting agent may be optionally comprised within separate compartments.

According to more specific embodiments, the biological glue provided by the invention comprises a tPA mutant that carries a point mutation in $Ser^{481}$ to Ala and comprises the amino acid sequence of SEQ ID NO. 1 or 12.

In some specific embodiments of the biological glue composition of the invention, the at least one coagulation promoting agent may be at least one of thrombin, fibrinogen, platelet activating agent, plasma preparations, and platelets reach plasma preparations.

In more specific embodiments, the biological glue of the invention may comprises as a coagulation promoting agent thrombin. As referred herein, thrombin (also known as fibrinogenase, thrombase, thrombofort, topical, thrombin-C, tropostasin, activated blood-coagulation factor II, blood-coagulation factor IIa, factor IIa, E thrombin, beta-thrombin, gamma-thrombin) relates to a serine protease acting in the coagulation cascade. Thrombin is generated from a precursor prothrombin, which upon its proteolytic cleavage to active thrombin, catalyzes conversion of soluble fibrinogen into insoluble strands of fibrin, as well as many other coagulation-related reactions, ultimately resulting in reduction of blood loss.

In other specific embodiments, the biological glue of the invention may comprises as a coagulation promoting agent fibrinogen. More specifically, fibrinogen (factor I) is a soluble plasma glycoprotein that is converted by thrombin into fibrin during blood clot formation. During normal blood coagulation, a coagulation cascade activates prothrombin by converting it into the serine protease thrombin. Thrombin then converts the soluble fibrinogen into insoluble fibrin strands. These strands are then cross-linked by factor XIII to form a blood clot. As previously mentioned, fibrin provides a negative feedback in the activation of t-PA- and uPA-mediated fibrinolysis.

Still further, in some specific embodiments, the biological glue of the invention may comprises as a coagulation promoting agent plasma preparations. Plasma preparations referred herein relates to standard plasma preparation well known in the art, generally used for replacement of coagulation factors. The platelet-rich plasma preparations (PRP) are preparation of blood plasma that has been enriched with platelets. Specifically, two methods of PRP preparation approved by the U.S. Food and Drug Administration (FDA).

In other embodiments, the biological glue of the invention may comprises a tPA$^{Ser481Ala}$ mutated molecule that further comprises at least one of: (a) point mutation in positions 299-302 of the Wild type molecule as denoted by SEQ ID NO. 7, substituting KHRR$^{299-302}$ to AAAA; (b) point mutations in positions 120 and 106 of the Wild type molecule as denoted by SEQ ID NO. 12, substituting $N^{120}$ to Q and $T^{106}$ to N; and (c) deletion of at least one of the finger and K1 domains, as denoted by SEQ ID NO. 4.

According to some other embodiments of the biological glue provided by the invention may comprise in addition to the tPA mutant which carries a point mutation in Ser$^{481}$ to Ala, at least one further mutant that may be any one of: (a) point mutations in positions 299-302 of the Wild type molecule as denoted by SEQ ID NO. 7, substituting KHRR$^{299-302}$ to AAAA. Specific embodiment of such mutant may be provided by the mutant comprising the amino acid sequence as denoted by SEQ ID NO. 15. In another embodiment such additional mutant may carry (b) point mutations in positions 120 and 106 of the Wild type molecule as denoted by SEQ ID NO. 7, substituting $N^{120}$ to Q and $T^{106}$ to N. Specific embodiment for such mutant is provided by SEQ ID NO. 16. In yet another embodiment, such mutant may be a mutant having (c) deletion of at least one of the finger and K1 domains, as denoted by SEQ ID NO. 4, specific embodiment is provided by the mutant having the amino acid sequence as denoted by SEQ ID NO. 17; and (d) uPA/scuPA mutated molecule carrying a point mutation in Ser$^{356}$ to Ala, as denoted by SEQ ID NO. 5.

In another aspect, the invention provides a kit for treating a fibrinolysis-related condition. The kit of the invention may comprise:
(i) a biological glue comprising at least one tPA mutated molecule and at least one coagulation promoting agent. In certain embodiments, the tPA mutant carries a point mutation in position 481 of the Wild type molecule as denoted by SEQ ID NO. 7, substituting Ser$^{481}$ to Ala. In a specific embodiment, the tPA mutated molecules and each of said at least one coagulation promoting agent may be optionally comprised within separate compartments. In certain embodiments, the kit of the invention may optionally further comprise (ii) instructions for applying said biological glue composition.

In some specific embodiments, the biological glue comprised within the kit of the invention may comprise at least one coagulation promoting agent selected from thrombin, fibrinogen, platelet activating agent, plasma preparations, and platelets reach plasma preparations.

The biological glue of the kit may be administered in the form of a single pharmaceutical composition comprising a combination of the tPA mutant(s) and at least one coagulation promoting agent, together with a pharmaceutically acceptable carrier or diluent. Alternatively, the biological glue composition may have at least one of its components comprised in a pharmaceutical composition stored in a separate compartment. In such a case, the kit includes container means for containing both separate compositions, such as a divided bottle or a divided foil packet. However, the separate compositions may also be contained within a single, undivided container comprising several compartments.

Typically the kit includes instructions for the administration of the separate components. The kit form is particularly advantageous when the separate components are administered in different dosage forms, at different dosage intervals, or when titration of the individual components of the combination is desired by the prescribing physician.

According to specific embodiments, the kit of the invention may be suitable for use as a sealant, delivery agent or adhesive, and may be used for controlling bleeding, for the tight sealing of vessels, the sealing of lungs or skin incisions, and for treating intracavitary injuries. For instance, the kit of the invention may be used for sealing or reinforcing wounds that have been sutured or stapled, over an injured area, or to reduce blood loss and post-operative bleeding.

It should be appreciated that when the biological glue of the kit is comprised of at least two dosage forms, for instance one comprising at least one tPA mutated molecule and another one comprising at least one coagulation promoting agent, both dosage forms may be administered simultaneously.

Alternatively, said first dosage form and said second dosage form are administered sequentially in either order.

As shown in Example 5, administration of the mutants of the invention clearly reverses the anti-coagulant activity and side effects of an anti-coagulant such as coumadin (Warfarin). Therefore, a combined administration of the mutants of the invention with anti-coagulating agents, such as Coumadin or any heparin-like molecule, may serve as an antidote for uncontrolled bleeding caused thereby. More specifically, Heparin administration is the standard antithrombotic therapy indicated for acute venous thrombosis, for prophylaxis of thrombosis in the post-surgical (especially orthopedic) and immobile patient, and for flushing of intravenous lines to maintain patency. However, due to their potency, heparin and LMWH suffer drawbacks. Uncontrolled bleeding as a result of the simple stresses of motion and accompanying contacts with physical objects or at surgical sites is the major complication. In addition, approximately 5% (range up to 30%) of patients treated with heparin, and about 2% of patients receiving unfractionated heparin (UFH), develop immune-mediated thrombocytopenia (HIT) which may be complicated by either bleeding (as a consequence of decreased platelet count) or by arterial and venous thrombosis due to intravascular platelet clumping. The mutants of the invention may prevent such undesired effects of these anti-coagulating agents.

Thus, the invention further provides a method for inhibiting the anti-coagulating activity of an anti-coagulating agent or anti-aggregating agent in a subject in need thereof, comprising the step of administering to a subject being treated with an anti-coagulating agent a therapeutically effective amount of at least one tPA mutated molecule, or a composition comprising the same, wherein said tPA mutant carries a point mutation in position 481 of the Wild type molecule as denoted by SEQ ID NO. 7, substituting Ser$^{481}$ to Ala.

In certain embodiments, the mutant may be designated tPA$^{Ser481Ala}$ and comprises the amino acid sequence as denoted by SEQ ID NO. 1.

In yet another embodiment, the method of the invention may use a mutant that is designated tPA$^{Ser481Ala-DS}$ and comprises the amino acid sequence as denoted by SEQ ID NO. 2.

In yet another embodiment, the anticoagulant agent may be coumadin or heparin-like molecule.

It should be noted that the invention further encompasses inhibition of heparinoids or "heparin-like molecules". The term heparin-like molecule as used herein refers to a molecule that possesses anti-coagulant activity and chemical structure sufficiently similar to that of heparin such that said molecule is considered as a possible alternate therapy to a patient requiring heparin. A heparin-like molecule includes, but is not limited to, a low molecular weight heparin, a heparin analogue, and the like. The term low molecular weight heparin includes heparin molecules having a molecular weight of less than 8,000 daltons. The term heparin analogue comprises heparinoids, such as hepramine and its salts, chondroitins and their salts, and the like. The term heparin as used herein refers to standard commercially available heparin and derivatives thereof. The term standard heparin encompasses a mixture of unfractionated heparin molecules having an average molecular weight of between about 8,000 and about 30,000 daltons or any subfraction thereof. In addition, it is contemplated that the term heparin as used herein encompasses biologically active heparin molecules that are isolated from a mammalian source, that are chemically modified, or that are partially or completely synthesized de novo. The term heparin derivative encompasses salts of heparin, heparin fragments and the like.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Unless defined otherwise, all technical and scientific terms used herein have the same meaning as commonly understood by one of ordinary skill in the art to which this invention is related. The following terms are defined for purposes of the invention as described herein.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures and Reagents

Single-chain urokinase (uPA) was purified, characterized as previously reported in Higazi A et al., J Biol Chem. (1995), 270(29):17375-80). Glu-plasminogen was prepared from human plasma by the method of Deutsch and Mertz (Deutsch D G, Mertz E T. Science (1970), 170(3962):1095-6). Human thrombin, were obtained from Sigma (St Louis, Mo.). Recombinant tPA was from Genentech (South San Francisco, Calif.). Antibodies plasminogen IgG were purchased from Biotest (Kfar Saba Israel), where anti-tPA antibodies were provided by American Diagnostica. ECL—Amersham ECL Plus Western Blotting Detection System.

Animals

Eight to twelve weeks old C57 mice obtained from Harlan, Israel. Mice were administered standard laboratory chow and water ad libitum, and kept in controlled temperature and light conditions. Animal experiments were carried out according to the guidelines of the Hebrew University-Institutional Committee for Care and Use of Laboratory Animals, and with the committee's approval.

Plasminogen Activator Activity

Plasminogen activator activity was determined by adding tPA (50 nM) or uPA (20 nM), to a reaction mixture containing Glu-plasminogen and the plasmin chromogenic substrate Spectrazyme PL (100 µM) in phosphate-buffered saline (PBS) at 37° C., and the light absorbance at 405 nm was measured continuously over time. The initial velocities of plasmin generation at the different conditions were calculated from the change in the A405 nm over time. The initial velocity of the reaction at each plasminogen concentration was obtained by calculating the change in the rate of A405 over different time intervals and the results were expressed as the change in optical density (ΔOD) per minute, which represents the slope of the initial velocity of plasminogen activation (Higazi A et al., J Biol Chem. (1995), 270(29):17375-80).

Fibrinolysis Assay in Human Plasma Derived Clots

Clots were formed by placing human plasma (200 µL) in 16-mm diameter tissue culture wells flowed by adding thrombin (0.4 U/mL final concentration). Fibrinolysis was measured as described in Higazi A A et al., Blood (1998), 92(6):2075-83). Briefly, 10 µL tPA or uPA were placed over the plasma clots for 2 hours at 37° C., photographed and the diameter of the wholes were determined.

Fibrinolysis Assay in Blood Clots Derived from Fresh Whole Human Blood

Clot viscoelastic properties were assessed by thromboelastography (TEG®, Haemoscope) and rotational thromboelastometry (ROTEM®, Pentapharm). Both systems use a vertical pin within a cup that contains the WB sample. In TEG®, the cup oscillates and the pin is stationary whereas in ROTEM®, the cup is stationary while the pin oscillates. As a clot forms between the cup and the pin, the reduction in transmitted rotation from the cup to the pin (TEG®) or impedance to the oscillatory movement of the pin (ROTEM®) is detected and a trace is generated.

Closed Head Injury (CHI) Model

Head trauma was induced by using a modified weight-drop device, as previously described (Chen Y. et al. (1996) J. Neurotrauma, 13:557-568). Briefly, after induction of ether anesthesia, a midline longitudinal incision was made, the skin was retracted and the skull was exposed. The left anterior frontal area was identified and a Teflon tipped cone (2-mm diameter) was placed 1 mm lateral to the midline, in the midcoronal plane. The head was held in place manually and a 75-g weight was dropped on the cone from a height of 18 cm, resulting in focal injury to the left hemisphere. After trauma, the mice received supporting oxygenation with 95%

02 for no longer than 2 min and were then returned to their cages. In sham controls only anesthesia and skin incision were carried out.

Ser$^{481}$-Ala tPA/Plasminogen Protein Interaction Assay by Co-Immunoprecipitation Human Ser$^{481}$-Ala tPA and plasminogen, each at 100 nM final concentration in absence or presence of 1 μM uPA or fibrin degradation products, were incubated with goat polyclonal antibody to plasminogen and incubated with Protein A agarose. The protein A agarose beads were separated by centrifugation, washed, and boiled for 5 min. The beads were precipitated by centrifugation and the samples were run on NuPAGE 4-12%. As a control, 80 ng of human Ser$^{481}$-Ala tPA was loaded on the gel. The proteins from the gel were transferred onto a PVDF membrane. The membrane was blocked in milk/PBST before incubation for 1 hr with mouse monoclonal antibody to tPA. Subsequently it was washed, incubated with goat anti-mouse IgG-HRP conjugate, washed again, and detected with ECL.

Generation of tPA Mutants

Construction of the Ser$^{481}$ to Ala tPA Mutant

The cDNA fragment encoding mature human tPA sequence was amplified by PCR with the primers comprising a nucleic acid sequence as denoted by SEQ ID NOs 8 and 9, designed to introduce the 5'-flanking Bgl II and 3'flanking Xho I restriction sites, respectively. The amplified fragment was digested with Bgl II and Xho I restriction enzymes, and cloned into corresponding sites of the pMT/BiP/V5-HisA plasmid (Invitrogen). A Ser$^{481}$ to Ala mutation in tPA sequence was obtained by PCR with the pair of anti-parallel primers comprising a nucleic acid sequence as denoted by SEQ ID NOs 10 and 11, using the QuickChange Mutagenesis kit (Stratagen). Both sequences for the wild type and mutant constructs were thoroughly sequenced to confirm lack of PCR-introduced errors. Both the recombinant wt and S$^{481}$A mutant protein sequences contain 2 extra amino acids, RS-, at the N-terminus as the result of introduction of Bgl II cloning site into the original cDNA sequence encoding human tPA.

Construction of the Ser$^{481}$ to Ala-DS tPA Mutant tPA variants were synthesized and characterized as previously described (Nassar T, ET AL., *Am J Respir Cell Mol Biol* 43: 703-711, (2010)). cDNAs encoding mature human tPAs were cloned into the pMT/BiP/V5-HisA plasmid (Invitrogen, Carlsbad, Calif.). To generate catalytically inactive tPA (S481A) variant and the PAI-1 docking site (DS) variant (K296A/H297A/R298A/R299A), mutations were introduced in WT tPA by PCR using the QuickChange Mutagenesis kit (Stratagene, La Jolla, Calif.), and the complete sequences were verified. The protein contains two extra amino acids, RS-, at the NH2 terminus, resulting from introduction of the Bgl II cloning site. Proteins were expressed in S2 Drosophila Expression System (Invitrogen) according to the manufacturer's protocol and purified by antibody affinity chromatography using anti-tPA coupled to CN—Br activated Sepharose. The final products migrated as single bands on SDS-PAGE at the expected sizes, and the plasminogen activator activity was assessed using the plasmin chromogenic substrate SpectrazymePL. Proteins were stored at -70° C. or lyophilized before use.

Expression and Purification of tPA Mutant

Recombinant human tPA and its catalytically inactive counterpart S$^{481}$A tPA were expressed in S2 Drosophila Expression System (Invitrogen). The proteins were affinity purified using American Diagnostica PAM-1 MAb to tPA (Product #371, currently discontinued) coupled to CNBr-activated Sepharose 4 Fast Flow (Amersham Biosciences). The proteins were eluted with 0.1M glycine-HCl buffer, pH2.8 containing 0.2M Arg. The eluate was collected into PBS/0.2M Arg containing 80 microliters of 1M Tris-HCl, pH 8.0 per each ml of the eluate. Protein concentration/buffer change for PBS/0.2M Arg was performed on Amicon 30K filtering device. 3-5 micrograms of the purified proteins appears on SDS-PAGE as a single band of expected size with no contaminants. The proteins were stored at -70° C. or lyophilized.

Example 1

Inhibition of Clot Lysis by tPA Variants

Figure 1:
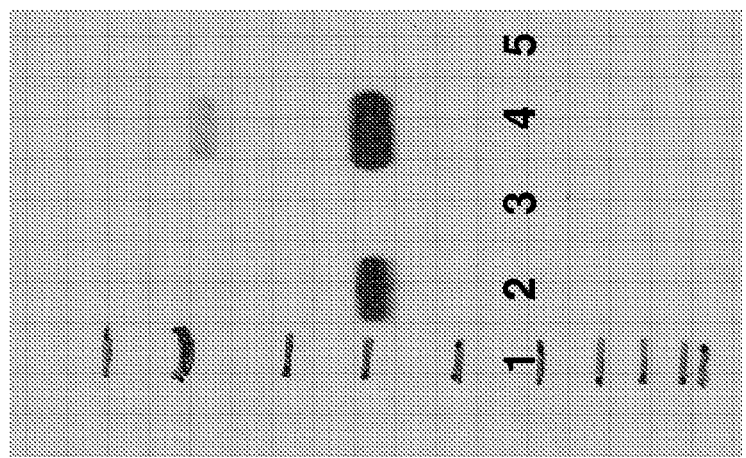
FIG. 1: Interaction of tPA-S$^{481}$A with fibrin and plasminogen

In order to examine the role of tPA in fibrinolysis, the inventors first examined the inhibitory activity of the mutants of the invention on fibrinogen activation. FIG. 1 demonstrates that tPA-S$^{481}$A binds to plasminogen only in the presence of fibrin (lane 2 vs. lane 5) and binding of this tPA variant is inhibited by uPA (lane 2 vs. lane 3).

This latter finding suggests that tPA-S$^{481}$A might also inhibit proteolytic activation of plasminogen by uPA in the presence of fibrin, which induces conformational changes in uPA and thereby accelerates plasminogen activation. As predicted, tPA-S$^{481}$A inhibited lysis of human plasma clots by the WT-uPA as well as the WT-tPA, as assessed both macroscopically (FIGS. 2A and 2B) and by quantifying lysis of clots formed from fresh human blood using TEG (FIG. 2C).

Identical anti-fibrinolytic activity was observed with tPA-S$^{481}$A-DS, which lacks both catalytic activity and the ability to bind to NMDA-Rs (FIGS. 2B and 2D). Both tPA-S$^{481}$A and tPA-S$^{481}$A-DS were more potent inhibitors of fibrinolysis than TA tested at its maximal inhibitory concentration (FIG. 2B).

Neither tPA-S$^{481}$A nor tPA-S$^{481}$A-DS inhibited plasminogen activation initiated by tPA or uPA in the absence of fibrin, as assessed by chromogenic assay using a small peptide as a plasmin substrate instead of fibrin (FIG. 2D). In contrast to its anti-fibrinolytic activity and as anticipated based on prior studies, TA dramatically stimulated activation of plasminogen by uPA (but not tPA) in chromogenic assay (FIG. 2D). The inventors interpreted these outcomes as that plasminogen must undergo conformational changes induced by fibrin that make it more susceptible to cleavage by uPA and bind tPA-S$^{481}$A or tPA-S$^{481}$A-DS so that the inhibitory effect of the tPA variants is manifested. To further test this hypothesis, plasminogen activation by uPA was assessed in the presence of tPA-S$^{481}$A or tPA-S$^{481}$A-DS added together with TA, which mimics the effect of fibrin on plasminogen structure and activation. In the presence of TA, both tPA-S$^{481}$A and tPA-S$^{481}$A-DS inhibited the activation of plasminogen by uPA (FIG. 2D). In theory, if the tPA variants bind to plasminogen in presence of fibrin or lysine analogs and thereby inhibit its activation by uPA, tPA-S$^{481}$A or tPA-S$^{481}$A-DS should be able to inhibit plasminogen activation by tPA by the same mechanism, even in the absence of fibrin. Indeed, FIG. 2D shows that both tPA variants inhibited the plasminogen activation induced by tPA in presence of TA. This suggests that TA mimics the stimulatory effect of fibrin on the binding of tPA variants to plasminogen (see FIG. 1) thus enabling tPA-S$^{481}$A or tPA-S$^{481}$A-DS to act as direct competitive inhibitors of WT tPA and uPA. Furthermore, the fact that under conditions (in absence of fibrin) where lysine analogues stimulate the activation of plasminogen by uPA or have no effect on its activation by tPA, tPA variants are inhibitors, strongly suggesting that under in-vivo pathological conditions they may be more potent and have lower side effects. To support the above hypothesis, the inventors examined the capacity of both tPA variants to inhibit the activation of plasminogen by reteplase. FIG. 2B shows that tPA-S$^{481}$A and tPA-S$^{481}$A-DS inhibit the clot lysis induced by reteplase, supporting the concept that both tPA variants inhibit plasminogen activation by tPA and uPA primarily by binding to plasminogen and by inhibiting the binding of the plasminogen activators, tPA and uPA.

Example 2

Stimulation of Endogenous Plasminogen Activator Activity by TBI Leads to the Expansion of Intracerebral Hemorrhage and Secondary Changes in Coagulation Parameters The close head injury (CHI) model of TBI induces extensive and time-dependent intracerebral hemorrhage evident on MRI and by extravasation of hemoglobin into the parenchyma (FIGS. 3A and 3B), followed by marked increase in tPA and uPA in the CSF 2 hours after CHI (FIG. 3C) accompanied by an increase in CSF fibrinolytic activity (FIGS. 3D 3E and 3F). IV injection of tPA-S$^{481}$A or tPA-S$^{481}$A-DS (2 mg/kg each) (FIGS. 3A, 3B and 3C) immediately after or 2 hours after CHI inhibited CSF fibrinolytic activity (FIGS. 3D, 3E and F) significantly attenuated the expansion of intracerebral hemorrhage. In contrast, injection of WT-tPA (5 mg/kg) immediately after CHI increased the extent of intracerebral hemorrhage in WT mice (FIG. 3B), which in turn could be inhibited by injection of equimolar concentrations of tPA-S$^{481}$A or tPA-S$^{481}$A-DS (FIG. 3B). Both TPA variants were more potent inhibitors of intracerebral hemorrhage than optimal concentrations of TA or aprotinin, to the extent that their effect was comparable to the inhibition induced by a combination of TA and aprotinin in optimal concentrations of (FIG. 3 B).

FIGS. 4A and 4B show that CHI led to secondary changes in coagulation parameters, revealed in significant increase in plasma d-Dimers and a fall in platelet counts. Administration of tPA-S$^{481}$A and tPA-S$^{481}$A-DS 2 hours after CHI significantly attenuated the increase in d-Dimers (FIG. 4A) and prevented the development of thrombocytopenia often associated with TBI (FIG. 4B).

Example 3

Blocking Endogenous Plasminogen Activator Activity Provides Neuroprotection Post TBI In addition to inhibiting endogenous fibrinolysis, tPA-S$^{481}$A also inhibited activation of NMDA-Rs by WT-tPA. To isolate the contribution of these two pathways to neurological outcomes, the inventors compared the activity of the two variants, tPA-S$^{481}$A and tPA-S$^{481}$A-DS that both lacks the catalytic activity and has a mutated docking site that prevents its binding to NMDA-Rs. tPA-S$^{481}$A-DS decreased ICH to the same extent as tPA-S$^{481}$A (FIG. 3B) and had the same effect on d-Dimers and post TBI thrombocytopenia (FIGS. 4A and 4B). However, in spite of having comparable effects on the extent of intracerebral hemorrhage, tPA-S$^{481}$A-DS given immediately after CHI provided less neuroprotection than tPA-S$^{481}$A (FIG. 5). The difference in the extent of neuroprotection strongly suggests that the tPA-S$^{481}$A exerts neuroprotection in this model through both pathways, i.e. by decreasing expansion of intracerebral hemorrhage and by preventing the activation of NMDA-Rs by endogenous plasminogen activators. In support of this hypothesis, the difference in neuroprotection provided by the two tPA variants vanished when each was given 2 hrs after the CHI (FIG. 5), a time when NMDA-R associated neurotoxicity is known to be complete but intracerebral hemorrhage continue to expand (FIG. 2).

Example 4

Contribution of tPA and uPA to Post-TBI Intracerebral and Brain Damage

Models of brain damage caused by controlled cortical impact and ischemic stroke are characterized by little or no intracerebral hemorrhage. In these models, mice with genetic deletion of tPA (tPA$^{-/-}$) but not uPA (uPA$^{-/-}$), show less brain damage than WT mice. These models therefore indicate a predominant role for endogenous tPA in causing brain damage. In contrast, both tPA$^{-/-}$ and uPA$^{-/-}$ mice showed better neurological outcomes than WT mice (FIG. 5), in the model studied here in which intracerebral hemorrhage is an important component based on the differential neuroprotective effect of the two TPA variants. This outcome further suggests that uPA plays an important role in post TBI intracerebral hemorrhage in this setting.

To test this hypothesis, the inventors examined the contribution of TPA and uPA to the development of ICH. CHI was induced concurrently in WT, tPA$^{-/-}$ and uPA$^{-/-}$ mice. TPA$^{-/-}$ and uPA$^{-/-}$ mice developed significantly less ICH than WT mice subjected to the same injury (FIG. 6A). The injury phenotype in both type of knock-out mice was "rescued" by injection of exogenous WT-tPA or WT-uPA (5 mg/kg each) and in both cases injection of an equimolar dose of tPA-S$^{481}$A inhibited the expansion of the post traumatic ICH (FIG. 6A). Putting together, this set of data supports the hypothesis regarding the role of uPA in the development of post TBI ICH and further support the hypothesis regarding the capacity TPA variant to inhibit fibrinolysis induced by TPA and uPA.

Example 5

Enhanced Primary Fibrinolysis by uPA is the Predominant Cause of ICH Post TBI

The data presented in FIGS. 6A and 6B show that tPA$^{-/-}$ mice developed thrombocytopenia and elevations in the plasma level of d-Dimers that were comparable to those seen in WT mice, yet were largely protected from ICH (FIG. 6C). Taken together, these observations suggest that increased intracranial fibrinolytic activity, rather than the post-CHI disturbances in systemic coagulation, is the predominant cause of intracerebral and its neurological squeal. To test this possibility, the inventors examined the effect of CHI on the plasma concentration of fibrinogen and the INR in a separate cohort of animals. The INR after CHI was <1.3 in all mice with no differences between tPA$^{-/-}$, uPA$^{-/-}$ or WT mice. In the same way, there was no significant depletion in fibrinogen or differences in fibrinogen concentration among the three cohorts (data not shown). In an independent test, the inventors examined the effect of anticoagulation the mice with warfarin prior to CHI. Mice had a mean INR of 2.5 at the time of trauma. Although warfarin increased the extent of ICH in WT mice, it had no such effect in tPA$^{-/-}$ or uPA$^{-/-}$ mice (FIG. 6C). Moreover, injection of tPA-S$^{481}$A to WT mice anticoagulated with warfarin almost totally inhibited post-traumatic intracerebral hemorrhage, (FIG. 6C) supporting the contention that increased fibrinolysis rather than a systemic coagulopathy is the main cause for intracerebral hemorrhage posts CHI.

The invention claimed is:

1. A method for inhibiting the fibrinolytic activity of tPA (tissue plasminogen activator) and uPA (urokinase plasminogen activator) in a subject suffering from a disorder or condition associated with fibrinolysis, with the proviso that said disorder or condition is not a brain or neural disorder or trauma, the method comprising:
   administering to said subject a therapeutically effective amount of at least one tPa mutant, said mutant being selected from the group consisting of:
   (a) a tPA mutant designated tPA$^{Ser481Ala}$ comprising the amino acid sequence as denoted by SEQ ID NO. 1, or a derivative thereof comprising the amino acid sequence as denoted by SEQ ID NO. 12; and
   (b) a tPA mutant designated tPASer481Ala-DS comprising the amino acid sequence as denoted by SEQ ID NO. 2, or a derivative thereof comprising the amino acid sequence as denoted by SEQ ID NO. 13;
   or of a composition comprising the same.

2. The method according to claim 1, wherein said disease, disorder, or condition is any one of coagulopathy, thrombocytopenia, hemorrhage, non-compressible hemorrhage, trauma induced hemorrhage, gynecological hemorrhage, minor surgery or major surgery bleeding, congenital coagulopathy, hemophilia, disseminated intravascular coagulation (DIC), gynecologic bleeding, gastrointestinal bleeding, internal bleeding, and conditions related to angiogenesis.

3. The method according to claim 1, for inducing and promoting wound healing in said subject.

4. The method according to claim 1, for modulating angiogenesis in a subject in need thereof, wherein the subject suffers from a condition related to angiogenesis.

5. The method according to claim 1, for inhibiting the anti-coagulating activity of an anti-coagulating agent in a subject in need thereof, wherein said anticoagulant agent is coumadin or a heparin-like molecule.

6. The method according to claim 1, wherein said administering step comprises administering a tPA mutant designated tPA$^{Ser481Ala}$ comprising the amino acid sequence as denoted by SEQ ID NO. 1, or a derivative thereof comprising the amino acid sequence as denoted by SEQ ID NO. 12, or a composition comprising said tPA mutant or derivative.

7. The method according to claim 1, wherein said administering step comprises administering a tPA mutant designated tPA$^{Ser481Ala-DS}$ comprising the amino acid sequence as denoted by SEQ ID NO. 2, or a derivative thereof comprising the amino acid sequence as denoted by SEQ ID NO. 13, or a composition comprising said tPA mutant or derivative.

8. A method for inhibiting the anticoagulating activity of an anti-coagulating agent that is coumadin or a heparin-like molecule, in a subject in need suffering from a disorder or condition that is not a brain or neural disorder or trauma, the method comprising:
   administering to said subject a therapeutically effective amount of at least one tPA mutant, wherein said mutant is selected from the group consisting of:
   (a) a tPA mutant designated tPASer481Ala comprising the amino acid sequence as denoted by SEQ ID NO. 1, or a derivative thereof comprising the amino acid sequence as denoted by SEQ ID NO. 12; and
   (b) a WA mutant designated tPASer481 Ala-DS comprising the amino acid sequence as denoted by SEQ ID NO. 2, or a derivative thereof comprising the amino acid sequence as denoted by SEQ ID NO. 13;
   or of a composition comprising the same.

9. The method according to claim 8, wherein said administering step comprises administering a tPA mutant designated tPA$^{Ser481Ala}$ comprising the amino acid sequence as denoted by SEQ ID NO. 1, or a derivative thereof comprising the amino acid sequence as denoted by SEQ ID NO. 12, or a composition comprising said tPA mutant or derivative.

10. The method according to claim 8, wherein said administering step comprises administering a tPA mutant designated tPA$^{Ser481Ala-DS}$ comprising the amino acid sequence as denoted by SEQ ID NO. 2, or a derivative thereof comprising the amino acid sequence as denoted by SEQ ID NO. 13, or a composition comprising said tPA mutant or derivative.

11. A method for the treatment, amuelioration or inhibition of a disease, disorder, or condition associated with fibrinolysis in a subject in need thereof, with the proviso that said disorder is not a brain or neural disorder or trauma, the method comprising:
 administering to said subject a therapeutically effective amount of at least one tPA mutant selected from the group consisting of:
  (a) a tPA mutant: designated tPASer481Ala and comprises the amino acid sequence as denoted by SEQ ID NO. 1, or a derivative thereof comprising the amino acid sequence as denoted by SEQ ID NO. 12; and
  (b) a tPA mutant designated tPASer481Ala-DS comprising the amino acid sequence as denoted by SEQ ID NO. 2, or a derivative thereof comprising the amino acid sequence as denoted by SEQ ID NO. 13;
 or of a composition comprising the same.

12. The method according to claim 11, wherein said disease, disorder, or condition is any one of coagulopathy, thrombocytopenia, hemorrhage, non-compressible hemorrhage, trauma induced hemorrhage, gynecological hemorrhage, minor surgery or major surgery bleeding, congenital coagulopathy, hemophilia, disseminated intravascular coagulation (DIC), gynecologic bleeding, gastrointestinal bleeding, internal bleeding and conditions related to angiogenesis.

13. The method according to claim 11, wherein said administering step comprises administering a tPA mutant designated $tPA^{Ser481Ala}$ comprising the amino acid sequence as denoted by SEQ ID NO. 1, or a derivative thereof comprising the amino acid sequence as denoted by SEQ ID NO, 12, or a composition comprising said tPA mutant or derivative.

14. The method according to claim 11, wherein said administering step comprises administering a tPA mutant designated $tPA^{Ser481Ala-DS}$ comprising the amino acid sequence as denoted by SEQ ID NO. 2, or a derivative thereof comprising the amino acid sequence as denoted by SEQ ID NO. 13, or a composition comprising said tPA mutant or derivative.

* * * * *

UNITED STATES PATENT AND TRADEMARK OFFICE
CERTIFICATE OF CORRECTION

PATENT NO. : 10,188,706 B2
APPLICATION NO. : 14/412873
DATED : January 29, 2019
INVENTOR(S) : Abd Higazi et al.

Page 1 of 1

It is certified that error appears in the above-identified patent and that said Letters Patent is hereby corrected as shown below:

In the Claims

At Claim 8, Column 72, Line 47, delete "WA" and insert --tPA--

Signed and Sealed this
Twenty-ninth Day of October, 2019

Andrei Iancu
*Director of the United States Patent and Trademark Office*

SEQUENCE LISTING

<160> NUMBER OF SEQ ID NOS: 17

<210> SEQ ID NO 1
<211> LENGTH: 530
<212> TYPE: PRT
<213> ORGANISM: Homo sapiens

<400> SEQUENCE: 1

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
            20                  25                  30

Arg Val Glu Tyr Cys Trp Cys Asn Ser Gly Arg Ala Gln Cys His Ser
        35                  40                  45

Val Pro Val Lys Ser Cys Ser Glu Pro Arg Cys Phe Asn Gly Gly Thr
    50                  55                  60

Cys Gln Gln Ala Leu Tyr Phe Ser Asp Phe Val Cys Gln Cys Pro Glu
65                  70                  75                  80

Gly Phe Ala Gly Lys Cys Cys Glu Ile Asp Thr Arg Ala Thr Cys Tyr
                85                  90                  95

Glu Asp Gln Gly Ile Ser Tyr Arg Gly Thr Trp Ser Thr Ala Glu Ser
            100                 105                 110

Gly Ala Glu Cys Thr Asn Trp Asn Ser Ser Ala Leu Ala Gln Lys Pro
        115                 120                 125

Tyr Ser Gly Arg Arg Pro Asp Ala Ile Arg Leu Gly Leu Gly Asn His
    130                 135                 140

Asn Tyr Cys Arg Asn Pro Asp Arg Asp Ser Lys Pro Trp Cys Tyr Val
145                 150                 155                 160

Phe Lys Ala Gly Lys Tyr Ser Ser Glu Phe Cys Ser Thr Pro Ala Cys
                165                 170                 175

Ser Glu Gly Asn Ser Asp Cys Tyr Phe Gly Asn Gly Ser Ala Tyr Arg
            180                 185                 190

Gly Thr His Ser Leu Thr Glu Ser Gly Ala Ser Cys Leu Pro Trp Asn
        195                 200                 205

Ser Met Ile Leu Ile Gly Lys Val Tyr Thr Ala Gln Asn Pro Ser Ala
    210                 215                 220

Gln Ala Leu Gly Leu Gly Lys His Asn Tyr Cys Arg Asn Pro Asp Gly
225                 230                 235                 240

Asp Ala Lys Pro Trp Cys His Val Leu Lys Asn Arg Arg Leu Thr Trp
                245                 250                 255

Glu Tyr Cys Asp Val Pro Ser Cys Ser Thr Cys Gly Leu Arg Gln Tyr
            260                 265                 270

Ser Gln Pro Gln Phe Arg Ile Lys Gly Gly Leu Phe Ala Asp Ile Ala
        275                 280                 285

Ser His Pro Trp Gln Ala Ala Ile Phe Ala Lys His Arg Arg Ser Pro
    290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu Glu
            340                 345                 350

Gln Lys Phe Glu Val Glu Lys Tyr Ile Val His Lys Glu Phe Asp Asp
        355                 360                 365

Asp Thr Tyr Asp Asn Asp Ile Ala Leu Leu Gln Leu Lys Ser Asp Ser
     370                 375                 380

Ser Arg Cys Ala Gln Glu Ser Ser Val Val Arg Thr Val Cys Leu Pro
385                 390                 395                 400

Pro Ala Asp Leu Gln Leu Pro Asp Trp Thr Glu Cys Glu Leu Ser Gly
                405                 410                 415

Tyr Gly Lys His Glu Ala Leu Ser Pro Phe Tyr Ser Glu Arg Leu Lys
                420                 425                 430

Glu Ala His Val Arg Leu Tyr Pro Ser Ser Arg Cys Thr Ser Gln His
                435                 440                 445

Leu Leu Asn Arg Thr Val Thr Asp Asn Met Leu Cys Ala Gly Asp Thr
450                 455                 460

Arg Ser Gly Gly Pro Gln Ala Asn Leu His Asp Ala Cys Gln Gly Asp
465                 470                 475                 480

Ala Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
                500                 505                 510

Val Tyr Thr Lys Val Thr Asn Tyr Leu Asp Trp Ile Arg Asp Asn Met
                515                 520                 525

Arg Pro
530

<210> SEQ ID NO 2
<211> LENGTH: 530
<212> TYPE: PRT
<213> ORGANISM: Homo sapiens

<400> SEQUENCE: 2

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
                20                  25                  30

Arg Val Glu Tyr Cys Trp Cys Asn Ser Gly Arg Ala Gln Cys His Ser
            35                  40                  45

Val Pro Val Lys Ser Cys Ser Glu Pro Arg Cys Phe Asn Gly Gly Thr
50                  55                  60

Cys Gln Gln Ala Leu Tyr Phe Ser Asp Phe Val Cys Gln Cys Pro Glu
65                  70                  75                  80

Gly Phe Ala Gly Lys Cys Cys Glu Ile Asp Thr Arg Ala Thr Cys Tyr
                85                  90                  95

Glu Asp Gln Gly Ile Ser Tyr Arg Gly Thr Trp Ser Thr Ala Glu Ser
                100                 105                 110

Gly Ala Glu Cys Thr Asn Trp Asn Ser Ser Ala Leu Ala Gln Lys Pro
            115                 120                 125

Tyr Ser Gly Arg Arg Pro Asp Ala Ile Arg Leu Gly Leu Gly Asn His
130                 135                 140

Asn Tyr Cys Arg Asn Pro Asp Arg Asp Ser Lys Pro Trp Cys Tyr Val
145                 150                 155                 160

Phe Lys Ala Gly Lys Tyr Ser Ser Glu Phe Cys Ser Thr Pro Ala Cys
                165                 170                 175

Ser Glu Gly Asn Ser Asp Cys Tyr Phe Gly Asn Gly Ser Ala Tyr Arg
                180                 185                 190

Gly Thr His Ser Leu Thr Glu Ser Gly Ala Ser Cys Leu Pro Trp Asn
            195                 200                 205

```
Ser Met Ile Leu Ile Gly Lys Val Tyr Thr Ala Gln Asn Pro Ser Ala
    210                 215                 220

Gln Ala Leu Gly Leu Gly Lys His Asn Tyr Cys Arg Asn Pro Asp Gly
225                 230                 235                 240

Asp Ala Lys Pro Trp Cys His Val Leu Lys Asn Arg Arg Leu Thr Trp
                245                 250                 255

Glu Tyr Cys Asp Val Pro Ser Cys Ser Thr Cys Gly Leu Arg Gln Tyr
                260                 265                 270

Ser Gln Pro Gln Phe Arg Ile Lys Gly Gly Leu Phe Ala Asp Ile Ala
                275                 280                 285

Ser His Pro Trp Gln Ala Ala Ile Phe Ala Ala Ala Ala Ser Pro
    290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu Glu
                340                 345                 350

Gln Lys Phe Glu Val Glu Lys Tyr Ile Val His Lys Glu Phe Asp Asp
                355                 360                 365

Asp Thr Tyr Asp Asn Asp Ile Ala Leu Leu Gln Leu Lys Ser Asp Ser
    370                 375                 380

Ser Arg Cys Ala Gln Glu Ser Ser Val Val Arg Thr Val Cys Leu Pro
385                 390                 395                 400

Pro Ala Asp Leu Gln Leu Pro Asp Trp Thr Glu Cys Glu Leu Ser Gly
                405                 410                 415

Tyr Gly Lys His Glu Ala Leu Ser Pro Phe Tyr Ser Glu Arg Leu Lys
                420                 425                 430

Glu Ala His Val Arg Leu Tyr Pro Ser Ser Arg Cys Thr Ser Gln His
                435                 440                 445

Leu Leu Asn Arg Thr Val Thr Asp Asn Met Leu Cys Ala Gly Asp Thr
    450                 455                 460

Arg Ser Gly Gly Pro Gln Ala Asn Leu His Asp Ala Cys Gln Gly Asp
465                 470                 475                 480

Ala Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
                500                 505                 510

Val Tyr Thr Lys Val Thr Asn Tyr Leu Asp Trp Ile Arg Asp Asn Met
    515                 520                 525

Arg Pro
    530

<210> SEQ ID NO 3
<211> LENGTH: 530
<212> TYPE: PRT
<213> ORGANISM: Homo sapiens

<400> SEQUENCE: 3

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
                20                  25                  30

Arg Val Glu Tyr Cys Trp Cys Asn Ser Gly Arg Ala Gln Cys His Ser
            35                  40                  45
```

```
Val Pro Val Lys Ser Cys Ser Glu Pro Arg Cys Phe Asn Gly Gly Thr
 50              55                  60
Cys Gln Gln Ala Leu Tyr Phe Ser Asp Phe Val Cys Gln Cys Pro Glu
 65                  70                  75                  80
Gly Phe Ala Gly Lys Cys Cys Glu Ile Asp Thr Arg Ala Thr Cys Tyr
                 85                  90                  95
Glu Asp Gln Gly Ile Ser Tyr Arg Gly Asn Trp Ser Thr Ala Glu Ser
                100                 105                 110
Gly Ala Glu Cys Thr Asn Trp Gln Ser Ser Ala Leu Ala Gln Lys Pro
                115                 120                 125
Tyr Ser Gly Arg Arg Pro Asp Ala Ile Arg Leu Gly Leu Gly Asn His
130                 135                 140
Asn Tyr Cys Arg Asn Pro Asp Arg Asp Ser Lys Pro Trp Cys Tyr Val
145                 150                 155                 160
Phe Lys Ala Gly Lys Tyr Ser Ser Glu Phe Cys Ser Thr Pro Ala Cys
                165                 170                 175
Ser Glu Gly Asn Ser Asp Cys Tyr Phe Gly Asn Gly Ser Ala Tyr Arg
                180                 185                 190
Gly Thr His Ser Leu Thr Glu Ser Gly Ala Ser Cys Leu Pro Trp Asn
                195                 200                 205
Ser Met Ile Leu Ile Gly Lys Val Tyr Thr Ala Gln Asn Pro Ser Ala
210                 215                 220
Gln Ala Leu Gly Leu Gly Lys His Asn Tyr Cys Arg Asn Pro Asp Gly
225                 230                 235                 240
Asp Ala Lys Pro Trp Cys His Val Leu Lys Asn Arg Arg Leu Thr Trp
                245                 250                 255
Glu Tyr Cys Asp Val Pro Ser Cys Ser Thr Cys Gly Leu Arg Gln Tyr
                260                 265                 270
Ser Gln Pro Gln Phe Arg Ile Lys Gly Gly Leu Phe Ala Asp Ile Ala
                275                 280                 285
Ser His Pro Trp Gln Ala Ala Ile Phe Ala Lys His Arg Arg Ser Pro
                290                 295                 300
Gly Glu Arg Phe Leu Cys Gly Gly Ile Leu Ile Ser Ser Cys Trp Ile
305                 310                 315                 320
Leu Ser Ala Ala His Cys Phe Gln Glu Arg Phe Pro Pro His His Leu
                325                 330                 335
Thr Val Ile Leu Gly Arg Thr Tyr Arg Val Val Pro Gly Glu Glu Glu
                340                 345                 350
Gln Lys Phe Glu Val Glu Lys Tyr Ile Val His Lys Glu Phe Asp Asp
                355                 360                 365
Asp Thr Tyr Asp Asn Asp Ile Ala Leu Leu Gln Leu Lys Ser Asp Ser
                370                 375                 380
Ser Arg Cys Ala Gln Glu Ser Ser Val Val Arg Thr Val Cys Leu Pro
385                 390                 395                 400
Pro Ala Asp Leu Gln Leu Pro Asp Trp Thr Glu Cys Glu Leu Ser Gly
                405                 410                 415
Tyr Gly Lys His Glu Ala Leu Ser Pro Phe Tyr Ser Arg Leu Lys
                420                 425                 430
Glu Ala His Val Arg Leu Tyr Pro Ser Ser Arg Cys Thr Ser Gln His
                435                 440                 445
Leu Leu Asn Arg Thr Val Thr Asp Asn Met Leu Cys Ala Gly Asp Thr
450                 455                 460
```

```
Arg Ser Gly Gly Pro Gln Ala Asn Leu His Asp Ala Cys Gln Gly Asp
465                 470                 475                 480

Ala Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
            500                 505                 510

Val Tyr Thr Lys Val Thr Asn Tyr Leu Asp Trp Ile Arg Asp Asn Met
        515                 520                 525

Arg Pro
    530

<210> SEQ ID NO 4
<211> LENGTH: 355
<212> TYPE: PRT
<213> ORGANISM: Homo sapiens

<400> SEQUENCE: 4

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
        115                 120                 125

Pro Gly Glu Arg Phe Leu Cys Gly Gly Ile Leu Ile Ser Ser Cys Trp
130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
            180                 185                 190

Asp Asp Thr Tyr Asp Asn Asp Ile Ala Leu Leu Gln Leu Lys Ser Asp
        195                 200                 205

Ser Ser Arg Cys Ala Gln Glu Ser Ser Val Val Arg Thr Val Cys Leu
210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
            260                 265                 270

His Leu Leu Asn Arg Thr Val Thr Asp Asn Met Leu Cys Ala Gly Asp
        275                 280                 285

Thr Arg Ser Gly Gly Pro Gln Ala Asn Leu His Asp Ala Cys Gln Gly
290                 295                 300
```

```
Asp Ala Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
            325                 330                 335

Gly Val Tyr Thr Lys Val Thr Asn Tyr Leu Asp Trp Ile Arg Asp Asn
            340                 345                 350

Met Arg Pro
        355

<210> SEQ ID NO 5
<211> LENGTH: 411
<212> TYPE: PRT
<213> ORGANISM: Homo sapiens

<400> SEQUENCE: 5

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
        115                 120                 125

His Asp Cys Ala Asp Gly Lys Lys Pro Ser Ser Pro Pro Glu Glu Leu
    130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
    210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285

Phe Gly Thr Ser Cys Glu Ile Thr Gly Phe Gly Lys Glu Asn Ser Thr
    290                 295                 300

Asp Tyr Leu Tyr Pro Glu Gln Leu Lys Met Thr Val Val Lys Leu Ile
305                 310                 315                 320
```

```
Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ala Gly Pro Leu Val Cys Ser Leu Gln Gly Arg Met
        355                 360                 365

Thr Leu Thr Gly Ile Val Ser Trp Arg Gly Cys Ala Leu Lys Asp
    370                 375                 380

Lys Pro Gly Val Tyr Thr Arg Val Ser His Phe Leu Pro Trp Ile Arg
385                 390                 395                 400

Ser His Thr Lys Glu Glu Asn Gly Leu Ala Leu
                405                 410

<210> SEQ ID NO 6
<211> LENGTH: 411
<212> TYPE: PRT
<213> ORGANISM: Homo sapiens

<400> SEQUENCE: 6

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
        115                 120                 125

His Asp Cys Ala Asp Gly Lys Lys Pro Ser Ser Pro Pro Glu Glu Leu
    130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
    210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285
```

```
Phe Gly Thr Ser Cys Glu Ile Thr Gly Phe Gly Lys Glu Asn Ser Thr
    290                 295                 300
Asp Tyr Leu Tyr Pro Glu Gln Leu Lys Met Thr Val Val Lys Leu Ile
305                 310                 315                 320
Ser His Arg Glu Cys Gln Gln Pro His Tyr Tyr Gly Ser Glu Val Thr
                325                 330                 335
Thr Lys Met Leu Cys Ala Ala Asp Pro Gln Trp Lys Thr Asp Ser Cys
            340                 345                 350
Gln Gly Asp Ser Gly Gly Pro Leu Val Cys Ser Leu Gln Gly Arg Met
        355                 360                 365
Thr Leu Thr Gly Ile Val Ser Trp Gly Arg Gly Cys Ala Leu Lys Asp
370                 375                 380
Lys Pro Gly Val Tyr Thr Arg Val Ser His Phe Leu Pro Trp Ile Arg
385                 390                 395                 400
Ser His Thr Lys Glu Glu Asn Gly Leu Ala Leu
                405                 410

<210> SEQ ID NO 7
<211> LENGTH: 530
<212> TYPE: PRT
<213> ORGANISM: Homo sapiens

<400> SEQUENCE: 7

Gly Ala Arg Ser Tyr Gln Val Ile Cys Arg Asp Glu Lys Thr Gln Met
1               5                   10                  15
Ile Tyr Gln Gln His Gln Ser Trp Leu Arg Pro Val Leu Arg Ser Asn
            20                  25                  30
Arg Val Glu Tyr Cys Trp Cys Asn Ser Gly Arg Ala Gln Cys His Ser
        35                  40                  45
Val Pro Val Lys Ser Cys Ser Glu Pro Arg Cys Phe Asn Gly Gly Thr
    50                  55                  60
Cys Gln Gln Ala Leu Tyr Phe Ser Asp Phe Val Cys Gln Cys Pro Glu
65                  70                  75                  80
Gly Phe Ala Gly Lys Cys Cys Glu Ile Asp Thr Arg Ala Thr Cys Tyr
                85                  90                  95
Glu Asp Gln Gly Ile Ser Tyr Arg Gly Thr Trp Ser Thr Ala Glu Ser
            100                 105                 110
Gly Ala Glu Cys Thr Asn Trp Asn Ser Ser Ala Leu Ala Gln Lys Pro
        115                 120                 125
Tyr Ser Gly Arg Arg Pro Asp Ala Ile Arg Leu Gly Leu Gly Asn His
    130                 135                 140
Asn Tyr Cys Arg Asn Pro Asp Arg Asp Ser Lys Pro Trp Cys Tyr Val
145                 150                 155                 160
Phe Lys Ala Gly Lys Tyr Ser Ser Glu Phe Cys Ser Thr Pro Ala Cys
                165                 170                 175
Ser Glu Gly Asn Ser Asp Cys Tyr Phe Gly Asn Gly Ser Ala Tyr Arg
            180                 185                 190
Gly Thr His Ser Leu Thr Glu Ser Gly Ala Ser Cys Leu Pro Trp Asn
        195                 200                 205
Ser Met Ile Leu Ile Gly Lys Val Tyr Thr Ala Gln Asn Pro Ser Ala
    210                 215                 220
Gln Ala Leu Gly Leu Gly Lys His Asn Tyr Cys Arg Asn Pro Asp Gly
225                 230                 235                 240
Asp Ala Lys Pro Trp Cys His Val Leu Lys Asn Arg Arg Leu Thr Trp
                245                 250                 255
```

Glu Tyr Cys Asp Val Pro Ser Cys Ser Thr Cys Gly Leu Arg Gln Tyr
                260                 265                 270

Ser Gln Pro Gln Phe Arg Ile Lys Gly Gly Leu Phe Ala Asp Ile Ala
            275                 280                 285

Ser His Pro Trp Gln Ala Ala Ile Phe Ala Lys His Arg Arg Ser Pro
        290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu Glu
                340                 345                 350

Gln Lys Phe Glu Val Glu Lys Tyr Ile Val His Lys Glu Phe Asp Asp
            355                 360                 365

Asp Thr Tyr Asp Asn Asp Ile Ala Leu Leu Gln Leu Lys Ser Asp Ser
        370                 375                 380

Ser Arg Cys Ala Gln Glu Ser Ser Val Val Arg Thr Val Cys Leu Pro
385                 390                 395                 400

Pro Ala Asp Leu Gln Leu Pro Asp Trp Thr Glu Cys Glu Leu Ser Gly
                405                 410                 415

Tyr Gly Lys His Glu Ala Leu Ser Pro Phe Tyr Ser Glu Arg Leu Lys
                420                 425                 430

Glu Ala His Val Arg Leu Tyr Pro Ser Ser Arg Cys Thr Ser Gln His
            435                 440                 445

Leu Leu Asn Arg Thr Val Thr Asp Asn Met Leu Cys Ala Gly Asp Thr
        450                 455                 460

Arg Ser Gly Gly Pro Gln Ala Asn Leu His Asp Ala Cys Gln Gly Asp
465                 470                 475                 480

Ser Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
                500                 505                 510

Val Tyr Thr Lys Val Thr Asn Tyr Leu Asp Trp Ile Arg Asp Asn Met
            515                 520                 525

Arg Pro
    530

<210> SEQ ID NO 8
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer htPA-Bgl II

<400> SEQUENCE: 8
gcccgattca gatctggagc ccgcagctac caagtgatc                                    39

<210> SEQ ID NO 9
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer htPA-Xho I

```
<400> SEQUENCE: 9
ttttgaggac tcgagtgttc cttatcacgg tcgcatg                              37

<210> SEQ ID NO 10
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-parallel primers for introduction of the
      S481A mutation - Primer S481A

<400> SEQUENCE: 10
gcctgccagg gcgatgccgg aggcccctg gtg                                  33

<210> SEQ ID NO 11
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-parallel primers for introduction of the
      S481A mutation - Primer S481A reverse

<400> SEQUENCE: 11
caccaggggg cctccggcat cgccctggca ggc                                 33

<210> SEQ ID NO 12
<211> LENGTH: 532
<212> TYPE: PRT
<213> ORGANISM: Homo sapiens

<400> SEQUENCE: 12

Arg Ser Gly Ala Arg Ser Tyr Gln Val Ile Cys Arg Asp Glu Lys Thr
1               5                   10                  15

Gln Met Ile Tyr Gln Gln His Gln Ser Trp Leu Arg Pro Val Leu Arg
            20                  25                  30

Ser Asn Arg Val Glu Tyr Cys Trp Cys Asn Ser Gly Arg Ala Gln Cys
        35                  40                  45

His Ser Val Pro Val Lys Ser Cys Ser Glu Pro Arg Cys Phe Asn Gly
    50                  55                  60

Gly Thr Cys Gln Gln Ala Leu Tyr Phe Ser Asp Phe Val Cys Gln Cys
65                  70                  75                  80

Pro Glu Gly Phe Ala Gly Lys Cys Cys Glu Ile Asp Thr Arg Ala Thr
                85                  90                  95

Cys Tyr Glu Asp Gln Gly Ile Ser Tyr Arg Gly Thr Trp Ser Thr Ala
            100                 105                 110

Glu Ser Gly Ala Glu Cys Thr Asn Trp Asn Ser Ser Ala Leu Ala Gln
        115                 120                 125

Lys Pro Tyr Ser Gly Arg Arg Pro Asp Ala Ile Arg Leu Gly Leu Gly
    130                 135                 140

Asn His Asn Tyr Cys Arg Asn Pro Asp Arg Asp Ser Lys Pro Trp Cys
145                 150                 155                 160

Tyr Val Phe Lys Ala Gly Lys Tyr Ser Ser Glu Phe Cys Ser Thr Pro
                165                 170                 175

Ala Cys Ser Glu Gly Asn Ser Asp Cys Tyr Phe Gly Asn Gly Ser Ala
            180                 185                 190
```

-continued

```
Tyr Arg Gly Thr His Ser Leu Thr Glu Ser Gly Ala Ser Cys Leu Pro
            195                 200                 205

Trp Asn Ser Met Ile Leu Ile Gly Lys Val Tyr Thr Ala Gln Asn Pro
        210                 215                 220

Ser Ala Gln Ala Leu Gly Leu Gly Lys His Asn Tyr Cys Arg Asn Pro
225                 230                 235                 240

Asp Gly Asp Ala Lys Pro Trp Cys His Val Leu Lys Asn Arg Arg Leu
                245                 250                 255

Thr Trp Glu Tyr Cys Asp Val Pro Ser Cys Ser Thr Cys Gly Leu Arg
            260                 265                 270

Gln Tyr Ser Gln Pro Gln Phe Arg Ile Lys Gly Gly Leu Phe Ala Asp
        275                 280                 285

Ile Ala Ser His Pro Trp Gln Ala Ala Ile Phe Ala Lys His Arg Arg
    290                 295                 300

Ser Pro Gly Glu Arg Phe Leu Cys Gly Gly Ile Leu Ile Ser Ser Cys
305                 310                 315                 320

Trp Ile Leu Ser Ala Ala His Cys Phe Gln Glu Arg Phe Pro Pro His
                325                 330                 335

His Leu Thr Val Ile Leu Gly Arg Thr Tyr Arg Val Val Pro Gly Glu
            340                 345                 350

Glu Glu Gln Lys Phe Glu Val Glu Lys Tyr Ile Val His Lys Glu Phe
        355                 360                 365

Asp Asp Asp Thr Tyr Asp Asn Asp Ile Ala Leu Leu Gln Leu Lys Ser
    370                 375                 380

Asp Ser Ser Arg Cys Ala Gln Glu Ser Ser Val Val Arg Thr Val Cys
385                 390                 395                 400

Leu Pro Pro Ala Asp Leu Gln Leu Pro Asp Trp Thr Glu Cys Glu Leu
                405                 410                 415

Ser Gly Tyr Gly Lys His Glu Ala Leu Ser Pro Phe Tyr Ser Glu Arg
            420                 425                 430

Leu Lys Glu Ala His Val Arg Leu Tyr Pro Ser Ser Arg Cys Thr Ser
        435                 440                 445

Gln His Leu Leu Asn Arg Thr Val Thr Asp Asn Met Leu Cys Ala Gly
    450                 455                 460

Asp Thr Arg Ser Gly Gly Pro Gln Ala Asn Leu His Asp Ala Cys Gln
465                 470                 475                 480

Gly Asp Ala Gly Gly Pro Leu Val Cys Leu Asn Asp Gly Arg Met Thr
                485                 490                 495

Leu Val Gly Ile Ile Ser Trp Gly Leu Gly Cys Gly Gln Lys Asp Val
            500                 505                 510

Pro Gly Val Tyr Thr Lys Val Thr Asn Tyr Leu Asp Trp Ile Arg Asp
        515                 520                 525

Asn Met Arg Pro
530
```

<210> SEQ ID NO 13
<211> LENGTH: 532
<212> TYPE: PRT
<213> ORGANISM: Homo sapiens

<400> SEQUENCE: 13

```
Arg Ser Gly Ala Arg Ser Tyr Gln Val Ile Cys Arg Asp Glu Lys Thr
1               5                   10                  15

Gln Met Ile Tyr Gln Gln His Gln Ser Trp Leu Arg Pro Val Leu Arg
            20                  25                  30
```

```
Ser Asn Arg Val Glu Tyr Cys Trp Cys Asn Ser Gly Arg Ala Gln Cys
         35                  40                  45

His Ser Val Pro Val Lys Ser Cys Ser Glu Pro Arg Cys Phe Asn Gly
 50                  55                  60

Gly Thr Cys Gln Gln Ala Leu Tyr Phe Ser Asp Phe Val Cys Gln Cys
 65                  70                  75                  80

Pro Glu Gly Phe Ala Gly Lys Cys Cys Glu Ile Asp Thr Arg Ala Thr
                 85                  90                  95

Cys Tyr Glu Asp Gln Gly Ile Ser Tyr Arg Gly Thr Trp Ser Thr Ala
                100                 105                 110

Glu Ser Gly Ala Glu Cys Thr Asn Trp Asn Ser Ser Ala Leu Ala Gln
            115                 120                 125

Lys Pro Tyr Ser Gly Arg Arg Pro Asp Ala Ile Arg Leu Gly Leu Gly
        130                 135                 140

Asn His Asn Tyr Cys Arg Asn Pro Asp Arg Asp Ser Lys Pro Trp Cys
145                 150                 155                 160

Tyr Val Phe Lys Ala Gly Lys Tyr Ser Ser Glu Phe Cys Ser Thr Pro
                165                 170                 175

Ala Cys Ser Glu Gly Asn Ser Asp Cys Tyr Phe Gly Asn Gly Ser Ala
            180                 185                 190

Tyr Arg Gly Thr His Ser Leu Thr Glu Ser Gly Ala Ser Cys Leu Pro
        195                 200                 205

Trp Asn Ser Met Ile Leu Ile Gly Lys Val Tyr Thr Ala Gln Asn Pro
210                 215                 220

Ser Ala Gln Ala Leu Gly Leu Gly Lys His Asn Tyr Cys Arg Asn Pro
225                 230                 235                 240

Asp Gly Asp Ala Lys Pro Trp Cys His Val Leu Lys Asn Arg Arg Leu
                245                 250                 255

Thr Trp Glu Tyr Cys Asp Val Pro Ser Cys Ser Thr Cys Gly Leu Arg
            260                 265                 270

Gln Tyr Ser Gln Pro Gln Phe Arg Ile Lys Gly Gly Leu Phe Ala Asp
        275                 280                 285

Ile Ala Ser His Pro Trp Gln Ala Ala Ile Phe Ala Ala Ala Ala
290                 295                 300

Ser Pro Gly Glu Arg Phe Leu Cys Gly Gly Ile Leu Ile Ser Ser Cys
305                 310                 315                 320

Trp Ile Leu Ser Ala Ala His Cys Phe Gln Glu Arg Phe Pro Pro His
                325                 330                 335

His Leu Thr Val Ile Leu Gly Arg Thr Tyr Arg Val Val Pro Gly Glu
            340                 345                 350

Glu Glu Gln Lys Phe Glu Val Glu Lys Tyr Ile Val His Lys Glu Phe
        355                 360                 365

Asp Asp Asp Thr Tyr Asp Asn Asp Ile Ala Leu Leu Gln Leu Lys Ser
370                 375                 380

Asp Ser Ser Arg Cys Ala Gln Glu Ser Ser Val Val Arg Thr Val Cys
385                 390                 395                 400

Leu Pro Pro Ala Asp Leu Gln Leu Pro Asp Trp Thr Glu Cys Glu Leu
                405                 410                 415

Ser Gly Tyr Gly Lys His Glu Ala Leu Ser Pro Phe Tyr Ser Glu Arg
            420                 425                 430

Leu Lys Glu Ala His Val Arg Leu Tyr Pro Ser Ser Arg Cys Thr Ser
        435                 440                 445
```

```
Gln His Leu Leu Asn Arg Thr Val Thr Asp Asn Met Leu Cys Ala Gly
    450                 455                 460
Asp Thr Arg Ser Gly Gly Pro Gln Ala Asn Leu His Asp Ala Cys Gln
465                 470                 475                 480
Gly Asp Ala Gly Gly Pro Leu Val Cys Leu Asn Asp Gly Arg Met Thr
                485                 490                 495
Leu Val Gly Ile Ile Ser Trp Gly Leu Gly Cys Gly Gln Lys Asp Val
            500                 505                 510
Pro Gly Val Tyr Thr Lys Val Thr Asn Tyr Leu Asp Trp Ile Arg Asp
        515                 520                 525
Asn Met Arg Pro
    530

<210> SEQ ID NO 14
<211> LENGTH: 532
<212> TYPE: PRT
<213> ORGANISM: Homo sapiens

<400> SEQUENCE: 14

Arg Ser Gly Ala Arg Ser Tyr Gln Val Ile Cys Arg Asp Glu Lys Thr
1               5                   10                  15
Gln Met Ile Tyr Gln Gln His Gln Ser Trp Leu Arg Pro Val Leu Arg
            20                  25                  30
Ser Asn Arg Val Glu Tyr Cys Trp Cys Asn Ser Gly Arg Ala Gln Cys
        35                  40                  45
His Ser Val Pro Val Lys Ser Cys Ser Glu Pro Arg Cys Phe Asn Gly
    50                  55                  60
Gly Thr Cys Gln Gln Ala Leu Tyr Phe Ser Asp Phe Val Cys Gln Cys
65                  70                  75                  80
Pro Glu Gly Phe Ala Gly Lys Cys Cys Glu Ile Asp Thr Arg Ala Thr
                85                  90                  95
Cys Tyr Glu Asp Gln Gly Ile Ser Tyr Arg Gly Asn Trp Ser Thr Ala
            100                 105                 110
Glu Ser Gly Ala Glu Cys Thr Asn Trp Gln Ser Ser Ala Leu Ala Gln
        115                 120                 125
Lys Pro Tyr Ser Gly Arg Arg Pro Asp Ala Ile Arg Leu Gly Leu Gly
    130                 135                 140
Asn His Asn Tyr Cys Arg Asn Pro Asp Arg Asp Ser Lys Pro Trp Cys
145                 150                 155                 160
Tyr Val Phe Lys Ala Gly Lys Tyr Ser Ser Glu Phe Cys Ser Thr Pro
                165                 170                 175
Ala Cys Ser Glu Gly Asn Ser Asp Cys Tyr Phe Gly Asn Gly Ser Ala
            180                 185                 190
Tyr Arg Gly Thr His Ser Leu Thr Glu Ser Gly Ala Ser Cys Leu Pro
        195                 200                 205
Trp Asn Ser Met Ile Leu Ile Gly Lys Val Tyr Thr Ala Gln Asn Pro
    210                 215                 220
Ser Ala Gln Ala Leu Gly Leu Gly Lys His Asn Tyr Cys Arg Asn Pro
225                 230                 235                 240
Asp Gly Asp Ala Lys Pro Trp Cys His Val Leu Lys Asn Arg Arg Leu
                245                 250                 255
Thr Trp Glu Tyr Cys Asp Val Pro Ser Cys Ser Thr Cys Gly Leu Arg
            260                 265                 270
Gln Tyr Ser Gln Pro Gln Phe Arg Ile Lys Gly Gly Leu Phe Ala Asp
        275                 280                 285
```

```
Ile Ala Ser His Pro Trp Gln Ala Ile Phe Ala Lys His Arg Arg
    290                 295                 300

Ser Pro Gly Glu Arg Phe Leu Cys Gly Gly Ile Leu Ile Ser Ser Cys
305                 310                 315                 320

Trp Ile Leu Ser Ala Ala His Cys Phe Gln Glu Arg Phe Pro Pro His
                325                 330                 335

His Leu Thr Val Ile Leu Gly Arg Thr Tyr Arg Val Val Pro Gly Glu
            340                 345                 350

Glu Glu Gln Lys Phe Glu Val Glu Lys Tyr Ile Val His Lys Glu Phe
        355                 360                 365

Asp Asp Asp Thr Tyr Asp Asn Asp Ile Ala Leu Leu Gln Leu Lys Ser
370                 375                 380

Asp Ser Ser Arg Cys Ala Gln Glu Ser Ser Val Val Arg Thr Val Cys
385                 390                 395                 400

Leu Pro Pro Ala Asp Leu Gln Leu Pro Asp Trp Thr Glu Cys Glu Leu
                405                 410                 415

Ser Gly Tyr Gly Lys His Glu Ala Leu Ser Pro Phe Tyr Ser Glu Arg
            420                 425                 430

Leu Lys Glu Ala His Val Arg Leu Tyr Pro Ser Ser Arg Cys Thr Ser
        435                 440                 445

Gln His Leu Leu Asn Arg Thr Val Thr Asp Asn Met Leu Cys Ala Gly
450                 455                 460

Asp Thr Arg Ser Gly Gly Pro Gln Ala Asn Leu His Asp Ala Cys Gln
465                 470                 475                 480

Gly Asp Ala Gly Gly Pro Leu Val Cys Leu Asn Asp Gly Arg Met Thr
                485                 490                 495

Leu Val Gly Ile Ile Ser Trp Gly Leu Gly Cys Gly Gln Lys Asp Val
            500                 505                 510

Pro Gly Val Tyr Thr Lys Val Thr Asn Tyr Leu Asp Trp Ile Arg Asp
        515                 520                 525

Asn Met Arg Pro
    530

<210> SEQ ID NO 15
<211> LENGTH: 530
<212> TYPE: PRT
<213> ORGANISM: Homo sapiens

<400> SEQUENCE: 15

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
            20                  25                  30

Arg Val Glu Tyr Cys Trp Cys Asn Ser Gly Arg Ala Gln Cys His Ser
        35                  40                  45

Val Pro Val Lys Ser Cys Ser Glu Pro Arg Cys Phe Asn Gly Gly Thr
    50                  55                  60

Cys Gln Gln Ala Leu Tyr Phe Ser Asp Phe Val Cys Gln Cys Pro Glu
65                  70                  75                  80

Gly Phe Ala Gly Lys Cys Cys Glu Ile Asp Thr Arg Ala Thr Cys Tyr
                85                  90                  95

Glu Asp Gln Gly Ile Ser Tyr Arg Gly Thr Trp Ser Thr Ala Glu Ser
            100                 105                 110

Gly Ala Glu Cys Thr Asn Trp Asn Ser Ser Ala Leu Ala Gln Lys Pro
        115                 120                 125
```

-continued

Tyr Ser Gly Arg Arg Pro Asp Ala Ile Arg Leu Gly Leu Gly Asn His
    130                 135                 140

Asn Tyr Cys Arg Asn Pro Asp Arg Asp Ser Lys Pro Trp Cys Tyr Val
145                 150                 155                 160

Phe Lys Ala Gly Lys Tyr Ser Ser Glu Phe Cys Ser Thr Pro Ala Cys
                165                 170                 175

Ser Glu Gly Asn Ser Asp Cys Tyr Phe Gly Asn Gly Ser Ala Tyr Arg
            180                 185                 190

Gly Thr His Ser Leu Thr Glu Ser Gly Ala Ser Cys Leu Pro Trp Asn
        195                 200                 205

Ser Met Ile Leu Ile Gly Lys Val Tyr Thr Ala Gln Asn Pro Ser Ala
    210                 215                 220

Gln Ala Leu Gly Leu Gly Lys His Asn Tyr Cys Arg Asn Pro Asp Gly
225                 230                 235                 240

Asp Ala Lys Pro Trp Cys His Val Leu Lys Asn Arg Arg Leu Thr Trp
                245                 250                 255

Glu Tyr Cys Asp Val Pro Ser Cys Ser Thr Cys Gly Leu Arg Gln Tyr
            260                 265                 270

Ser Gln Pro Gln Phe Arg Ile Lys Gly Gly Leu Phe Ala Asp Ile Ala
        275                 280                 285

Ser His Pro Trp Gln Ala Ala Ile Phe Ala Ala Ala Ala Ser Pro
    290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu Glu
            340                 345                 350

Gln Lys Phe Glu Val Glu Lys Tyr Ile Val His Lys Glu Phe Asp Asp
        355                 360                 365

Asp Thr Tyr Asp Asn Asp Ile Ala Leu Leu Gln Leu Lys Ser Asp Ser
    370                 375                 380

Ser Arg Cys Ala Gln Glu Ser Ser Val Val Arg Thr Val Cys Leu Pro
385                 390                 395                 400

Pro Ala Asp Leu Gln Leu Pro Asp Trp Thr Glu Cys Glu Leu Ser Gly
                405                 410                 415

Tyr Gly Lys His Glu Ala Leu Ser Pro Phe Tyr Ser Glu Arg Leu Lys
            420                 425                 430

Glu Ala His Val Arg Leu Tyr Pro Ser Ser Arg Cys Thr Ser Gln His
        435                 440                 445

Leu Leu Asn Arg Thr Val Thr Asp Asn Met Leu Cys Ala Gly Asp Thr
    450                 455                 460

Arg Ser Gly Gly Pro Gln Ala Asn Leu His Asp Ala Cys Gln Gly Asp
465                 470                 475                 480

Ser Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
            500                 505                 510

Val Tyr Thr Lys Val Thr Asn Tyr Leu Asp Trp Ile Arg Asp Asn Met
        515                 520                 525

Arg Pro
530

```
<210> SEQ ID NO 16
<211> LENGTH: 530
<212> TYPE: PRT
<213> ORGANISM: Homo sapiens

<400> SEQUENCE: 16

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
            20                  25                  30

Arg Val Glu Tyr Cys Trp Cys Asn Ser Gly Arg Ala Gln Cys His Ser
        35                  40                  45

Val Pro Val Lys Ser Cys Ser Glu Pro Arg Cys Phe Asn Gly Gly Thr
    50                  55                  60

Cys Gln Gln Ala Leu Tyr Phe Ser Asp Phe Val Cys Gln Cys Pro Glu
65                  70                  75                  80

Gly Phe Ala Gly Lys Cys Cys Glu Ile Asp Thr Arg Ala Thr Cys Tyr
                85                  90                  95

Glu Asp Gln Gly Ile Ser Tyr Arg Gly Asn Trp Ser Thr Ala Glu Ser
            100                 105                 110

Gly Ala Glu Cys Thr Asn Trp Gln Ser Ser Ala Leu Ala Gln Lys Pro
        115                 120                 125

Tyr Ser Gly Arg Arg Pro Asp Ala Ile Arg Leu Gly Leu Gly Asn His
    130                 135                 140

Asn Tyr Cys Arg Asn Pro Asp Arg Asp Ser Lys Pro Trp Cys Tyr Val
145                 150                 155                 160

Phe Lys Ala Gly Lys Tyr Ser Ser Glu Phe Cys Ser Thr Pro Ala Cys
                165                 170                 175

Ser Glu Gly Asn Ser Asp Cys Tyr Phe Gly Asn Gly Ser Ala Tyr Arg
            180                 185                 190

Gly Thr His Ser Leu Thr Glu Ser Gly Ala Ser Cys Leu Pro Trp Asn
        195                 200                 205

Ser Met Ile Leu Ile Gly Lys Val Tyr Thr Ala Gln Asn Pro Ser Ala
    210                 215                 220

Gln Ala Leu Gly Leu Gly Lys His Asn Tyr Cys Arg Asn Pro Asp Gly
225                 230                 235                 240

Asp Ala Lys Pro Trp Cys His Val Leu Lys Asn Arg Arg Leu Thr Trp
                245                 250                 255

Glu Tyr Cys Asp Val Pro Ser Cys Ser Thr Cys Gly Leu Arg Gln Tyr
            260                 265                 270

Ser Gln Pro Gln Phe Arg Ile Lys Gly Gly Leu Phe Ala Asp Ile Ala
        275                 280                 285

Ser His Pro Trp Gln Ala Ala Ile Phe Ala Lys His Arg Arg Ser Pro
    290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu Glu
            340                 345                 350

Gln Lys Phe Glu Val Glu Lys Tyr Ile Val His Lys Glu Phe Asp Asp
        355                 360                 365

Asp Thr Tyr Asp Asn Asp Ile Ala Leu Leu Gln Leu Lys Ser Asp Ser
    370                 375                 380
```

-continued

```
Ser Arg Cys Ala Gln Glu Ser Val Val Arg Thr Val Cys Leu Pro
385                 390                 395                 400

Pro Ala Asp Leu Gln Leu Pro Asp Trp Thr Glu Cys Glu Leu Ser Gly
            405                 410                 415

Tyr Gly Lys His Glu Ala Leu Ser Pro Phe Tyr Ser Glu Arg Leu Lys
            420                 425                 430

Glu Ala His Val Arg Leu Tyr Pro Ser Ser Arg Cys Thr Ser Gln His
            435                 440                 445

Leu Leu Asn Arg Thr Val Thr Asp Asn Met Leu Cys Ala Gly Asp Thr
    450                 455                 460

Arg Ser Gly Gly Pro Gln Ala Asn Leu His Asp Ala Cys Gln Gly Asp
465                 470                 475                 480

Ser Gly Gly Pro Leu Val Cys Leu Asn Asp Gly Arg Met Thr Leu Val
            485                 490                 495

Gly Ile Ile Ser Trp Gly Leu Gly Cys Gly Gln Lys Asp Val Pro Gly
            500                 505                 510

Val Tyr Thr Lys Val Thr Asn Tyr Leu Asp Trp Ile Arg Asp Asn Met
            515                 520                 525

Arg Pro
    530

<210> SEQ ID NO 17
<211> LENGTH: 355
<212> TYPE: PRT
<213> ORGANISM: Homo sapiens

<400> SEQUENCE: 17

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
    50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
            115                 120                 125

Pro Gly Glu Arg Phe Leu Cys Gly Gly Ile Leu Ile Ser Ser Cys Trp
        130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
            180                 185                 190

Asp Asp Thr Tyr Asp Asn Asp Ile Ala Leu Leu Gln Leu Lys Ser Asp
            195                 200                 205

Ser Ser Arg Cys Ala Gln Glu Ser Val Val Arg Thr Val Cys Leu
        210                 215                 220
```

```
Pro Pro Ala Asp Leu Gln Leu Pro Asp Trp Thr Glu Cys Glu Leu Ser
225             230             235             240

Gly Tyr Gly Lys His Glu Ala Leu Ser Pro Phe Tyr Ser Glu Arg Leu
                245             250             255

Lys Glu Ala His Val Arg Leu Tyr Pro Ser Ser Arg Cys Thr Ser Gln
                260             265             270

His Leu Leu Asn Arg Thr Val Thr Asp Asn Met Leu Cys Ala Gly Asp
            275             280             285

Thr Arg Ser Gly Gly Pro Gln Ala Asn Leu His Asp Ala Cys Gln Gly
        290             295             300

Asp Ser Gly Gly Pro Leu Val Cys Leu Asn Asp Gly Arg Met Thr Leu
305             310             315             320

Val Gly Ile Ile Ser Trp Gly Leu Gly Cys Gly Gln Lys Asp Val Pro
                325             330             335

Gly Val Tyr Thr Lys Val Thr Asn Tyr Leu Asp Trp Ile Arg Asp Asn
            340             345             350

Met Arg Pro
        355
```